United States Patent
Kroczek

(10) Patent No.: US 10,703,817 B2
(45) Date of Patent: Jul. 7, 2020

(54) SYSTEM FOR DELIVERY INTO XCR1 POSITIVE CELL AND USES THEREOF

(75) Inventor: Richard Kroczek, Berlin (DE)

(73) Assignee: BUNDESREPUBLIK DEUTSCHLAND LETZVERTRETEN DURCH DAS ROBERT KOCH-INSTITUT VERTRETEN DURCH SEINEN PRAESIDENTEN, Berlin (DE)

( * ) Notice: Subject to any disclaimer, the term of this patent is extended or adjusted under 35 U.S.C. 154(b) by 358 days.

(21) Appl. No.: 12/741,798

(22) PCT Filed: Nov. 19, 2008

(86) PCT No.: PCT/EP2008/009758
§ 371 (c)(1),
(2), (4) Date: Jul. 27, 2010

(87) PCT Pub. No.: WO2009/065561
PCT Pub. Date: May 28, 2009

(65) Prior Publication Data
US 2010/0310562 A1 Dec. 9, 2010

Related U.S. Application Data

(60) Provisional application No. 61/013,263, filed on Dec. 12, 2007.

(30) Foreign Application Priority Data

Nov. 20, 2007 (EP) .................................. 07022471

(51) Int. Cl.
| | | |
|---|---|---|
| *C07K 16/28* | (2006.01) | |
| *A61K 38/19* | (2006.01) | |
| *A61K 47/64* | (2017.01) | |
| *A61K 47/68* | (2017.01) | |
| *A61K 39/385* | (2006.01) | |
| *A61K 39/00* | (2006.01) | |

(52) U.S. Cl.
CPC ........ *C07K 16/2866* (2013.01); *A61K 38/195* (2013.01); *A61K 39/385* (2013.01); *A61K 47/646* (2017.08); *A61K 47/6849* (2017.08); *A61K 2039/577* (2013.01); *A61K 2039/6056* (2013.01); *Y02A 50/41* (2018.01); *Y02A 50/412* (2018.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 5,780,268 A * | 7/1998 | Coleman et al. | ............ 435/69.5 |
| 6,153,182 A | 11/2000 | Lillard, Jr. | |
| 6,479,047 B1 | 11/2002 | Lillard, Jr. | |
| 6,719,978 B2 | 4/2004 | Schiller et al. | |
| 7,157,418 B1 | 1/2007 | McDonald et al. | |
| 2003/0007970 A1 | 1/2003 | Hedrick et al. | |
| 2003/0124267 A1 | 7/2003 | Kim | |
| 2004/0033209 A1 | 2/2004 | Mack et al. | |
| 2004/0038406 A1* | 2/2004 | Unger | .................. A61K 9/0019 435/459 |
| 2006/0257359 A1 | 11/2006 | Francois et al. | |

FOREIGN PATENT DOCUMENTS

| | | |
|---|---|---|
| EP | 1 698 902 A1 | 9/2006 |
| WO | WO-99/32137 A1 | 7/1999 |
| WO | WO 00/04926 | 2/2000 |

OTHER PUBLICATIONS

Chamberlain et al. (Expert Opinion on Pharmacotherapy, 1(4): 603-614, 2000).*
Alt et al., "Organization and Reorganization of Immunoglobulin Genes in A-MuLV-Transformed Cells: Rearrangement of Heavy but Not Light Chain Genes," *Cell* 27:381-390 (1981).
Altschul et al., "Basic Local Alignment Search Tool," *J. Mol. Biol.* 215:403-410 (1990).
Blaschke et al., "Expression of Activation-Induced, T Cell-Derived, and Chemokine-Related Cytokine/Lymphotactin and its Functional Role in Rheumatoid Arthritis," *Arthritis & Rheumatism* 48(7):1858-1872 (2003).
Bleul et al., "A Highly Efficacious Lymphocyte Chemoattractant, Stromal Cell-Derived Factor 1 (SDF-1)," *J. Exp. Med.* 184:1101-1109 (1996).
Bonifaz et al., "Efficient Targeting of Protein Antigen to the Dendritic Cell Receptor DEC-205 in the Steady State Leads to Antigen Presentation on Major Histocompatibility Complex Class 1 Products and Peripheral CD8⁺T Cell Tolerance," *J. Exp. Med.* 196(12)1627-1638 (2002).
Colvin et al., "Intracellular Domains of CXCR3 that Mediate CXCL9, CXCL10, and CXCL11 Function," *J. Biol. Chem.* 279(29):30219-30227 (2004).
Dorner et al., "MIP-1α, MIP-1β, Rantes, and ATAC/Lymphotactin Function Together with IFN-y as Type 1 Cytokines," *Proc. Natl. Acad. Sci. U.S.A.* 99(9):6181-6186 (2002).
Dorner et al., "Purification, Structural Analysis, and Function of natural ATAC, a Cytokine Secreted by CD8⁺T Cells," *J. Biol. Chem.* 272(13):8817-8823 (1997).
Foti et al., "Upon Dendritic (DC) Activation Chemokines and Chemokine Receptor Expression are Rapidly Regulated for Recruitment and Maintenance of Dc at the Inflammatory Site," *Intern. Immunol.* 11(6):979-986 (1999).

(Continued)

*Primary Examiner* — Alana Harris Dent
(74) *Attorney, Agent, or Firm* — Clark & Elbing LLP

(57) ABSTRACT

The present invention relates to a delivery system suitable for delivering a substance into a XCR1 positive professional antigen-presenting cell, one or more nucleic acids coding for the same, a vector comprising the nucleic acid(s), a medicament comprising the delivery system or the one or more nucleic acid(s) and an adjuvant comprising XCL1 or a functionally active fragment thereof.

6 Claims, 12 Drawing Sheets

Specification includes a Sequence Listing.

(56) References Cited

OTHER PUBLICATIONS

GenBank Accession No. AAB62672 (2007).
GenBank Accession No. L36149 (1995).
GenBank Accession No. NM_008510 (2010).
GenBank Accession No. NM_205152 (2011).
GenBank Accession No. P47992 (2011).
GenBank Accession No. P47993 (2011).
GenBank Accession No. P51672 (2011).
Hernandez et al., "CD4O-CD40 Ligand Interaction Between Dendritic Cells and CD8+ T Cells is Needed to Stimulate Maximal T Cell Responses in the Absence of CD4+ T Cell Help," The Journal of Immunology 178:2844-2852 (2007).
Higgins et al., "CLUSTAL V: Improved Software for Multiple Sequence Alignment," Comput. Appl. Biosci. 8:189191 (1992).
Hogquist et al., "T Cell Receptor Antagonist Peptides Induce Positive Selection," Cell 76:17-27 (1994).
Karasuyama et al., "Autocrine Growth and Tumorigencity of Interleukin 2-Dependent Helper T Cells Transfected with IL-2 Gene," J. Exp. Med. 169:13-25 (1989).
Kelner et al., "Lympohtactin: A Cytokine that Represents a New Class of Cytokine," Science 266:1395-1399 (1994).
Kennedy et al., "Molecular Cloning and Functional Characterization of Human Lymphotactin," J. Immunol. 155, 203-209 (1995).
Lenz, "$Ca^{2+}$-Controlled Competitive Diacylglycerol Binding of Protein Kinase C Isoenzymes in Living Cells," J. Cell Biol. 179:291-301 (2002).
Lin et al., "Dendritic Cell Chemotaxis and Transendothelial Migration are Induced by Distinct Chemokines and are Regulated on Maturation," Eur. J. Immunol. 28, 4114-4122 (1998).
Müller et al., "Cloning of ATAC, an Activation-Induced, Chemokine-Related Molecule Exclusively Expressed in $CD8^+T$ Lympocytes," Eur. J. Immunol. 25, 1744-1748 (1995).
Murphy et al., "Induction by Antigen of Intrathymic Apoptosis of $CD4^+$, $CD^+$, $TCR^{10}$ Thymocytes in Vivo," Science 250, 1720-1723 (1990).
Neel et al., "Chemokine Receptor Internalization and Intracellular Trafficking," Cyt. Growth Factor Rev. 16, 637-658 (2005).
Pearson and Lipman, "Improved Tools for Biological Sequence Comparison," Proc. Natl. Acad. Sci. U.S.A. 85: 2444-2448, (1988).
Raport et al., "Molecular Cloning and Functional Characterization of a Novel Human CC Chemokine Receptor (CCR5) for Rantes, MIP-1β, and MIP-1α," J. Biol. Chem. 271, 17161-17166 (1996).
Romano et al., "Induction of In Vivo Functional $D^b$-Restricted Cytolytic T Cell Activity Against a Putative Phosphate Transport Receptor of Mycobacterium Tuberculosis," J. Immunol. 172, 6913-6921 (2004).
Rose, "On the Mechanism and Significance of Ligand-Induced Internalization of Human Neutrophil Chemokine Receptors CXCR1 and CXCR2," J. Biol. Chem. 279, 24372-24386 (2004).
Sambrook et al., "Molecular Cloning, A Laboratory Manual," 2$^{nd}$ Edition, Cold Spring Harbor Laboratory, New York (1989).
Sanes et al., "Use of a Recombinant Retrovirus to Study Post-Implantation Cell Lineage in Mouse Embryos," EMBO J. 5, 3133-3142 (1986).
Sauty et al., "CXCR3 Internalization Following T Cell-Endothelial Cell Contact: Preferential Role of IFN-Inducible T Cell α Chemoattractant $(CXCL11)^1$," J. Immunol. 167, 7084-7093 (2001).
Signoret et al., "Endocytosis and Recycling of the HIV Coreceptor CCR5," J. Cell. Biol. 151, 1281-1294 (2000).
Smith and Waterman, "Comparison of Biosequences," Adv. Appl. Math. 2: 482, (1981).
Sozzani et al., "Receptor Expression and Responsiveness of Human Dendritic Cells to a Defined Set of CC and CXC Chemokines," J. Immunol. 159, 1993-2000 (1997).
Steinman et al., "Taking Dendritic Cells into Medicine," Nature 449, 419-426 (2007).
Villandagos et al., "Intrinsic and Cooperative Antigen-Presenting Functions of Dendritic-Cell Subsets in vivo," Nat. Rev. Immunol. 7:543-555 (2007).
Yoshida et al., "Molecular Cloning of a Novel C or y Type Chemokine, SCM-1," FEBS Lett. 360, 155-159 (1995).
Yoshida et al., "Structure and Expression of Two Highly Related Genes Encoding SCM-1/Human Lymphotactin," FEBS Lett. 395, 82-88 (1996).
Zhou et al., "Molecular Modeling and Site-Directed Mutagenesis of CCR5 Reveal Residues Critical for Chemokine Binding and Signal Transduction," Eur. J. Immunol. 30, 164-173 (2000).
English language translation of the Notice of Reasons for Rejection for Japanese Application No. 2014-150090, dispatched Jul. 8, 2015 (4 pages).
Akagi, "Development of polymeric nanoparticles-based vaccine," Japanese Journal of Clinical Medicine 64(2):279-285 (2006). (English language abstract provided).
Azuma, "Development of Synthetic Immunological Adjuvant and MDP-Antigen Binding Vaccine," Japanese Journal of Clinical Medicine, Takeo Endo 45(10):155-161 (1987) (No English language translation provided).
Cao et al., "Lymphotactin gene-modified bone marrow dendritic cells act as more potent adjuvants for peptide delivery to induce specific antitumor immunity," J Immunol. 161(11):6238-44 (1998).
Ishii, "Fundamental Treatment by Immune-regulating Liposomes, Supplement, Journal of Clinical and Experimental Medicine", Upper Airway Allergies Study, pp. 59-63, Mar. 2007 (No English language translation provided).
Kutomi et al., "Effective immunotherapy by HSP-cancer peptide complex and immune escape of HLA class 1 antigen down regulation," Journal of Clinical and Experimental Medicine 221(8):627-630 (2007) (No English language translation provided).
Lin et al., "Dendritic cell chemotaxis and transendothelial migration are induced by distinct chemokines and are regulated on maturation," Eur J Immunol. 28(12):4114-22 (1998).
Sozzani et al., "Receptor expression and responsiveness of human dendritic cells to a defined set of CC and CXC chemokines," J Immunol. 159(4):1993-2000 (1997).
Foti et al., "Upon dendritic cell (DC) activation chemokines and chemokine receptor expression are rapidly regulated for recruitment and maintenance of DC at the inflammatory site," Int Immunol. 11(6):979-86 (1999).
Bachem et al., "Expression of XCR1 characterizes the Batf3-dependent lineage of dendritic cells capable of antigen cross-presentation," Front Immunol. 3, Article 214:1-12, 2012.
Bonifaz et al., "In vivo targeting of antigens to maturing dendritic cells via the DEC-205 receptor improves T cell vaccination," J. Exp Med. 199:815-824, 2004.
Den Haan et al., "CD8+ but not CD8− dendritic cells cross-prime cytotoxic T cells in vivo," J Exp Med. 192:1685-1695, 2000.
Dorner et al., "Selective expression of the chemokine receptor XCR1 on cross-presenting dendritic cells determines cooperation with $CD8_+T$ cells," Immunity 31:823-833, 2009.
FactSheet on Cancer Vaccines provided by the National Cancer Institute at National Cancer Institutes of Health in Bethesda, MD, USA, 2011 (http://www.cancer.gov/cancertopics/factsheet/Therapy/cancer-vaccines).
Lazzeroni et al., "Potential use of vaccinesin the primary prevention of breast cancer in high-risk patients," Breast Care 7:281-287, 2012.
Moore et al., "Introduction of soluble protein into the class I pathway of antigen processing and presentation," Cell 54:777-785, 1988.
Naz et al., "Prophylactic vaccines for prevention of prostate cancer," Front Biosci. S4:932-940, 2012.
Saha et al., "Tumor viruses and cancer biology: Modulating signaling pathways for therapeutic intervention," Cancer Biol Ther. 10:1-18, 2010.
Tuohy et al., "Prophylactic cancer vaccination by targeting functional non-self" Ann Med. 43:356-365, 2011.
Zlotnik et al., "The chemokine superfamily revisted," Immunity 36:705-716, 2012.
Bachelerie et al., "International Union of Basic and Clinical Pharmacology. LXXXIX. Update on the extended family of chemokine receptors and introducing a new nomenclature for atypical chemokine receptors," Pharmacol Rev. 66(1):1-79 (2014).

(56) References Cited

OTHER PUBLICATIONS

Bachem et al., "Superior antigen cross-presentation and XCR1 expression define human $CD11_c+CD141+$ cells as homologues of mouse $CD8+$ dendritic cells," J Exp Med. 207(6):1273-81 (2010).
Biragyn et al., "Genetic fusion of chemokines to a self tumor antigen induces protective, T-cell dependent antitumor immunity," Nat Biotechnol. 17(3):253-8 (1999).
Bordon, "Chemokines: a class apart—uncovering a role for the C-chemokine," Nature Reviews Immunology. vol. 10 (2010) (1 page).
Chen et al., "Programmed cell death of dendritic cells in immune regulation," Immunol Rev. 236:11-27 (2010).
Yoshida et al., "Molecular cloning of mXCR1, the murine SCM-1/lymphotactin receptor," FEBS Lett. 458(1):37-40 (1999).

\* cited by examiner

SEQUENCE LISTING

<160> NUMBER OF SEQ ID NOS: 19

<210> SEQ ID NO 1
<211> LENGTH: 114
<212> TYPE: PRT
<213> ORGANISM: Homo sapiens

<400> SEQUENCE: 1

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser Asp Lys Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly

<210> SEQ ID NO 2
<211> LENGTH: 114
<212> TYPE: PRT
<213> ORGANISM: Mus musculus

<400> SEQUENCE: 2

Met Arg Leu Leu Leu Leu Thr Phe Leu Gly Val Cys Cys Leu Thr Pro
1               5                   10                  15

Trp Val Val Glu Gly Val Gly Thr Glu Val Leu Glu Glu Ser Ser Cys
                20                  25                  30

Val Asn Leu Gln Thr Gln Arg Leu Pro Val Gln Lys Ile Lys Thr Tyr
            35                  40                  45

Ile Ile Trp Glu Gly Ala Met Arg Ala Val Ile Phe Val Thr Lys Arg
    50                  55                  60

Gly Leu Lys Ile Cys Ala Asp Pro Glu Ala Lys Trp Val Lys Ala Ala
65                  70                  75                  80

Ile Lys Thr Val Asp Gly Arg Ala Ser Thr Arg Lys Asn Met Ala Glu
                85                  90                  95

Thr Val Pro Thr Gly Ala Gln Arg Ser Thr Ser Thr Ala Ile Thr Leu
            100                 105                 110

Thr Gly

<210> SEQ ID NO 3
<211> LENGTH: 114
<212> TYPE: PRT
<213> ORGANISM: Rattus norvegicus

<400> SEQUENCE: 3

Met Arg Leu Leu Leu Leu Thr Phe Leu Gly Val Cys Cys Phe Ala Ala
1               5                   10                  15

Trp Val Val Glu Gly Val Gly Thr Glu Val Leu Gln Glu Ser Ile Cys
                20                  25                  30

Val Ser Leu Arg Thr Gln Arg Leu Pro Val Gln Lys Ile Lys Thr Tyr
            35                  40                  45

Thr Ile Lys Glu Gly Ala Met Arg Ala Val Ile Phe Val Thr Lys Arg
    50                  55                  60

Gly Leu Arg Ile Cys Ala Asp Pro Gln Ala Lys Trp Val Lys Thr Ala
65                  70                  75                  80

Ile Lys Thr Val Asp Gly Arg Ala Ser Ala Ser Lys Ser Lys Ala Glu
                85                  90                  95

Thr Ile Pro Thr Gln Ala Gln Arg Ser Ala Ser Thr Ala Val Thr Leu
            100                 105                 110

Thr Gly

<210> SEQ ID NO 4
<211> LENGTH: 114
<212> TYPE: PRT
<213> ORGANISM: Human herpesvirus 8

<400> SEQUENCE: 4

Met Trp Ser Met Cys Trp Val Leu Arg Ala His Leu Gly Leu Leu Phe
1               5                   10                  15

Trp Val Ala Val Ile Glu Leu Cys Ala Ala Ser Gly Pro Ala Thr Ile
            20                  25                  30

Met Ala Ser Asp Cys Cys Glu Asn Ser Leu Ser Ala Arg Leu Pro
        35                  40                  45

Pro Asp Lys Leu Ile Cys Gly Trp Tyr Trp Thr Ser Thr Val Tyr Cys
    50                  55                  60

Arg Gln Lys Ala Val Ile Phe Val Thr His Ser Gly Arg Lys Val Cys
65                  70                  75                  80

Gly Ser Pro Ala Lys Arg Arg Thr Arg Leu Leu Met Glu Lys His Thr
                85                  90                  95

Glu Ile Pro Leu Ala Lys Arg Val Ala Leu Arg Ala Gly Lys Gly Leu
            100                 105                 110

Cys Pro

<210> SEQ ID NO 5
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: Xaa
<222> LOCATION: (1)..(1)
<223> OTHER INFORMATION: Xaa = S or N
<220> FEATURE:
<221> NAME/KEY: Xaa
<222> LOCATION: (3)..(3)
<223> OTHER INFORMATION: Xaa = any or no amino acid
<220> FEATURE:
<221> NAME/KEY: Xaa
<222> LOCATION: (4)..(4)
<223> OTHER INFORMATION: Xaa = T or S
<220> FEATURE:
<221> NAME/KEY: Xaa
<222> LOCATION: (5)..(5)
<223> OTHER INFORMATION: Xaa = Q or A
<220> FEATURE:
<221> NAME/KEY: Xaa
<222> LOCATION: (9)..(9)
<223> OTHER INFORMATION: Xaa = V or P
<220> FEATURE:
<221> NAME/KEY: Xaa
<222> LOCATION: (10)..(10)
<223> OTHER INFORMATION: Xaa = any amino acid
<220> FEATURE:
<221> NAME/KEY: Xaa
<222> LOCATION: (11)..(11)
<223> OTHER INFORMATION: Xaa = K or R
<220> FEATURE:
<221> NAME/KEY: Xaa
<222> LOCATION: (12)..(12)
<223> OTHER INFORMATION: Xaa = I or L
<220> FEATURE:
<221> NAME/KEY: Xaa
<222> LOCATION: (13)..(13)
<223> OTHER INFORMATION: Xaa = K or I
<220> FEATURE:
<221> NAME/KEY: Xaa
<222> LOCATION: (14)..(14)
<223> OTHER INFORMATION: Xaa = any or no amino acid
<220> FEATURE:
<221> NAME/KEY: Xaa
<222> LOCATION: (15)..(15)
<223> OTHER INFORMATION: Xaa = T or G
<220> FEATURE:
<221> NAME/KEY: Xaa

```
<222> LOCATION: (16)..(16)
<223> OTHER INFORMATION: Xaa = any or no amino acid

<400> SEQUENCE: 5

Xaa Leu Xaa Xaa Xaa Arg Leu Pro Xaa Xaa Xaa Xaa Xaa Xaa Xaa
1               5                   10                  15

Tyr

<210> SEQ ID NO 6
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: Xaa
<222> LOCATION: (1)..(1)
<223> OTHER INFORMATION: Xaa = R or K
<220> FEATURE:
<221> NAME/KEY: Xaa
<222> LOCATION: (6)..(6)
<223> OTHER INFORMATION: Xaa = I or V
<220> FEATURE:
<221> NAME/KEY: Xaa
<222> LOCATION: (8)..(8)
<223> OTHER INFORMATION: Xaa = K or H
<220> FEATURE:
<221> NAME/KEY: Xaa
<222> LOCATION: (9)..(9)
<223> OTHER INFORMATION: Xaa = R or S
<220> FEATURE:
<221> NAME/KEY: Xaa
<222> LOCATION: (11)..(11)
<223> OTHER INFORMATION: Xaa = L or R
<220> FEATURE:
<221> NAME/KEY: Xaa
<222> LOCATION: (12)..(12)
<223> OTHER INFORMATION: Xaa = K or R
<220> FEATURE:
<221> NAME/KEY: Xaa
<222> LOCATION: (13)..(13)
<223> OTHER INFORMATION: Xaa = I or V
<220> FEATURE:
<221> NAME/KEY: Xaa
<222> LOCATION: (15)..(15)
<223> OTHER INFORMATION: Xaa =  A or G
<220> FEATURE:
<221> NAME/KEY: Xaa
<222> LOCATION: (16)..(16)
<223> OTHER INFORMATION: Xaa =  D or S

<400> SEQUENCE: 6

Xaa Ala Val Ile Phe Xaa Thr Xaa Xaa Gly Xaa Xaa Xaa Cys Xaa Xaa
1               5                   10                  15

Pro

<210> SEQ ID NO 7
<211> LENGTH: 58
<212> TYPE: PRT
<213> ORGANISM: Artificial Sequence
<220> FEATURE:
<223> OTHER INFORMATION: Synthetic Construct
<220> FEATURE:
<221> NAME/KEY: Xaa
<222> LOCATION: (1)..(57)
<223> OTHER INFORMATION: Xaa = any or no amino acid

<400> SEQUENCE: 7

Xaa Gly Xaa Xaa Xaa Xaa Xaa Xaa Xaa Xaa Xaa Cys Xaa Xaa Xaa
1               5                   10                  15

Leu Xaa Xaa Xaa Arg Leu Pro Xaa Xaa Xaa Xaa Xaa Xaa Xaa Tyr
```

```
            20                  25                  30
Xaa Xaa Xaa Xaa Xaa Xaa Xaa Xaa Xaa Ala Val Ile Phe Xaa Thr
        35                  40                  45

Xaa Xaa Gly Xaa Xaa Xaa Cys Xaa Xaa Pro
    50                  55

<210> SEQ ID NO 8
<211> LENGTH: 58
<212> TYPE: PRT
<213> ORGANISM: Artificial Sequence
<220> FEATURE:
<223> OTHER INFORMATION: Synthetic Construct
<220> FEATURE:
<221> NAME/KEY: Xaa
<222> LOCATION: (1)..(1)
<223> OTHER INFORMATION: Xaa = V or S
<220> FEATURE:
<221> NAME/KEY: Xaa
<222> LOCATION: (3)..(3)
<223> OTHER INFORMATION: Xaa = any or no amino acid
<220> FEATURE:
<221> NAME/KEY: Xaa
<222> LOCATION: (4)..(4)
<223> OTHER INFORMATION: Xaa = E or A
<220> FEATURE:
<221> NAME/KEY: Xaa
<222> LOCATION: (5)..(5)
<223> OTHER INFORMATION: Xaa = V or T
<220> FEATURE:
<221> NAME/KEY: Xaa
<222> LOCATION: (6)..(12)
<223> OTHER INFORMATION: Xaa = any or no amino acid
<220> FEATURE:
<221> NAME/KEY: Xaa
<222> LOCATION: (14)..(14)
<223> OTHER INFORMATION: Xaa = V or E
<220> FEATURE:
<221> NAME/KEY: Xaa
<222> LOCATION: (15)..(15)
<223> OTHER INFORMATION: Xaa = any or no amino acid
<220> FEATURE:
<221> NAME/KEY: Xaa
<222> LOCATION: (16)..(16)
<223> OTHER INFORMATION: Xaa = S or N
<220> FEATURE:
<221> NAME/KEY: Xaa
<222> LOCATION: (18)..(18)
<223> OTHER INFORMATION: Xaa = any or no amino acid
<220> FEATURE:
<221> NAME/KEY: Xaa
<222> LOCATION: (19)..(19)
<223> OTHER INFORMATION: Xaa = T or S
<220> FEATURE:
<221> NAME/KEY: Xaa
<222> LOCATION: (20)..(20)
<223> OTHER INFORMATION: Xaa = Q or A
<220> FEATURE:
<221> NAME/KEY: Xaa
<222> LOCATION: (24)..(24)
<223> OTHER INFORMATION: Xaa = V or P
<220> FEATURE:
<221> NAME/KEY: Xaa
<222> LOCATION: (25)..(25)
<223> OTHER INFORMATION: Xaa = any or no amino acid
<220> FEATURE:
<221> NAME/KEY: Xaa
<222> LOCATION: (26)..(26)
<223> OTHER INFORMATION: Xaa = K or R
<220> FEATURE:
<221> NAME/KEY: Xaa
<222> LOCATION: (27)..(27)
<223> OTHER INFORMATION: Xaa = I or L
<220> FEATURE:
<221> NAME/KEY: Xaa
<222> LOCATION: (28)..(28)
<223> OTHER INFORMATION: Xaa = K or I
```

```
<220> FEATURE:
<221> NAME/KEY: Xaa
<222> LOCATION: (29)..(29)
<223> OTHER INFORMATION: Xaa = any or no amino acid
<220> FEATURE:
<221> NAME/KEY: Xaa
<222> LOCATION: (30)..(30)
<223> OTHER INFORMATION: Xaa = T or G
<220> FEATURE:
<221> NAME/KEY: Xaa
<222> LOCATION: (31)..(31)
<223> OTHER INFORMATION: Xaa = any or no amino acid
<220> FEATURE:
<221> NAME/KEY: Xaa
<222> LOCATION: (33)..(33)
<223> OTHER INFORMATION: Xaa = any or no amino acid
<220> FEATURE:
<221> NAME/KEY: Xaa
<222> LOCATION: (34)..(34)
<223> OTHER INFORMATION: Xaa =  I or T
<220> FEATURE:
<221> NAME/KEY: Xaa
<222> LOCATION: (35)..(35)
<223> OTHER INFORMATION: Xaa = any or no amino acid
<220> FEATURE:
<221> NAME/KEY: Xaa
<222> LOCATION: (36)..(36)
<223> OTHER INFORMATION: Xaa = E or T
<220> FEATURE:
<221> NAME/KEY: Xaa
<222> LOCATION: (37)..(37)
<223> OTHER INFORMATION: Xaa = G or V
<220> FEATURE:
<221> NAME/KEY: Xaa
<222> LOCATION: (38)..(41)
<223> OTHER INFORMATION: Xaa = any or no amino acid
<220> FEATURE:
<221> NAME/KEY: Xaa
<222> LOCATION: (42)..(42)
<223> OTHER INFORMATION: Xaa = R or K
<220> FEATURE:
<221> NAME/KEY: Xaa
<222> LOCATION: (47)..(47)
<223> OTHER INFORMATION: Xaa = V or I
<220> FEATURE:
<221> NAME/KEY: Xaa
<222> LOCATION: (49)..(49)
<223> OTHER INFORMATION: Xaa = K or H
<220> FEATURE:
<221> NAME/KEY: Xaa
<222> LOCATION: (50)..(50)
<223> OTHER INFORMATION: Xaa = R or S
<220> FEATURE:
<221> NAME/KEY: Xaa
<222> LOCATION: (52)..(52)
<223> OTHER INFORMATION: Xaa = L or R
<220> FEATURE:
<221> NAME/KEY: Xaa
<222> LOCATION: (53)..(53)
<223> OTHER INFORMATION: Xaa = K or R
<220> FEATURE:
<221> NAME/KEY: Xaa
<222> LOCATION: (54)..(54)
<223> OTHER INFORMATION: Xaa = any or no amino acid
<220> FEATURE:
<221> NAME/KEY: Xaa
<222> LOCATION: (56)..(56)
<223> OTHER INFORMATION: Xaa = A or G
<220> FEATURE:
<221> NAME/KEY: Xaa
<222> LOCATION: (57)..(57)
<223> OTHER INFORMATION: Xaa = D or S

<400> SEQUENCE: 8

Xaa Gly Xaa Xaa Xaa Xaa Xaa Xaa Xaa Xaa Xaa Xaa Cys Xaa Xaa Xaa
1               5                   10                  15

Leu Xaa Xaa Xaa Arg Leu Pro Xaa Xaa Xaa Xaa Xaa Xaa Xaa Xaa Tyr
```

```
                20                  25                  30
Xaa Xaa Xaa Xaa Xaa Xaa Xaa Xaa Xaa Xaa Ala Val Ile Phe Xaa Thr
        35                  40                  45

Xaa Xaa Gly Xaa Xaa Xaa Cys Xaa Xaa Pro
    50                  55

<210> SEQ ID NO 9
<211> LENGTH: 93
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (46)..(47)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (57)..(63)
<223> OTHER INFORMATION: Xaa can be any naturally occurring amino acid
<220> FEATURE:
<221> NAME/KEY: misc_feature
<222> LOCATION: (65)..(75)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
```

```
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(86)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 9

Val Gly Xaa Glu Val Xaa Xaa Xaa Xaa Cys Val Xaa Leu Xaa Thr
 1               5                  10                  15

Gln Arg Leu Pro Val Xaa Xaa Ile Lys Thr Tyr Xaa Ile Xaa Glu Gly
                20                  25                  30

Xaa Xaa Arg Ala Val Ile Phe Xaa Thr Lys Arg Gly Leu Xaa Xaa Cys
            35                  40                  45

Ala Asp Pro Xaa Ala Xaa Trp Val Xaa Xaa Xaa Xaa Xaa Xaa Xaa Asp
        50                  55                  60

Xaa Xaa Xaa Xaa Xaa Xaa Xaa Xaa Xaa Xaa Xaa Thr Xaa Pro Thr Xaa
65                  70                  75                  80

Xaa Gln Xaa Ser Xaa Xaa Thr Ala Xaa Thr Leu Thr Gly
                85                  90

<210> SEQ ID NO 10
<211> LENGTH: 93
<212> TYPE: PRT
<213> ORGANISM: Artificial Sequence
<220> FEATURE:
<223> OTHER INFORMATION: Synthetic Construct
<220> FEATURE:
<221> NAME/KEY: Xaa
<222> LOCATION: (3)..(3)
<223> OTHER INFORMATION: Xaa = T or S
<220> FEATURE:
<221> NAME/KEY: Xaa
<222> LOCATION: (6)..(6)
<223> OTHER INFORMATION: Xaa = L or S
<220> FEATURE:
<221> NAME/KEY: Xaa
<222> LOCATION: (7)..(7)
<223> OTHER INFORMATION: Xaa = any or no amino acid
<220> FEATURE:
<221> NAME/KEY: Xaa
<222> LOCATION: (8)..(8)
<223> OTHER INFORMATION: Xaa = E or K
<220> FEATURE:
<221> NAME/KEY: Xaa
<222> LOCATION: (9)..(9)
<223> OTHER INFORMATION: Xaa = S or R
<220> FEATURE:
<221> NAME/KEY: Xaa
<222> LOCATION: (10)..(10)
<223> OTHER INFORMATION: Xaa = any or no amino acid
<220> FEATURE:
<221> NAME/KEY: Xaa
<222> LOCATION: (13)..(13)
<223> OTHER INFORMATION: Xaa = S or N
<220> FEATURE:
<221> NAME/KEY: Xaa
<222> LOCATION: (15)..(15)
<223> OTHER INFORMATION: Xaa = any or no amino acid
<220> FEATURE:
<221> NAME/KEY: Xaa
<222> LOCATION: (22)..(22)
<223> OTHER INFORMATION: Xaa = Q or S
<220> FEATURE:
<221> NAME/KEY: Xaa
<222> LOCATION: (23)..(23)
```

```
<223> OTHER INFORMATION: Xaa = K or R
<220> FEATURE:
<221> NAME/KEY: Xaa
<222> LOCATION: (28)..(28)
<223> OTHER INFORMATION: Xaa = T or I
<220> FEATURE:
<221> NAME/KEY: Xaa
<222> LOCATION: (30)..(30)
<223> OTHER INFORMATION: Xaa = any or no amino acid
<220> FEATURE:
<221> NAME/KEY: Xaa
<222> LOCATION: (33)..(33)
<223> OTHER INFORMATION: Xaa = A or S
<220> FEATURE:
<221> NAME/KEY: Xaa
<222> LOCATION: (34)..(34)
<223> OTHER INFORMATION: Xaa = M or L
<220> FEATURE:
<221> NAME/KEY: Xaa
<222> LOCATION: (40)..(40)
<223> OTHER INFORMATION: Xaa = V or I
<220> FEATURE:
<221> NAME/KEY: Xaa
<222> LOCATION: (46)..(46)
<223> OTHER INFORMATION: Xaa = K or R
<220> FEATURE:
<221> NAME/KEY: Xaa
<222> LOCATION: (47)..(47)
<223> OTHER INFORMATION: Xaa = I or V
<220> FEATURE:
<221> NAME/KEY: Xaa
<222> LOCATION: (52)..(52)
<223> OTHER INFORMATION: Xaa = Q or E
<220> FEATURE:
<221> NAME/KEY: Xaa
<222> LOCATION: (54)..(54)
<223> OTHER INFORMATION: Xaa = K or T
<220> FEATURE:
<221> NAME/KEY: Xaa
<222> LOCATION: (57)..(57)
<223> OTHER INFORMATION: Xaa = K or R
<220> FEATURE:
<221> NAME/KEY: Xaa
<222> LOCATION: (58)..(58)
<223> OTHER INFORMATION: Xaa = any or no amino acid
<220> FEATURE:
<221> NAME/KEY: Xaa
<222> LOCATION: (59)..(59)
<223> OTHER INFORMATION: Xaa = A or V
<220> FEATURE:
<221> NAME/KEY: Xaa
<222> LOCATION: (60)..(60)
<223> OTHER INFORMATION: Xaa = I or V
<220> FEATURE:
<221> NAME/KEY: Xaa
<222> LOCATION: (61)..(61)
<223> OTHER INFORMATION: Xaa = K or R
<220> FEATURE:
<221> NAME/KEY: Xaa
<222> LOCATION: (62)..(62)
<223> OTHER INFORMATION: Xaa = T or S
<220> FEATURE:
<221> NAME/KEY: Xaa
<222> LOCATION: (63)..(63)
<223> OTHER INFORMATION: Xaa = V or M
<220> FEATURE:
<221> NAME/KEY: Xaa
<222> LOCATION: (65)..(65)
<223> OTHER INFORMATION: Xaa = G or R
<220> FEATURE:
<221> NAME/KEY: Xaa
<222> LOCATION: (66)..(66)
<223> OTHER INFORMATION: Xaa = R or K
<220> FEATURE:
<221> NAME/KEY: Xaa
<222> LOCATION: (67)..(67)
<223> OTHER INFORMATION: Xaa = A or S
<220> FEATURE:
<221> NAME/KEY: Xaa
```

<222> LOCATION: (68)..(68)
<223> OTHER INFORMATION: Xaa = S or N
<220> FEATURE:
<221> NAME/KEY: Xaa
<222> LOCATION: (69)..(69)
<223> OTHER INFORMATION: Xaa = T or A
<220> FEATURE:
<221> NAME/KEY: Xaa
<222> LOCATION: (70)..(70)
<223> OTHER INFORMATION: Xaa = R or S
<220> FEATURE:
<221> NAME/KEY: Xaa
<222> LOCATION: (71)..(71)
<223> OTHER INFORMATION: Xaa = K or N
<220> FEATURE:
<221> NAME/KEY: Xaa
<222> LOCATION: (72)..(72)
<223> OTHER INFORMATION: Xaa = N or S
<220> FEATURE:
<221> NAME/KEY: Xaa
<222> LOCATION: (73)..(73)
<223> OTHER INFORMATION: Xaa = M or K
<220> FEATURE:
<221> NAME/KEY: Xaa
<222> LOCATION: (74)..(74)
<223> OTHER INFORMATION: Xaa = A or I
<220> FEATURE:
<221> NAME/KEY: Xaa
<222> LOCATION: (75)..(75)
<223> OTHER INFORMATION: Xaa = E or Q
<220> FEATURE:
<221> NAME/KEY: Xaa
<222> LOCATION: (77)..(77)
<223> OTHER INFORMATION: Xaa = any or no amino acid
<220> FEATURE:
<221> NAME/KEY: Xaa
<222> LOCATION: (80)..(80)
<223> OTHER INFORMATION: Xaa = G or Q
<220> FEATURE:
<221> NAME/KEY: Xaa
<222> LOCATION: (81)..(81)
<223> OTHER INFORMATION: Xaa = A or T
<220> FEATURE:
<221> NAME/KEY: Xaa
<222> LOCATION: (83)..(83)
<223> OTHER INFORMATION: Xaa = R or Q
<220> FEATURE:
<221> NAME/KEY: Xaa
<222> LOCATION: (85)..(85)
<223> OTHER INFORMATION: Xaa = T or A
<220> FEATURE:
<221> NAME/KEY: Xaa
<222> LOCATION: (86)..(86)
<223> OTHER INFORMATION: Xaa = S or N
<220> FEATURE:
<221> NAME/KEY: Xaa
<222> LOCATION: (89)..(89)
<223> OTHER INFORMATION: Xaa = V or I

<400> SEQUENCE: 10

Val Gly Xaa Glu Val Xaa Xaa Xaa Xaa Cys Val Xaa Leu Xaa Thr
1               5                   10                  15

Gln Arg Leu Pro Val Xaa Xaa Ile Lys Thr Tyr Xaa Ile Xaa Glu Gly
            20                  25                  30

Xaa Xaa Arg Ala Val Ile Phe Xaa Thr Lys Arg Gly Leu Xaa Xaa Cys
        35                  40                  45

Ala Asp Pro Xaa Ala Xaa Trp Val Xaa Xaa Xaa Xaa Xaa Xaa Asp
50                  55                  60

Xaa Xaa Xaa Xaa Xaa Xaa Xaa Xaa Xaa Xaa Thr Xaa Pro Thr Xaa
65                  70                  75                  80

Xaa Gln Xaa Ser Xaa Xaa Thr Ala Xaa Thr Leu Thr Gly
            85                  90

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
tgcctgtgtt gatctcagca c                                    21

<210> SEQ ID NO 12
<211> LENGTH: 19
<212> TYPE: DNA
<213> ORGANISM: Artificial Sequence
<220> FEATURE:
<223> OTHER INFORMATION: Synthetic Construct

<400> SEQUENCE: 12
cggtggatgg tcatgatgg                                       19

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
cgctcggtga ccctagtctt t                                    21

<210> SEQ ID NO 14
<211> LENGTH: 21
<212> TYPE: DNA
<213> ORGANISM: Artificial Sequence
<220> FEATURE:
<223> OTHER INFORMATION: Synthetic Construct

<400> SEQUENCE: 14
ttcagtatgt tcggcttccc a                                    21

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Ser Ile Ile Asn Phe Glu Lys Leu
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Ile Ser Gln Ala Val His Ala Ala His Ala Glu Ile Asn Glu Ala Gly
1               5                   10                  15

Arg

<210> SEQ ID NO 17
<211> LENGTH: 333

<212> TYPE: PRT
<213> ORGANISM: Homo sapiens

<400> SEQUENCE: 17

Met Glu Ser Ser Gly Asn Pro Glu Ser Thr Thr Phe Phe Tyr Tyr Asp
1               5                   10                  15

Leu Gln Ser Gln Pro Cys Glu Asn Gln Ala Trp Val Phe Ala Thr Leu
            20                  25                  30

Ala Thr Thr Val Leu Tyr Cys Leu Val Phe Leu Leu Ser Leu Val Gly
        35                  40                  45

Asn Ser Leu Val Leu Trp Val Leu Val Lys Tyr Glu Ser Leu Glu Ser
    50                  55                  60

Leu Thr Asn Ile Phe Ile Leu Asn Leu Cys Leu Ser Asp Leu Val Phe
65                  70                  75                  80

Ala Cys Leu Leu Pro Val Trp Ile Ser Pro Tyr His Trp Gly Trp Val
                85                  90                  95

Leu Gly Asp Phe Leu Cys Lys Leu Leu Asn Met Ile Phe Ser Ile Ser
            100                 105                 110

Leu Tyr Ser Ser Ile Phe Phe Leu Thr Ile Met Thr Ile His Arg Tyr
        115                 120                 125

Leu Ser Val Val Ser Pro Leu Ser Thr Leu Arg Val Pro Thr Leu Arg
    130                 135                 140

Cys Arg Val Leu Val Thr Met Ala Val Trp Val Ala Ser Ile Leu Ser
145                 150                 155                 160

Ser Ile Leu Asp Thr Ile Phe His Lys Val Leu Ser Ser Gly Cys Asp
                165                 170                 175

Tyr Ser Glu Leu Thr Trp Tyr Leu Thr Ser Val Tyr Gln His Asn Leu
            180                 185                 190

Phe Phe Leu Leu Ser Leu Gly Ile Ile Leu Phe Cys Tyr Val Glu Ile
        195                 200                 205

Leu Arg Thr Leu Phe Arg Ser Arg Ser Lys Arg His Arg Thr Val
    210                 215                 220

Lys Leu Ile Phe Ala Ile Val Val Ala Tyr Phe Leu Ser Trp Gly Pro
225                 230                 235                 240

Tyr Asn Phe Thr Leu Phe Leu Gln Thr Leu Phe Arg Thr Gln Ile Ile
                245                 250                 255

Arg Ser Cys Glu Ala Lys Gln Gln Leu Glu Tyr Ala Leu Leu Ile Cys
            260                 265                 270

Arg Asn Leu Ala Phe Ser His Cys Cys Phe Asn Pro Val Leu Tyr Val
        275                 280                 285

Phe Val Gly Val Lys Phe Arg Thr His Leu Lys His Val Leu Arg Gln
    290                 295                 300

Phe Trp Phe Cys Arg Leu Gln Ala Pro Ser Pro Ala Ser Ile Pro His
305                 310                 315                 320

Ser Pro Gly Ala Phe Ala Tyr Glu Gly Ala Ser Phe Tyr
                325                 330

<210> SEQ ID NO 18
<211> LENGTH: 31
<212> TYPE: PRT
<213> ORGANISM: Artificial Sequence
<220> FEATURE:
<223> OTHER INFORMATION: Synthetic Construct

<400> SEQUENCE: 18

Met Glu Ser Ser Gly Asn Pro Glu Ser Thr Thr Phe Phe Tyr Tyr Asp

```
1               5                   10                  15
Leu Gln Ser Gln Pro Cys Glu Asn Gln Ala Trp Val Phe Ala Thr
            20                  25                  30

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Glu Gln Lys Leu Ile Ser Glu Glu Asp Leu
1               5                   10
```

SYSTEM FOR DELIVERY INTO XCR1 POSITIVE CELL AND USES THEREOF

CROSS REFERENCE TO RELATED APPLICATIONS

This application is the U.S. National Stage of International Application No. PCT/EP2008/009758, filed Nov. 19, 2008, which claims benefit of U.S. Provisional Application No. 61/013,263, filed Dec. 12, 2007, and European Patent Application No. 07022471.2, filed Nov. 20, 2007, each of which is hereby incorporated by reference.

The present invention relates to a delivery system suitable for delivering a substance into a XCR1 positive professional antigen-presenting cell, one or more nucleic acids coding for the same, a vector comprising the nucleic acid(s), a medicament comprising the delivery system or the one or more nucleic acid(s) and an adjuvant comprising XCL1 or a functionally active fragment thereof.

The immune system protects the body against pathogens and tumor cells by a variety of mechanisms. To function properly, it has to discriminate between "self" and "foreign" (pathogens/tumors). It detects and fights a variety of pathogens, including bacteria, viruses, parasites, fungi, and toxins. The immune systems of vertebrates such as humans consist of many types of proteins, cells, tissues, and organs, which interact in a dynamic network. As part of this complex immune response, the vertebrate immune system adapts over time to recognize particular pathogens more efficiently. The adaptation process creates immunological memory and allows a more effective protection during future encounters with these pathogens. Vaccination is based on this process of acquired immunity.

Disorders in the immune system can cause diseases. Immunodeficiency diseases occur when the immune system is less active than normal, resulting in recurring and life-threatening infections. In contrast, autoimmune diseases result from a hyperactive immune system attacking normal tissues as if they were foreign organisms. Common autoimmune diseases include rheumatoid arthritis, diabetes mellitus type 1, multiple sclerosis, and lupus erythematosus.

Dendritic cells (DCs) form part of the immune system. Their main function is to process antigen material and present it on the surface to other cells of the immune system, thus functioning as antigen-presenting cells.

T helper cells (also known as effector T cells or $T_h$ cells) are also an important member of the immune system in that they play a fundamental role in establishing and maximizing the capabilities of the immune system. $T_h$ cells are involved in activating and directing other immune cells, and are particularly important in the immune system. They are essential in determining B cell antibody class switching, in the activation and growth of cytotoxic T cells, and in maximizing bactericidal activity of phagocytes such as macrophages. It is this diversity in function and their role in influencing other cells that gives T helper cells their name. Proliferating helper T cells that develop into effector T cells differentiate into two major subtypes of cells known as $T_h1$ and $T_h2$ cells (also known as Type 1 and Type 2 helper T cells, respectively), wherein $T_h2$ cells mainly promote the humoral immune system (stimulation of B cells into proliferation, induction of B cell antibody class switching, and increase of antibody production), whereas $T_h1$ cells promote mainly the cellular immune system (maximization of killing efficacy of the macrophages and the proliferation of cytotoxic $CD8^+$ T cells). Depending on the nature of the invading pathogen, the immune system develops a Th1 or Th2 immune response. In the case of the Th1 immune response, the $CD8^+$ T cells show a strong tendency for differentiation into cytotoxic T cells. At the same time, both the $CD8^+$ and $CD4^+$ helper T cells of the Th1 immune response secrete large amounts of IFN-γ (and other Th1 cytokines/chemokines) and elicit the generation of antibodies predominantly of the IgG2a and IgG2b isotype in the mouse and predominantly of the IgG isotype in the human. The Th1 immune response is particularly effective for defending the body against viruses and (intracellular) bacteria. In the case of the Th2 immune response, helper T cells generate another pattern of cytokines (IL-4, IL-5, IL-13, and other). This pattern of cytokines promotes, among others, an IgG1/IgE response by B cells and plasma cells in the mouse and an IgE response in the human. This type of response is particularly effective against parasitic infections.

Currently available vaccines and adjuvant systems directed against live, attenuated, or inactivated pathogenic components mainly elicit an antibody immune response, but not an effective Th1 cytotoxic response (Steinman et al., 2007, Nature 449, 419-26). The induced antibodies bind to components of the pathogen and thus biologically inactivate it ("neutralizing antibodies"). However, there are a number of diseases, where neutralizing antibodies are not sufficient to protect from the disease or to control the disease and current vaccine technology is not effective. These are diseases which may require an effective Th1 immune response for containment and/or eradication of the infection. Examples are tuberculosis, malaria, leishmania, prion diseases, orthomyxoviruses and in particular influenza, hepatitis A, hepatitis B, human immunodeficiency virus (HIV) and other lentiviruses, cytomegalovirus, herpesviruses, papillomaviruses, bunyaviruses, caliciviruses, filoviruses, flaviviruses and in particular hepatitis C virus, papillomaviruses, paramyxoviruses, a variety of respiratory viruses, and other viruses which need for containment and eradication an effective Th1 immune response, and in particular a Th1 cytotoxic response. The development of a vaccination methodology inducing such an effective Th1 response is therefore highly desirable. Additionally, Th1/Th2 imbalance towards Th1 predominance is thought to play a significant role in the development of autoimmune diseases such as multiple sclerosis or rheumatoid arthritis. Therefore, regulation of Th1 response is a promising target in the prevention and treatment of autoimmune diseases. Furthermore, targeting Th1 response and the mechanism of "cross-presentation" (see below) is of paramount importance for the induction of a Th1 immune response against viral, bacterial, parasitic, and fungal pathogens, since dentritic cells most often do not become directly infected in the course of an infection. Without the development of a Th1 immune response, many viral, bacterial, parasitic, or fungal infections cannot be contained or eradicated in the human body. Additionally, in organ transplantation there is also a need to hinder a host's Th1 immune system from destroying the transplanted tissue and to make the recipient's immune system tolerant to the cellular components (antigens) of the donor.

Surprisingly, it has been found that cells playing a major role in Th1 response can be selectively targeted. It was found that chemokine (C motif) receptor 1 (XCR1) is present on the surface of professional antigen-presenting cell, particularly dendritic cells (DC), which can be used in order to selectively deliver substance into these cells. Targeted delivery of a substance to XCR1-bearing DC allows for the first time the induction of a potent Th1 immune reaction in mammals/humans. Current vaccines mainly address the Th2 antigen presentation pathway and mainly lead to the generation of Th2-type (neutralizing) antibodies and immune reactions. In particular, through targeting to XCR1-bearing DC, a Th1-type humoral and cellular (cytotoxic) immune reaction can be elicited to a given immunogen. It can be anticipated that NK cells, CD8$^+$ T cells, and Th1CD4+ T cells participate in this reaction, but other CD4$^+$ T cells may also contribute to this type of reaction. For the first time, an adjuvant, either alone or in combination with an immunogen or any pharmaceutical compound, can be selectively targeted to XCR1-bearing antigen-presenting cells (APC).

As detailed above, the developing immune system has to discriminate between "self" and "foreign" which occurs mainly in the thymus, where dendritic cells (DC) induce "central tolerance" by presenting self-antigens to developing thymocytes. Such self-antigens are endogenous proteins that are expressed by DC, and tissue-specific antigens that are ectopically expressed by thymic epithelial cells. The ability of the thymic DC to present exogenous antigens on MHC class II molecules, and to "cross-present" (see below) them on MHC class I molecules, allows thymic DC to mediate negative selection of both CD4$^+$ and CD8$^+$ thymocytes. This task may be assisted by DC that enter the thymus from peripheral tissues. Despite this process of thymic selection, autoreactive T cells can escape thymic selection and enter the periphery, and these must be held in check by mechanisms of peripheral tolerance that are elicited primarily by DCs in the spleen and other lymphatic tissues.

In the periphery, the immune system has to discriminate between harmless foreign or self-antigens on the one hand and dangerous (viral, bacterial, fungal, parasitic, toxin-like) antigens on the other hand. The antigen is taken up by the DC and broken down to peptides ("processed"). The resultant peptides are "presented" to T lymphocytes (T cells) in the context of the MHC class I or MHC class II. The CD4$^+$ subset of T cells recognizes the antigen in the context of MHC class II, the CD8$^+$ subset of T cells recognizes the antigen in the context of MHC class I. Concomitant with the uptake of antigen, the DC is capable of sensing through a large set of "danger signal" recognition receptors (e.g. toll-like receptors, NOD-like receptors), whether the antigen is of dangerous nature or whether it is harmless. The patterns recognized by the "danger signal" recognition receptors (also designated "pattern recognition receptors") are usually molecular structures that are unique to microorganisms. These can be cell wall components (e.g. lipopolysaccharide, peptidoglycan) or nucleic acid modifications (e.g. unmethylated CpG motifs) in case of microbes, or structural features and modifications that are unique to viral DNA or viral RNA (e.g. double-stranded RNA). Also cells dying from apoptosis in the body release molecules which are capable of triggering "danger signal" recognition receptors (e.g. High Mobility Group Protein B1, heat-shock proteins).

In the case of a harmless (self-)antigen, the DC do not "mature", instead they remain in an "immature" state. When the antigen is presented to CD4$^+$ and CD8$^+$ T cells by "immature APC", T cells become activated and proliferate extensively, but die within days due to a programmed limited life-span. Other T cells recognizing harmless (self-)antigen differentiate to "regulatory T cells", which are capable of suppressing an immune response upon repeated exposure to the same antigen using a variety of mechanisms (e.g. TGF-β, to CTLA-4, IL-10). As a result of T cell death and/or the T regulatory response, the immune system develops "peripheral tolerance" (non-responsiveness) to a given harmless (self-)antigen. Antigens that induce tolerance are "tolerogenic".

In the case of a dangerous antigen, the DC activates a different response program ("maturation"). The antigen is presented to CD4$^+$ and CD8$^+$ T cells, which simultaneously receive from the DC additional signals indicating the dangerous nature of the antigen. As a result, both T cell subsets become activated, expand extensively with a prolonged life span and develop to "effector T cells". These can be CD4$^+$ T cells providing "help" to other DC or B cells or other cells of the immune system, or can be even CD4$^+$ cytotoxic cells. Within the CD8$^+$ T cell subset, again T helper cells develop, but a large proportion of CD8$^+$ T cells become effector cells capable of eliminating the invading pathogen through secretion of IFN-γ and other soluble factors or through killing of infected body cells. As a result of the T cell help to B cells, antigen-specific B cells differentiate to plasma cells which secrete antibodies directed to the antigen (pathogen). These antibodies help to fight the pathogen through a number of mechanisms (e.g. neutralization, improved antigen uptake, opsonization, complement fixation).

A certain number of effector CD4$^+$ and CD8$^+$ T cells survive the acute phase of an immune response to a pathogen and become long-lived "memory T cells". Memory T cells and long-lived plasma cells orchestrate upon re-exposure to the same pathogen (antigen) a very fast immune response allowing the immune system to eliminate the pathogen (antigen) very effectively. This enhanced capability of the T-cell and B cell immune response upon re-exposure to the same pathogen is termed "immunity" and the antigens which induce immunity are "immunogenic".

In accordance with the above findings regarding the presence of chemokine (C motif) receptor 1 (XCR1) on the surface of professional antigen-presenting cells, particularly dendritic cells, and their role in the immune system, a first aspect of the present invention relates to a delivery system suitable for delivering a substance into a XCR1 positive professional antigen-presenting cell, the delivery system comprising i) a molecule binding to chemokine (C motif) receptor 1 (XCR1) and
ii) a substance to be delivered,
wherein substance is bound to the molecule.

The delivery system is particularly suitable for influencing the Th1 response, and optionally also the Th2 response, in the immune system.

XCR1 is a chemokine receptor and is so far the only member of the "C" sub-family of chemokine receptors. It is also known as GPR5 or CCXCR1. GPR5, cloned previously as an orphan G-protein coupled receptor, has been recognized first in the human and then in the mouse as a monospecific receptor for XCL1 (see below) and was accordingly referred to as XCR1. The expression of XCR1 in primary tissues was reported in the thymus, spleen, placenta, lung, lymph node, tonsil, lamina propria in Crohn's disease, and human melanocytic lesions by a variety of methods, without providing information on the cell types(s) expressing XCR1. More specific analyses claimed expression of XCR1 on splenic CD8$^+$ cells and NK1.1$^+$ CD3$^-$ cells, NK and T cell lines, CD3$^+$ T cells, T cells, B cells, and neutrophils, T cell line Jurkat, human fibroblast cell lines, primary fibroblast-like synoviocytes, synoviocytes and mononuclear cells in inflamed joints, murine CD8$^+$ T cells, and human neutrophils, B cells, T cells, NK cells, and monocytes. All of the latter reports on cell-type specific expression of XCR1 utilized PCR-analysis of total RNA, and the primers, which were used, were specific for XCR1 exon2 only, and thus did not span exon-intron-boundaries. Both strategies are prone to methodological errors (see below).

The natural ligand of XCR1 is XCL1, which is also known as ATAC, lymphotactin or SCM-1. It is the only member of the C family of chemokines. Activation-induced, T cell-derived, and chemokine-related cytokine (ATAC) was cloned in the human (Müller et al., 1995, Eur. J. Immunol. 25, 1744-48), and independently as lymphotactin (Kelner et al., 1994, Science 266, 1395-99) in the mouse and SCM-1 (Yoshida et al., 1995, FEBS Lett. 360, 155-9) in the human. According to the nomenclature on chemokines ATAC/lympho-tactin/SCM-1 is now designated "XCL1". XCL1 is secreted mainly by activated $CD8^+$ T-cells, Th1 $CD4^+$ T cells and by NK cells. In the human, a variant of XCL1 designated XCL2 has been described in which the amino acids aspartate and lysine in position 28 and 29 of the full length protein are exchanged for histidine and arginine, respectively (Yoshida et al., 1996, FEBS Lett. 395, 82-8), which may also be used for the present invention. An exemplary method to produce XCL1 in biologically active form is described in Example 8. Analogous methods may be used in order to produce other biologically active forms of XCL1, e.g. those of other species.

Originally, XCL1/lymphotactin/ATAC has been reported to induce (at best) weak chemotaxis on a variety of not well defined thymic and splenic populations (Kelner et al., 1994, Science 266, 1395-99), but these observations could not be reproduced by others (Müller et al., 1995, Eur. J. Immunol. 25, 1744-8; Bleul et al., 1996, J. Exp. Med. 184, 1101-9). Later, more specific reports about a chemotactic effect of XCL1 on T cells (Kennedy et al. 1995, J. Immunol. 155, 203-9) could not be reproduced by others (Mailer et al., 1995, Eur. J. Immunol. 25, 1744-8, Domer et al., 1997, J. Biol. Chem. 272, 8817-23). XCL1-induced chemotaxis on NK cells, on NKT cells, on B cells, neutrophils, and monocytes remained at best controversial. Chemotaxis on human monocyte-derived DC (Sozzani et al., 1997, J. Immunol. 159, 1993-2000, Lin et al., 1998, Eur. J. Immunol. 28, 4114-4122) and a murine DC cell line (Foti et al., 1999, Intern. Immunol. 11, 979-86) was specifically ruled out.

Based on detailed expression analysis of ATAC in the mouse, it could be demonstrated in the past that XCL1 (ATAC) is co-secreted in T cells and NK cells with IFN-γ, MIP-1α, MIP-1β, and RANTES. Apart from this observation, the biological function of the XCL1-XCR1 chemokine-chemokine receptor system in the immune system remained unclear and controversial.

Now it has been found that in mice $CD8^+$ positive DC seem to be the sole XCR1-expressing antigen-presenting cell population in the lymphoid system (see Example 1). To identify the population(s) expressing the mRNA for XCR1, we first isolated total RNA from the entire splenic cell populations and performed quantitative PCR (qPCR) after reverse-transcription of the RNA to cDNA. In the next step we isolated B cells, T cells, NK cells, or granulocytes, macrophages, obtained total RNA, and performed quantitative PCR. In all instances, we obtained significant signals. However, we also obtained quantitatively similar signals, when the total RNA was not reverse-transcribed to cDNA before being subjected to qPCR. At that time, the second exon of the murine XCR1 gene was regarded as the only existing exon, and therefore our PCR system (as was the case with all published PCR results on XCR1 expression in the literature) utilized primers spanning only this one exon. A thorough analysis of our experimental results suggested that the PCR-signals obtained with total RNA could be false positive signals resulting from genomic DNA typically contaminating total RNA preparations. To exclude the possibility of such an experimental error, we instead isolated mRNA instead of total RNA from entire splenic populations, as well as from B cells, T cells, NK cells, or granulocytes, as described below. In stark contrast to the results obtained with total RNA, we still obtained a (low) qPCR signal for XCR1 message with total spleen cells, but no signal with isolated B cells, T cells, NK cells, granulocytes, or macrophages (FIG. 1 and Table 1). After subsequent experiments indicated that the qPCR signal was associated with $CD11c^+$ splenic cells, we highly purified splenic $CD11c^+CD8^-$ and $CD11c^+CD8^+$ DC by flow cytometry (purity>95%), obtained mRNA from these populations, and subjected this mRNA to qPCR. The data obtained in this experiment clearly demonstrated that almost the entire signal for XCR1 mRNA resides in the $CD11c^+CD8^+$ DC population (FIG. 1), with only a small signal in $CD11c^+CD8^-$DC (which most likely results from contaminating $CD11c^+CD8^+$DC). At the same time, when $CD11c^+$ cells were depleted from total spleen cells, the qPCR signal disappeared linear to the degree of depletion of $CD11c^+$ cells.

Taken together, our results clearly demonstrated that the reports in the literature on the expression of XCR1 in T cells, B cells cells, NK cells, neutrophils, and monocytes (see above) were erroneous, since they were obtained with a single-exon PCR performed on total RNA (which contains small amounts of genomic DNA). Further, our data clearly demonstrated that XCR1 mRNA resides in $CD11c^+CD8^+$ DC. We thus could for the first time identify a cell population within the immune system, the $CD11c^+CD8^+$ DC, which specifically and exclusively expresses XCR1 mRNA. It can be assumed that there may exist other APC populations in other organs of the mammal/human body expressing the XCR1 receptor. These APC may not express the CD8 cell surface marker. These APC can be easily identified by sorting cells to high purify based on a variety of cell surface markers and subjecting them to qPCR for the mammal/human XCR1.

On the functional level, the inventors found that XCL1 selectively activates $CD8^+$DC but not $CD8^-$DC. $CD8^+$DC and $CD8^-$DC were flow-sorted to a high purity (>95%). They were then exposed to 100 nM of synthetic murine XCL1 and the activation of the DC cells was measured as an increase of intracellular $Ca^{2+}$ levels. The obtained results (see Example 2) demonstrated that only $CD8^+$DC (FIG. 2A), but not $CD8^-$DC (FIG. 2B), respond to murine XCL1 with a calcium signal and activation. These results indicate the presence of a functional XCR1 receptor on the surface of $CD8^+$DC. Furthermore, the data demonstrate that $CD8^+$DC, or any XCR1-positive cell, can be activated through the exposure to XCL1. These results thus show that XCL1 can be used as an adjuvant for XCR1-bearing mammal/human APC by improving their activation status and its antigen-presenting capabilities to NK cells or T cells. The results further imply that XCL1 can be used to deliver antigens, adjuvants, or any other compounds exclusively to XCR1-expressing DC through its specific binding to XCR1.

Furthermore, the inventors were able to show that XCL1 induces chemotaxis in $CD8^+$DC, but not in $CD8^-$DC, B cells, T cells, or NK cells (see Example 3). $CD11c^+$ cells were highly enriched from murine splenocyte populations by magnetic separation. When such a population was applied to the upper chamber of a transwell migration chamber system, the DC population consisted of around 25% $CD8^+$DC and 70% $CD8^-$DC, reflecting the natural relative frequency of these DC in the murine spleen. Without addition of a chemokine, only a very low unspecific background migration of the DC could be observed within 2 h (FIG. 3). Upon addition of murine XCL1 (1, 100, or 1000 ng/ml) into the lower chamber, cell migration from the upper chamber to the lower chamber could be observed in a dose-dependent fashion, with more than 30% of input $CD8^+$ DC migrating into the lower chamber at 100 ng/ml of XCL1. The only cells migrating to XCL1 were $CD8^+DC$, whereas $CD8^-DC$ only showed the same unspecific background migration as without a chemokine.

The addition of the chemokine CCL21 to the lower chamber, used as a positive control, demonstrated a chemotactic effect on both $CD8^+$ and $CD8^-$ DC, as expected. Addition of XCL1 to both the upper and lower chambers of the transwell system did not elicit any transmigration, demonstrating that XCL1 is not only a chemokinesis-inducing agent, but is a true chemoattractant. Analogous experiments performed with $CD11c^+$ cells highly enriched from peripheral lymph nodes demonstrated again that XCL1 is chemotactic only for $CD8^+DC$ but not for $CD8^-DC$ (FIG. 4). Analogous experiments performed with highly enriched B cells, T cells, or NK cells failed to demonstrate any specific chemotaxis to XCL1 (FIG. 5). These experiments demonstrated for the first time that XCL1 is a chemokine acting specifically on XCR1-expressing $CD8^+DC$, but not on other DC populations. From these results it can be anticipated that XCL1 acts as a chemokine on mammal/human XCR1-expressing APC. The results demonstrate that XCL1 can be used as an adjuvant for XCR1-expressing APC through its chemoattractive action. Additionally, it could be shown that XCL1 (ATAC) acts as an adjuvant in the induction of $CD8^+$ T cell cytotoxicity (see Example 9). The results further imply that XCL1 can be used to deliver antigens, adjuvants, or any other compounds exclusively to XCR1-expressing DC through its specific binding to XCR1.

Moreover, XCL1 facilitates cell uptake into $CD8^+DC$ dendritic cells (see Example 4). The murine pre-B cell line 300-19 was transfected with a vector coding for murine ATAC, resulting in the ATAC-expressing transfectant "muATAC/300-19". When ATAC KO mice were injected with $10 \times 10^6$ fluorescein-marked wild-type "wt/300-19" cells, a fluorescence signal could be detected in around 10% of splenic $CD8^+DC$ after 12 h, whereas no signal was observed in $CD8^-DC$. When the same number of fluorescein-marked muATAC/300-19 cells were injected, the signal recovered 12 h later was constantly and significantly higher in $CD8^+DC$, when compared to the injection of wt/300-19 (FIGS. 7 and 8). Also in this instance, no signal was observed in $CD8^-DC$. These results indicate that $CD8^+DC$ preferentially take up allogeneic cells. Further, the results demonstrate that XCL1 substantially improves the uptake of allogeneic cells into XCR1-bearing APC. From these results it can be anticipated that XCL1 also facilitates the uptake of XCL1-decorated (i.e. bearing XCL1-molecules on the outer surface) mammal/human syngeneic cells, either live or dead, specifically into XCR1-expressing mammal/human APC. From these results it can also be anticipated that XCL1 can specifically target any live or dead matter to XCR1-bearing APC, or at least improve its uptake into XCR1-bearing APC.

The concept of the present invention could be confirmed by showing XCL1 utilization during induction of tolerance or immunity in vivo (see Example 5). To determine whether the XCL1-XCR1 system is utilized in vivo during induction of immunity or tolerance, we used a well-established adoptive transfer system, in which transgenic DO11.10 $CD4^+$ T cells are transferred into syngeneic BALB/c mice. These transgenic T cells recognize a peptide derived from chicken ovalbumin (OVA) as antigen. Recipient mice were either challenged by injection of 100 μg OVA into footpads (tolerogenic stimulus), by injection of 100 μg OVA+ 10 μg of LPS into footpads (potent immunogenic stimulus, since LPS provides a "danger signal"), or by injection of 2 mg OVA intravenously (potent tolerogenic stimulus). In this system, the DO11.10 transgenic T cells recognize the antigen, become activated and expand. Under tolerogenic conditions the transgenic T cells have a limited life-span and die, whereas under immunogenic conditions the transgenic T cells develop to a significant degree into memory T cells. When the injected transgenic T cells were recovered from draining lymphatic tissue of the recipient mice after 14, 24, and 48 h, and subjected to expression analysis for murine XCL1 mRNA, it became apparent that in all circumstances the expression of XCL1 was very strongly and similarly upregulated (approx. by a factor of 30) upon OVA injection (Table 2). These data demonstrated that XCL1 can be highly expressed in $CD4^+$ T cells. They further showed that the XCL1-XCR1 functional axis is utilized both under strongly immunogenic as well as under strongly tolerogenic conditions. These data imply that targeting of an antigen to XCR1-bearing APC by means of XCL1 is a rational way to either induce strong immunity (when targeting the antigen together with an adjuvant/"danger signal") or to induce strong tolerance (when targeting the antigen without an adjuvant) in the mammal/human host.

In a further experiment, inventors were able to show XCL1-mediated, improved antigen recognition by $CD8^+T$ cells interacting with $CD8^+DC$ in vivo (see Example 6). In order to test adjuvant effects of XCL1 in vivo, we back-crossed C57BL/6 ATAC-KO mice to OT-I transgenic mice, which resulted in OT-I ATAC-KO mice. OT-I transgenic $CD8^+$ T cells recognize the OVA peptide SIINFEKL (SEQ ID NO: 15) as antigen. OT-I or OT-I ATAC-KO transgenic T cells were adoptively transferred into syngeneic ATAC-KO CD57BL/6 animals. Twenty four hours later all recipient mice were immunized by intravenous injection of OVA coupled to an anti-DEC-205 antibody ("DEC-205-OVA"). Under the conditions chosen, the antigen is preferentially taken up by $CD8^+DC$ in the spleen and preferentially cross-presented to $CD8^+T$ cells. Some mice received together with DEC-205-OVA an injection of an anti-CD40 antibody, which provides a "danger signal" to DC. Three days after injection of the antigen, the frequency of transgenic T cells was determined in the spleen (FIG. 9). Both under tolerogenic conditions (immunization with DEC-205-OVA without an "danger signal"), as well as under immunogenic conditions (immunization with DEC-205-OVA together with a CD40-mediated "danger signal"), the capability of OT-I T cells to secrete XLC1/ATAC very significantly increased the number of transgenic T cells 3 days after antigen exposure (FIG. 9). In addition, the capability of OT-I T cells to secrete XLC1/ATAC very significantly increased the ability of OT-I T cells to generate the cytokine IFN-γ (FIG. 10). Both the increase in cell number as well as the increase in IFN-γ production in the presence of XCL1 can be taken as evidence for the capacity of XCL1 to improve the interaction of $CD8^+DC$ with $CD8^+T$ cells upon antigen recognition. These data demonstrate that the XCL1/XCR1 axis is utilized by the immune system for induction of tolerance or for the induction of immunity. Further, these data imply that targeting of an antigen to XCR1-bearing APC by means of XCL 1 is a rational way to either induce strong immunity (when targeting the antigen together with an adjuvant/"danger signal") or to induce strong tolerance (when targeting the antigen without an adjuvant) in the mammal/human host. Under such therapeutic conditions the antigen would be delivered using XCL1 or an analogous vector system to deliver the antigen or antigen+"danger signal" directly to the XCR1-bearing mammal/human APC.

Moreover, inventors were able to generate a monoclonal antibody specific for the human XCR1 receptor (see Example 7). For this, BALB/c mice were immunized with a peptide representing the first 31 N-terminal amino acids of hXCR1 (hATACR), and the splenic cells were fused to the myeloma line P3X63Ag8.653. Obtained hybridomas were screened for secreting antibodies specifically recognizing the immunizing peptide in an ELISA assay. One such antibody, 6F8, which gave a specific reaction pattern in the ELISA, was chosen for further studies. The specificity of the antibody was tested by immunoprecipitation of XCR1 from 3 independent cell lines, which were transfected with the entire coding region of human XCR1. Monoclonal antibody 6F8 immoprecipitated the native human XCR1 receptor from all 3 transfectants, but did not react with the respective wild-type lines (FIG. 11). These experiments determined that we have generated a monoclonal antibody specific for human XCR1.

Finally, inventors were able to show that ATAC acts as an adjuvant in the induction of $CD8^+$ T cell cytotoxicity (see Example 9).

In accordance with the present invention the substance to be delivered (substance ii)) may be any suitable substance. For example the substance may be a protein, (poly)peptide, or small molecule. It may be a naturally occurring substance or part thereof or it may be a synthetic compound. Particularly preferred are substances having an effect on the immune system.

In one alternative, it could be desirable to modify the function of cross-presenting, XCR1-expressing APC. This modification could result in activation, suppression, or any other modification of the metabolism of the XCR1-bearing APC (e.g. leading to maturation or preventing maturation of the APC). This could be desirable in all conditions requiring defense against a foreign or autoimmune signal, and in other conditions, such as Alzheimer's disease. In such a case, the modifying substance ii) would be targeted to the XCR1-bearing APC using a targeting agent. The targeted pharmaceutical compound could be a chemical compound, a drug, a protein or peptide, a lipid, a carbohydrate, natural or modified (stabilized) DNA or RNA, siRNA, antisense nucleic acid, duplex DNA, single-stranded DNA, RNA in any form, including triplex, duplex or single-stranded RNA, anti-sense RNA, polynucleotide, oligonucleotide, single nucleotide or derivative thereof (see also below). The targeted compound could be an expression vector system or an engineered virus encoding a protein or peptide with modulating properties, as described above. It could be desirable that the encoded protein or peptide would be specifically expressed under the control of a XCR1-promoter to ensure specific expression in XCR1-bearing APC.

In another alternative, it could be desirable to specifically delete XCR1-expressing APC. This can be achieved by targeting a compound to XCR1-bearing APC, which directly or indirectly induces cell death in the XCR1-bearing APC. This could be desirable in all conditions including allergy, autoimmunity, and transplantation. Examples of such compounds are cytotoxic agents (e.g. methotrexate), toxins (diphtheria toxin, pseudomonas exotoxin), apoptosis-inducing agents (e.g. caspases), ribosome-inactivating agents (e.g. ricin, saponin, shiga toxin), inhibitors of DNA or RNA (RNA or DNA-cleaving agents), or inhibitors of protein synthesis (antisense DNA, antisense RNA, siRNA), and other inhibitors of cell metabolism (see also below). The proteinacious cell-inducing agent can be delivered directly to XCR1-bearing APC or by means of a nucleic acid-based expression vector system or an engineered virus, both preferably utilizing the XCR1-promoter for controlling the expression of the desired protein.

In still another alternative, it could be desirable to modify the function of cells interacting with XCR1-bearing APC. This could be achieved through an expression of a secreted peptide or protein (e.g. cytokine, chemokine, growth-factor, or hormone), or through expression of a receptor or ligand on the surface of XCR1-bearing APC (e.g. CD95L, ICOS-L, CD86, or other). To this end, DNA or RNA, or an expression vector system encoding such a peptide or protein, or a virus engineered to express such a peptide or protein, would be targeted to the XCR1-bearing APC. Preferably, the chosen expression system would be driven by a XCR1-promoter to ensure a specific expression in XCR1-bearing APC. The peptide or protein would contain a signal peptide to enable its expression as a soluble or transmembrane protein, after internalization of the nucleic acid or virus into the XCR1-bearing APC. The encoded soluble protein or peptide or cell surface receptor or ligand would be designed as to interact with a partner molecule on the surface of immune cells interacting with XCR1-bearing APC, such as $CD4^+Th1$ cells, $CD8^+T$ cells, NK cells, or other. In this way these interacting cells could be activated, suppressed in their activation, or even eliminated (e.g. through induction of apoptosis).

Furthermore, the delivery system could be used in order to detect XCR1-bearing APC for diagnostic purposes. For this, the substance may be any detectable compound such as a marker including e.g. a chromophore, a radioligand, etc.

Additionally, the substance could be modified in order to allow for isolation of XCR1-bearing APC, e.g. for further medical analysis or manipulation in vitro (e.g. loading with a pharmaceutical compound). For this, the substance may encompass a (fluorescent) label. Such labels include tags (His, FLAG, STREP, or c-myc) or components of the biotin-avidin system or digoxigenin-anti-digoxigenin system, allowing for separation by magnetic particles, flow sorting, etc.

In a preferred embodiment of the invention the substance ii) is an immunogen, an adjuvant, a drug, or a toxic agent.

An immunogen is an antigen that stimulates an immune response. Antigens are substances recognized by specific receptors on T cells (T-cell receptor) and B cells (B-cell receptor) within the immune system and are usually proteins or polysaccharides. This includes parts (coats, capsules, cell walls, flagella, fimbrae, and toxins) of bacteria, viruses, and other microorganisms. In general, lipids and nucleic acids are antigenic only when combined with proteins and polysaccharides. Non-microbial exogenous (non-self) antigens can include pollen, egg white, and proteins from transplanted tissues and organs or on the surface of transfused blood cells.

Antigens can be categorized as endogenous or exogenous. Endogenous antigens are proteins synthesized by the antigen-presenting cell (APC) itself ("self-proteins") or can be components of viral, bacterial, fungal, or parasitic pathogens, which have infected/invaded the APC. Endogenous antigens are presented in the context of MHC class I and II. Exogenous antigens are being taken up by pinocytosis, phagocytosis or receptor-mediated endocytosis. The internalized antigens thus become readily accessible to endosomal proteases and so can be presented by MHC class II molecules.

In addition, some cells can present exogenous antigens via MHC class I molecules, a process known as "cross-presentation". This pathway is of particular relevance in DC because they are the main cell population that can cross-present antigens in vivo, and this enables them to play a central role in tolerance induction and in antiviral, antibacterial, antifungal, and antiparasitic immunity. Within the mouse lymphoid DC, the CD8$^+$ DCs are the most efficient DC at phagocytosing dead cells and, consequently, at MHC class II presentation and MHC class I cross-presentation of exogenous cellular antigens. The CD8$^+$ mouse DCs are also the most efficient cross-presentating DC subset for exogenous soluble antigens, or antigens captured by C-type lectin receptors. It should be noted that the expression of the CD8 molecules is not a pre-requisite for cross-presentation. It can be anticipated, that both in the mouse and human systems, effectively cross-presenting, XCR1-bearing DC exist, which do not bear the CD8 marker.

Most soluble antigens taken up by DC from the extracellular space are presented in the context of MHC class II and thus induce a CD4/Th2 pattern of immune response (generation of Th2 CD4 T cell help, secretion of Th2 cytokines, generation of Th2-pattern antibodies, but little cytotoxic response). Intracellular antigens (including components of bacteria, fungi, viruses, and parasites which have infected the DC) are presented after processing in the context of MHC class I and MHC class II, and thus elicit a mixed Th1/Th2 response. Cross-presented antigen is presented in the context of MHC class I and elicits predominantly a Th1 response (generation of Th1 CD4 T cell help, production of Th1-pattern antibodies, secretion of IFN-γ and other Th1 cytokines, development of T cell cytotoxicity).

The antigen is presented by DC, cells which are highly specialized on antigen uptake, processing and presentation. There are a number of subtypes of DC. The main populations in the mouse are the plasmacytoid DC, CD11c$^+$CD8$^-$ DC (in short: "CD8$^-$DC", sometimes also referred to as CD4$^+$DC), CD11c$^+$CD8$^+$ DC (in short: "CD8$^+$DC"), the Langerhans' cells, double negative (DN) DC, and the interstitial DC. The role of plasmacytoid DC in antigen presentation and T cell priming is unclear, as in fact is their categorization as DC. There are lymphoid-organ-resident DC (CD8$^-$DC, CD8$^+$DC, and DN DC) and migratory DC (interstitial DC and Langerhans cells) (Villandagos et al., 2007, Nat. Rev. Immunol. 7, 543-55). All of these DC express the CD11c cell surface molecule. CD11c$^+$CD8$^-$DC represent about 1.6% and CD11c$^+$CD8$^+$DC 0.4% of total nucleated splenic cells.

Cross-presentation of antigen is also of central importance for the eradication of tumors in the body. Tumor cells and tumor antigens have to be taken up, processed, and presented by DC to elicit an anti-tumor immune response. Since the elimination of most tumors requires an effective cytotoxic Th1 T cell response, cross-presentation of tumor antigens is essential. Thus, for an effective anti-tumor response, cross-presenting DC play a preeminent role.

When foreign cells or organs are transplanted into human recipients, some cells or cell components are taken up, processed and presented by the host's DC to the host's immune system. The presentation of these foreign antigens can be expected to occur through the cross-presentation pathway and is known to elicit a strong Th1 immune response against the foreign tissue. Without a therapeutic intervention, the host's Th1 immune system will destroy the transplanted tissue ("host-versus-graft" (HVG)-reaction). There are a number of therapeutic regimens to control the HVG-reaction, but none of them is fully effective and none of them effectively induces tolerance against donor tissue components. Therefore there is a need to make the recipient's immune system tolerant to the cellular components (antigens) of the donor.

An adjuvant is an agent which modifies the effect of other agents while having few if any direct effects when given by itself. In pharmacology, adjuvants are drugs that have few or no pharmacological effects by themselves, but may increase the efficacy or potency of other drugs when given at the same time. In immunology an adjuvant is an agent which, while not having any specific antigenic effect in itself, may stimulate the immune system, increasing the response to a vaccine. The aluminum salts aluminum phosphate and aluminum hydroxide are the two most common adjuvants in human vaccines. Squalene is also used in some human vaccines and more vaccines with squalene and phosphate adjuvants are being tested on humans. Oil adjuvants are used in animal vaccines. Another market-approved adjuvant and carrier system is virosomes. During the last two decades a variety of technologies has been investigated to improve the widely used, but unfavorable adjuvants based on aluminum salts. These salts develop their effect by inducing a local inflammation, which is also the basis for the extended side-effect pattern of this adjuvant. By contrast, the adjuvant capabilities of virosomes are independent of any inflammatory reaction. Virosomes contain influenza virus-derived membrane-bound hemagglutinin and neuraminidase, which amplify fusogenic activity and therefore facilitate the uptake into antigen presenting cells (APC) and induce a natural antigen-processing pathway. The delivery of the antigen by virosomes to the immune system in an almost natural way and this may be a main reason why virosome-based vaccines stand out due to their excellent safety profile.

A drug is substance, in general exogenous, which has a specific effect on the function of a cell or organism. Often drugs are used in the treatment, cure, prevention, or diagnosis of disease or used to otherwise enhance physical or mental well-being. A medication or medicine is a drug taken to cure and/or ameliorate any symptoms of an illness or medical condition, or may be used as preventive medicine that has future benefits but does not treat any existing or pre-existing diseases or symptoms. Drugs are usually distinguished from endogenous biochemicals by being introduced from outside the organism.

A toxic agent or toxin is a substance or composition poisonous to living cells or organisms. Toxins are often proteins that are capable of causing disease on contact or absorption with body tissues by interacting with other proteins such as enzymes or cellular receptors. Toxins vary greatly in their severity, ranging from usually minor and acute (as in a bee sting) to almost immediately deadly (as in botulinum toxin). Biotoxins vary greatly in purpose and mechanism, and can be highly complex (the venom of the cone snail contains dozens of small proteins, each targeting a specific nerve channel or receptor), or relatively small protein.

In a more preferred embodiment of the invention the immunogen is a pathogen, a pathogen-derived antigen, an allergen, a tumor antigen or a tolerogen.

A pathogen or infectious agent is a biological agent, especially a living microorganism, which causes disease or illness to its host. Pathogen, according to this invention, means preferably a virus, bacterium and/or eukaryotic parasite. A pathogen-derived antigen is an antigen derived from a pathogen.

An allergen is a substance capable of producing hypersensitivity or an allergic reaction. Usually, it comprises a non-pathogen-derived antigen capable of stimulating a hypersensitivity reaction in individuals. Accordingly, a misguided reaction to foreign substances by the immune system is caused. The allergic reaction is misguided in that these foreign substances are usually harmless. Examples of allergens include pollens, dust mite, molds, danders, and certain foods.

A tumor antigen is a substance produced in tumor cells that triggers an immune response in the host. Tumor antigens are useful in identifying tumor cells and are potential candidates for use in cancer therapy. Normal proteins in the body are not antigenic because of self-tolerance. However, any protein produced in a tumor cell that has an abnormal structure due to mutation can act as a tumor antigen. Particularly, mutation of protooncogenes and tumor suppressors which lead to abnormal protein production are the cause of the tumor and thus such abnormal proteins are called tumor-specific antigens. Examples of tumor-specific antigens include the abnormal products of ras and p53 genes. In contrast, mutation of other genes unrelated to the tumor formation may lead to synthesis of abnormal proteins w which are called tumor-associated antigens. Proteins that are normally produced in low quantities but whose production is dramatically increased in tumor cells, trigger an immune response. An example of such a protein is the enzyme tyrosinase, which is required for melanin production. Normally tyrosinase is produced in minute quantities but its levels are very much elevated in melanoma cells. Oncofetal antigens are another important class of tumor antigens. Examples are alphafetoprotein (AFP) and carcinoembryonic antigen (CEA). These proteins are normally produced in the early stages of embryonic development and disappear by the time the immune system is fully developed. Thus self-tolerance does not develop against these antigens. Abnormal proteins are also produced by cells infected with oncoviruses, e.g. EBV and HPV. Cells infected by these viruses contain latent viral DNA which is transcribed and the resulting protein produces an immune response. In addition to proteins, other substances like cell surface glycolipids and glycoproteins may also have an abnormal structure in tumor cells and could thus be targets of the immune system.

A tolerogen is an immunogen that stimulates an immune response, but does not invoke an inflammatory immune defense reaction. It may be used to induce tolerance in the immune system against its components. Tolerance may occur due to central tolerance or peripheral tolerance. Central tolerance relates to tolerogens, wherein corresponding antigens have been exposed to T cells in the thymus leading to elimination of the specific T cells. Peripheral tolerance occurs when antigens are presented to T cells without appropriate additional "danger signal".

In a further more preferred embodiment of the invention the delivery system the toxic agent is a cytotoxin, an apoptosis-inducing agent, a ribosome-inactivating agent, a DNA- or RNA-cleaving agent, or an inhibitor of protein synthesis.

A cytotoxin is a substance having a direct toxic or destructive effect on certain cells of the body (usually those of a particular organ). Specific examples include nephrotoxins and neurotoxins.

Many cancer treatments use toxins or cytotoxins to kill the actively and rapidly dividing to cancer cells. An unfortunate side effect of this chemotherapy is that certain healthy and normal cells in the body such as hair follicles and bone marrow also actively divide and are also attacked by the cytotoxic agent, which limits the frequency of administration. Many chemotherapeutic drugs work by impairing mitosis, effectively targeting fast-dividing cells. Examples of common chemotherapeutics are alkylating agents (such as cisplatin, carboplatin and oxaliplatin), antimetabolites (e.g. those masquerading as purine ((azathioprine, mercaptopurine)) or pyrimidine), anthracyclines, plant alkaloids (such as vinca alkaloids and taxanes) and topoisomerase inhibitors (such as irinotecan, topotecan, amsacrine, etoposide, etoposide phosphate, and teniposide) affecting cell division or DNA synthesis. Further chemotherapeutics acting in a different manner include monoclonal antibodies (targeting tumor-specific antigens (such as trastuzumab (Herceptin), cetuximab, and rituximab) or blocking formation of new tumor vessels (such as bevacizumab (Avastin)) and the new tyrosine kinase inhibitors e.g. imatinib mesylate (Gleevec® or Glivec®), which directly targets a molecular abnormality in certain types of cancer (chronic myelogenous leukemia, gastrointestinal stromal tumors).

Functionally, the toxin may also be an apoptosis-inducing agent (an agent inducing programmed cell death of a cell such as gemcitabine, TNF-related apoptosis-inducing ligand (TRAIL) or an adamantyl group-containing retinoid-related compound), a ribosome-inactivating agent (a large group of toxic proteins widely distributed among the plant kingdom and inactivating ribosomes, e.g. by enzymatically attacking the 60S subunit of eukaryotic ribosomes and irreversibly modifying its large ribosomal RNA (rRNA) such as ricin, aviscumine, or a Shiga-like ribosome inactivating protein), a DNA- or RNA-cleaving agent (i.e. a DNA/RNA interactive compound that binds to and cleave DNA/RNA such as a 1,2,4-benzotriazine 1,4-dioxide, resveratrol, cisplatin or hammerhead ribozyme) or an inhibitor of protein synthesis (a compound which inhibits the synthesis of proteins by e.g. interruption of peptide-chain elongation, blocking site of ribosomes, misreading of the genetic code or prevention of the attachment of oligosaccharide side chains to glycoproteins such as antibiotics (e.g. anisomycin, chloramphenicol, streptomycin, tetracycline, neomycin or erythromycin) fusidic acid, diptheria toxin, ricin or cycloheximide.

In addition to the substance to be delivered (substance ii)) the delivery system comprises a molecule binding to chemokine (C motif) receptor 1 (XCR1) (molecule i). The molecule functions in that it selectively targets the XCR1 positive professional antigen-presenting cell and effects introduction of the substance to be delivered into this cell. Thereafter, the substance ii) may act in its intended manner depending on the nature of substance ii). Chemically, the molecule i) may be any suitable chemical compound; for example the molecule may be a protein, (poly)peptide, an antibody or fragment thereof or small molecule. Functionally, the molecule may be an agonist or an antagonist; however, a full or partial agonist is preferred. Without being bound to this theory it is assumed that upon binding of the molecule, particularly the agonist, to XCR1, the complex of ligand and XCR1 is internalized into the cell. From other members of the G protein coupled receptor family it is known that agonists tend to induce a higher level of internalization of the receptor than antagonists, accordingly agonists are preferred. Additionally, it should be understood that the ligand is intended to bind to a domain of the receptor capable of mediating incorporation of the substance to be delivered into the cell. It is assumed that the external domain(s) of the receptor is/are (a) particularly suitable domain(s) for mediating internalization of substance ii). Accordingly, it is assumed that ligands binding to this/these domain(s) are particularly suitable for the delivery system of the invention.

The amino acid sequence of human XCR1 is already known (NCBI; accession NP_001019815):

(SEQ ID NO: 17)

```
MESSGNPEST TFFYYDLQSQ PCENQAWVFA TLATTVLYCL

VFLLSLVGNS LVLWVLVKYE SLESLTNIFI LNLCLSDLVF

ACLLPVWISP YHWGWVLGDF LCKLLNMIFS ISLYSSIFFL

TIMTIHRYLS VVSPLSTLRV PTLRCRVLVT MAVWVASILS

SILDTIFHKV LSSGCDYSEL TWYLTSVYQH NLFFLLSLGI

ILFCYVEILR TLFRSRSKRR HRTVKLIFAI VVAYFLSWGP

YNFTLFLQTL FRTQIIRSCE AKQQLEYALL ICRNLAFSHC

CFNPVLYVFV GVKFRTHLKH VLRQFWFCRL QAPSPASIPH

SPGAFAYEGA SFY
```

However, the exact three-dimensional structure of XCR1 or other chemokine receptors is not yet known. Based on the analysis of the primary amino acid sequence, the closest homologous chemokine receptor of XCR1 is CCR5 with a 36% identity and 56% similarity on the amino acid level over a stretch of 321 residues. Several studies have presented detailed analysis of the domain structure and ligand binding sites of CCR5, and because of the significant homology between CCR5 and XCR1 the results of these studies may be used to predict structural characteristics of XCR1. One study analyzed conserved regions of several chemokines and derived precise prediction about the location of the intracellular, extracellular and transmembrane domains of CCR5 (Raport et al., 1996, J. Biol. Chem. 271, 17161-66). As the majority of these regions are also conserved in XCR1, it is reasonable to adopt the domain predictions of CCR5 and thus propose a domain structure for murine and human XCR1, as detailed in the table below. The residues of CCR5 important for ligand binding were studied in detail in another study (Zhou et al, 2000, Eur. J. Immunol. 30, 164-73) and it was proposed that while all extracellular domains may be involved in ligand binding, the N-terminus and the second extracellular loop (ECL2) are the main contributors. Based on these experiments it can be derived that the amino acids 1-34 and 166-191 of human XCR1 are the main binding sites for XCL1, and that the amino acids 89-103 and 251-271 make smaller contributions. Accordingly, molecules binding to these domains are likely to be suitable XCR1 ligands and this rationale may be used to search for and/or design suitable XCR1 ligands, e.g. by molecular modelling.

| extracellular domains | membrane domains | intracellular domains | murine XCR1 | human XCR1 |
|---|---|---|---|---|
| N-terminus | | | 1-30 | 1-34 |
| | transmembrane domain 1 (TM1) | | 31-55 | 35-59 |
| | | intracellular loop1 (ICL1) | 56-63 | 60-67 |
| | TM2 | | 64-84 | 68-88 |
| extracellular loop1 (ECL1) | | | 85-98 | 89-103 |
| | TM3 | | 99-117 | 104-122 |
| | | ICL2 | 118-138 | 123-143 |
| | TM4 | | 139-160 | 144-165 |
| ECL2 | | | 161-186 | 166-191 |
| | TM5 | | 187-205 | 192-210 |
| | | ICL3 | 206-220 | 211-225 |
| | TM6 | | 221-245 | 226-250 |
| ECL3 | | | 246-263 | 251-271 |
| | TM7 | | 264-282 | 272-290 |
| | | C-terminus | 283-322 | 291-333 |

Apart from binding to the XCR1 it should be understood that molecule i) should be capable of mediating incorporation (e.g. by receptor internalization or endocytosis or phagocytosis) of the substance ii) into the cell. The capability of a molecule i) of binding to XCR1 and mediating incorporation of a substance may be examined by standard methods, e.g. by labeling the molecule i) and tracing its fate (uptake into the XCR1-bearing cell), or by determining the level of XCR1 on the APC surface after binding of the molecule i) to XCR1 followed by an incubation period. The internalization of XCR1 can be tested on XCR1-bearing primary APC or alternatively on XCR1-transfectants (compare Example 7). The molecule i) to be tested can be labeled (e.g. using a radioactive compound or a fluorochrome, or a toxin, or a drug influencing the metabolism of XCR1-bearing cells) and reacted with the XCR1-bearing cell at a temperature, at which internalization of chemokine receptors occurs (typically higher than 7° C.) for an optimal time (typically more than 5 min) (Neel et al., 2005, Cyt. Growth Factor Rev. 16, 637-58). After a sufficient incubation period, the rate of XCR1 internalization can be determined either by measuring the amount of internalized molecule i) by optical methods (in the case of a fluorophore-marker) or by measuring the incorporated radioactivity (in case of a radioactive marker such as [$^{125}$I]-XCL1), or by assessing cell death (in case of a toxin), or by any other detection method suitable for the marker used. Alternatively, the rate of XCR1 internalization can be indirectly determined by comparing the level of XCR1 cell surface expression before and after binding of molecule i) to XCR1 using flow cytometry or any other assay (e.g. cell-ELISA) capable of determining the level of XCR1 on the cell surface. Alternatively, the transfected XCR1 receptor can be labeled (e.g. by a fluorophore or by using fluorescent fusion protein variants of XCR1 for transfection), so that the fate/internalization of the receptor can be assessed directly, e.g. by optical methods. All described approaches are adaptable to high-throughput screening systems. The described methods are well known to the skilled in the art (e.g. Colvin et al., 2004, J. Biol. Chem. 279, 30219-27; Sauty et al. 2001, J. Immunol. 167, 7084-93; Rose 2004, J. Biol. Chem. 279, 24372-86; Signoret et al., 2000, J. Cell. Biol. 151, 1281-94; and publications listed in Table 2 of Neel et al., 2005, Cyt. Growth Factor Rev. 16, 637-58). Alternatively, binding of molecule i) may also be studied using an activation test as detailed in Example 2 by measuring intracellular concentration of $Ca^{2+}$ or any other suitable metabolite of XCR1-induced cell activation. Alternatively, uptake of molecule i) can be measured according to the principles detailed in Example 4.

In a preferred embodiment of the invention the molecule i) is chemokine (C motif) ligand 1 (XCL1) or a functionally active variant thereof. As detailed above, XCL1 is the natural occurring ligand of XCR1. A naturally occurring variant thereof is XCL2 (see above), which may be also used. The three-dimensional structure of recombinant human XCL1 was determined by NMR spectroscopy. XCL1 was found to adopt a fold highly conserved between essentially all other chemokines, characterized by a disordered N-terminus, a three-stranded antiparallel β-sheet and a C-terminal α-Helix (the "classical" chemokine fold). As with other chemokines, the N-terminus seems to be required for XCL1 function. Thus it can be assumed that the binding of XCL1 to its receptor XCR1 is very similar to the receptor binding of other chemokines and may be described by a two-step model: In the first step, the main body of the chemokine specifically recognizes and binds the receptor, which induces a conformational change in the chemokine and a rearrangement of the flexible N-terminus. In the second step, the chemokine N-terminus interacts with the receptor and induces its activation, typically triggering the influx of calcium. Apart from the general similarity three structural characteristics were identified which are unique for XCL1; these comprise the number of disulfide bonds, the length of the C-terminus and the particular arrangement of an N-terminal domain. While the great majority of chemokines display two disulfide bonds, one of them is deleted in XCL1. This was proposed to destabilize the XCL1 structure because at near physiological conditions two conformational states can be detected: the conserved chemokine fold and a non-chemokine conformation. The biological implications of this structural heterogenity are unclear, but it has been proposed that the non-chemokine conformation does not bind the receptor. The second structural characteristic of ATAC is the presence of a large C-terminal extension (residues 73-93). The role of this unique C-terminus is not yet clear, and the functional consequences of its deletion are under dispute. Eight potential glycosylation sites have been found in the extended C-terminus, but an influence of glycosylation on the structure or function of XCL1 was not detected. Finally, the absence of the second disulfide bond results in a different orientation of the so called 30's loop, which is important for receptor interaction. In addition, this loop is shortened by two amino acids and decoupled from the N-terminus. The functional implications of this particular arrangement are not clear.

The amino acid sequences of XCL1 (ATAC) of several species (including human: SEQ ID NO: 1, GenBank accession P47992; mouse: SEQ ID NO: 2, GenBank accession P47993; and rat SEQ ID NO: 3, GenBank accession P51672) are known and are shown as SEQ ID NO: 1 to 3 (see below). Additionally, a specific XCLR1 agonist referred to as K4.1 HHV8 (SEQ ID NO: 4, GenBank accession AAB62672.1) (see below), which is a viral chemokine-like protein, is also known. Any of these naturally occurring XCR1 ligands or any other natural occurring XCR1 ligand may be used.

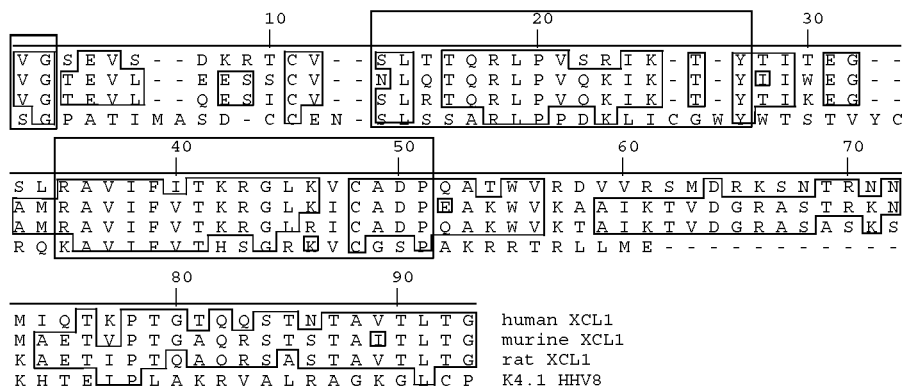

Alternatively, a functionally active variant of any naturally occurring XCL1 may be used. The term variant encompasses fragments, variants derived by one or more amino acid additions, deletions and/or substitutions and molecules, particularly proteins, comprising any naturally occurring XCL1 or part thereof, such as fusion proteins. The XCL1 portion of the fusion protein may be flanked by the amino acid residue(s) C-terminally, N-terminally, or C- and N-terminally.

The functionally active fragment is characterized by being derived from any natural occurring XCR1 ligand, particularly XCL1, especially those of SEQ ID NO:1 to 4, by one or more amino acid deletions. The deletion(s) may be C-terminally, N-terminally and/or internally. Preferably, the fragment is obtained by at most 1, 2, 3, 4, 5, 6, 7, 8, 9, 10, 20, 30, 40, 50 or 60, more preferably by at most 1, 2, 3, 4, 5, 6, 7, 8, 9, 10, 15, 20, 25 or 30, even more preferably at most 1, 2, 3, 4, 5, 6, 7, 8, 9, 10, 11, 12, 13, 14 or 15, still more preferably at most 1, 2, 3, 4, 5, 6, 7, 8, 9 or 10, most preferably 1, 2, 3, 4 or 5 amino acid deletion(s). The functionally active fragment of the invention is characterized by having a biological activity similar to that displayed by the ligand from which it is derived, including the ability to binding to XCR1 and mediate internalization of a substance ii). The fragment of the naturally occurring XCR1 ligand, particularly XCL1, especially those of SEQ ID NO:1 to 4, is functionally active in the context of the present invention, if the activity (binding as well as internalization) of the fragment amounts to at least 10%, preferably at least 25%, more preferably at least 50%, even more preferably at least 70%, still more preferably at least 80%, especially at least 90%, particularly at least 95%, most preferably at least 99% of the activity of the XCL1 without sequence alteration. These fragments may be designed or obtained in any desired length, including as small as about 18 to 50 amino acids in length.

The functionally active fragment of the naturally occurring XCR1 ligand, particularly XCL1, especially those of SEQ ID NO:1 to 4, may be also characterized by other structural features. Accordingly, in one preferred embodiment of the invention the functionally active fragments consists of at least 60%, preferably at least 70%, more preferably at least 80%, still more preferably at least 90%, even more preferably at least 95%, most preferably 99% of the amino acids of the XCR1 ligand of any of the SEQ ID NOS: 1 to 4. The functional active fragment as defined above may be derived from the peptide by one or more amino acid deletions. The deletions may be C-terminally, N-terminally and/or internally. The above sequence alignment of SEQ ID NOs: 1 to 4 shows domains of the naturally occurring ligands which seem to be conserved. In a preferred embodiment of the invention, these domains should be maintained in the fragment.

Conserved domains include those amino acids of the processed N-terminus (the processed N-terminus starting with amino acid 22 of non processed N-terminus) for SEQ ID NOs: 1 to 3 and with amino acid 27 for SEQ ID NO 4) at positions 1-2 (V/S G), 13-27 (S/N L X T/S Q/A R L P V/P X K/R I/L K/I X T/G X Y, X=any or no amino acid; SEQ ID NO: 5), 35 to 51 (R/K A V I F I/V T K/H R/S G L/R K/R I/V C A/G D/S P; SEQ ID NO: 6) and a disulfide bridge between cysteine residues at positions 11 and 48 (see also above alignment). A consensus sequence for the sequences of SEQ ID NO: 1 to 4 is XGXXXXXXXXXXCXXX-LXXXRLPXXXXXXXXXYXXXXXXXXXXAVIFX-TXXG-XXXCXXP (SEQ ID NO: 7) if only identical amino acids are considered and (V/S)GX(E/A)(V/T)XXXXXXXC(V/E)X(S/N)LX(T/S)(Q/A)RLP(V/P)X(K/R)(I/L)(K/I)-X(T/G)XYX(I/T)X(E/T)(G/V)XXXX(R/K)AVIF(V/I)T(K/H)(R/S)G(L/R)(K/R)XC(A/G)-(D/S)P (SEQ ID NO: 8) if identical amino acids and majority amino acids (i.e. amino acids which are present in 3 of the 4 sequences, the alternative amino acid is listed after the slash) are considered. A consensus sequence for the sequences of SEQ ID NO: 1 to 3 is VGXEVXXXXXCVXLXTQRLPVXXIKTYXIX-EGXXRAVIFXTKRGLXXCADPXAX-WVXXXXXXXDXXXXXXXXXXXTXPTXXQXSXX-TAXTLTG (SEQ ID NO: 9) if only identical amino acids are considered and VG(T/S)EV(L/S)X(E/K)(S/R)XCV-(S/N)LXTQRLPV(Q/S)(K/R)IKTY(T/I)IXEG(A/S)(M/L)RAVIF(V/I)TKRGL(K/R)(I/V)-CADP(Q/E)A(K/T)WV(K/R)X(A/V)(I/V)(K/R)(T/S)(V/M)D(G/R)(R/K)(A/S)(S/N)(T/A)-(R/S)(K/N)(N/S)(M/K)(A/I)(E/Q)TXPT(G/Q)(A/T)Q(R/Q)S(T/A)(S/N)TA(V/I)TLTG (SEQ ID NO: 10) if identical amino acids and majority amino acids (i.e. amino acids which are present in 2 of the 3 sequences, the alternative amino acid is listed after the slash) are considered. Accordingly, in a preferred delivery system of the invention the functionally active variant, preferably the functionally active fragment, of XCL1 comprises or consists of the sequence of any of SEQ ID NOs: 7 to 10, preferably of SEQ ID NOs: 8 to 10, more preferably of SEQ ID NOs: 9 or 10, especially of SEQ ID NO: 10.

Another preferred embodiment of the invention relates to a XCL1 variant as defined above, wherein the XCR1 ligand is a functionally active variant of an XCR1 ligand of any of the SEQ ID NOS: 1 to 4 and wherein the variant has at least 50% sequence identity to the XCR1 ligand of any of the SEQ ID NOS: 1 to 4. In a more preferred embodiment the functionally active variant has a sequence identity of at least 60%, preferably at least 70%, more preferably at least 80%, still more preferably at least 90%, even more preferably at least 95%, most preferably 99% to the antigen of any of the SEQ ID NOS: 1 to 4.

The percentage of sequence identity can be determined e.g. by sequence alignment. Methods of alignment of sequences for comparison are well known in the art. Various programs and alignment algorithms have been described e.g. in Smith and Waterman, Adv. Appl. Math. 2: 482, 1981 or Pearson and Lipman, Proc. Natl. Acad. Sci. U.S.A. 85: 2444-2448, 1988.

The NCBI Basic Local Alignment Search Tool (BLAST) (Altschul et al., J. Mol. Biol. 215: 403-410, 1990) is available from several sources, including the National Center for Biotechnology Information (NCBI, Bethesda, Md.) and on the Internet, for use in connection with the sequence analysis programs blastp, blastn, blastx, tblastn and tblastx. Variants of an antigen of any of the sequences of SEQ ID NOS: 1 to 4 are typically characterized using the NCBI Blast 2.0, gapped blastp set to default parameters. For comparisons of amino acid sequences of at least 35 amino acids, the Blast 2 sequences function is employed using the default BLOSUM62 matrix set to default parameters, (gap existence cost of 11, and a per residue gap cost of 1). When aligning short peptides (fewer than around 35 amino acids), the alignment is performed using the Blast 2 sequences function, employing the PAM30 matrix set to default parameters (open gap 9, extension gap 1 penalties). Methods for determining sequence identity over such short windows such as 15 amino acids or less are described at the website that is maintained by the National Center for Biotechnology Information in Bethesda, Md. (http://www.ncbi.nlm.nih.gov/BLAST/).

Alternatively, the alignment of multiple sequences may be performed using the MegAlign Sofware from DNAStar (Madison, Wis., USA) employing the ClustalV alignment algorithm (Higgins et al., 1992, Comput. Appl. Biosci. 8, 189-91). In the above alignment this software was used and set to the following default parameters: gap penalty 10, gap length penalty 10. Because of the very low homology, manual adjustments were necessary for the inclusion of SEQ ID NO 4 into the alignment.

The functional active variant is obtained by sequence alterations in the naturally occurring XCR1 ligand, wherein the XCR1 ligand with the sequence alterations retains a function of the unaltered XCR1 ligand, e.g. having a biological activity similar to that displayed by the naturally occurring XCR1 ligand, including the ability to binding to XCR1 and mediate internalization of a substance ii). Such sequence alterations can include, but are not limited to, conservative substitutions, deletions, mutations and insertions. These characteristics of the functional active variant can be assessed e.g. as detailed above.

In a still more preferred embodiment of the invention the functionally active variant of an is derived from the naturally occurring XCR1 ligand of any of the sequences of SEQ ID NOS: 1 to 4 by conservative substitutions. Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc. In one embodiment, one conservative substitution is included in the peptide. In another embodiment, two conservative substitutions or less are included in the peptide. In a further embodiment, three conservative substitutions or less are included in the peptide.

Examples of conservative amino acid substitutions include, but are not limited to, those listed below:

| Original Residue | Conservative Substitutions |
|---|---|
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Asn |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In another preferred embodiment of the invention the molecule i) is an anti-XCR1 antibody or functionally active fragment thereof which is capable of binding specifically to the XCR1. The functionally active fragment of the antibody is defined analogously to the functionally active fragment of XCL1 (see above), i.e. the functionally active fragment (a) is characterized by being derived from any anti-XCR1 antibody by one or more amino acid deletions, such as C-terminal, N-terminal and/or internal deletions and (b) is characterized by having a biological activity similar to that displayed by the anti-XCR1 antibody from which it is derived, including the ability to binding to XCL1. Naturally occurring antibodies are proteins used by the immune system to identify and neutralize foreign objects. Each naturally occurring antibody has two large heavy chains and two small light chains and can bind to a different antigen. The present invention includes, for example, monoclonal and polyclonal antibodies, chimeric, single chain, and humanized antibodies, as well as Fab fragments, Fab, Fab', F(ab')$_2$', Fv, or the product of a Fab expression library. The antibody or antibody component can further be modified to prolong its biological half-life or in other ways to make them more suitable for targeting. Antibodies generated against XCR1 can be obtained by direct injection of XCR1 or a fragment thereof into an animal or by administering XCR1 or a fragment thereof to an animal, preferably a non-human. The antibody so obtained will then bind to XCR1. For preparation of monoclonal antibodies, any technique known in the art, which provides antibodies produced by continuous cell line cultures, e.g. a hybridoma cell line, can be used. The production of a suitable monoclonal antibody is also detailed in Example 7. Techniques described for the production of single chain antibodies (U.S. Pat. No. 4,946,778) can be adapted to produce single chain antibodies to XCR1. Also, transgenic mice or other organisms such as other mammals may be used to express humanized antibodies to XCR1.

In another preferred embodiment of the invention the molecule i) is a (poly)peptide. Peptides or polypeptides are polymers formed from the linking, in a defined order, of α-amino acids. The link between one amino acid residue and the next is known as an amide bond or a peptide bond. Proteins are polypeptide molecules (or consist of multiple polypeptide subunits). The distinction is that peptides are short and polypeptides/proteins are long. However, in the context of the present invention the terms peptide, polypeptide and protein are used interchangeably. (Poly)peptides are preferably used as molecules i) in the present invention are detailed above in connection with XCL1 and variants thereof. Alternatively, one could also use (poly)peptide libraries to identify (poly)peptides capable of binding to XCR1, capable of activating XCR1-bearing APC, and preferably capable of eliciting endocytosis in XCR1-bearing APC. The assay systems to identify endocytosis-inducing (poly)peptides have been described above and in Examples 2 and 4.

In another preferred embodiment of the invention the molecule i) is a small organic molecule, i.e. a carbon-containing compound that usually has a molecular weight of less than about 2,000 g/mol, preferably of less than about 1500 g/mol, still more preferably of less than 1000 g/mol. The organic molecule may be, for example, an alcohol, aldehyde, alkan, alkene, amine or aromatic compound. One could also use libraries of small organic molecules or libraries of natural products to identify molecules capable of binding to XCR1, capable of activating XCR1-bearing APC, and preferably capable of eliciting endocytosis in XCR1-bearing APC. The assay systems to identify endocytosis-inducing small organic molecules have been described above and in Examples 2 and 4.

As detailed above, the delivery system of the invention is suitable for delivering a substance into a XCR1 positive professional antigen-presenting cell. XCR1 positive means that the professional antigen-presenting cells bear the receptor XCR1 on their surfaces. An antigen-presenting cell (APC) is a cell that displays foreign antigen complexed with MHC on its surface. T cells may recognize this complex using their T cell receptor (TCR). APCs fall into two categories: professional or non-professional. Since almost every cell in the body is technically an APC (since it can present antigen to CD8$^+$ T cells via MHC class I molecules), the term "professional antigen-presenting cell" is limited to those APC which can prime naïve T cells (i.e., activate a T cell that has not been previously exposed to an antigen). Professional APC express MHC class II as well as MHC class I molecules, and can stimulate CD4$^+$ ("helper") cells as well as CD8$^+$ ("cytotoxic") T cells. These professional APCs are very efficient at internalizing antigen, e.g. either by phagocytosis or by (receptor-mediated) endocytosis, and then display a fragment of the antigen, bound to class I or class II MHC molecule, on their membrane. The T cell recognizes and interacts with the antigen-class I or II MHC molecule complex on the membrane of the APC. An additional co-stimulatory signal is then produced by the antigen presenting cell, leading to activation of the T cell. Although macrophages and B cells can efficiently present antigen, presently the only well-known professional APC are the dendritic cells (DC), among them CD8$^+$ dendritic cells. More preferably, the delivery system is capable of mediating presentation of the substance or a fragment thereof as an antigen by the XCR1 positive professional antigen-presenting cells in a subject, particularly by a major histocompatibility complex (MHC) class I molecule ("cross-presentation").

In accordance with the present invention, the delivery system may be any suitable system comprising the components (molecule i) and substance ii)) as detailed herein.

For example, the substance ii) of the delivery system (including e.g. immunogen, allergen, tolerogen, adjuvant, drug, chemical, DNA, RNA, expression vector system, engineered virus, toxin, enzyme, etc.) can be non-covalently attached to the molecule i) (i.e. the targeting agent), e.g. by ionic strength forces, adhesion, cohesion, and other. Alternatively and preferably, the substance ii) can be directly linked to the molecule i) by chemical coupling, or utilizing a linker such as a peptide linker, or as a fusion protein in case of proteinacious components.

Alternatively, the substance to be delivered (for example the immunogen, allergen, tolerogen, adjuvant, drug, chemical, DNA, RNA, expression vector system, engineered virus, toxin, enzyme, etc.) could be packaged/encapsulated into a "vehicle" to preserve the integrity and effectiveness of the substance is to be targeted to XCR1-bearing APC. Such a vehicle could be a live or dead cell, virus, virus-like particle, nanoparticle, lipid-based system (e.g. liposome), exosome, apoptotic body, colloidal dispersion system, polymer, carbohydrate, microsphere, or any other suitable vehicle. This vehicle would be targeted to XCR1-bearing APC by the presence of a targeting agent, i.e. a molecule i), (see above) on the (outer) surface of the vehicle, in order to allow a specific binding of the vehicle to XCR1-bearing APC, followed by internalization, if required.

A particularly preferred vehicle is a structural protein of a virus or a multimeric structure thereof, such as a capsomere, a virus like particle or a virus. The multimeric structure may be an aggregate of at least about 5, preferably at least about 10, more preferably at least about 30, most preferably at least about 60 structural proteins and may contain the substance to be delivered inside the multimeric structure. It is known that a structural protein of viruses such as parvoviruses (e.g. adeno-associated virus 2) may be modified to present on their surface a particular protein. In accordance with that the structural protein could be modified to present a proteinacious molecule binding to XCR1 such as a naturally occurring XCR1 ligand or variant thereof, as defined above, on the surface of the vehicle. Then, the vehicle binds to DC via XCR1 and could be incorporated into the DC. Suitable insertion sites are disclosed e.g. in U.S. Pat. No. 6,719,978.

In a further embodiment of the invention the delivery system of the invention further comprises iii) an adjuvant, particularly a "danger signal".

The adjuvant is a compound capable of improving the immune response against the administered antigen by at least one of a number of mechanisms including improved antigen-uptake, prolonged biological half-life of the antigen, deposit-like effect, activation of the innate immune response by providing a "danger signal", induction of cytokines, activation and/or maturation of DC, induction of ligands for T cell co-stimulatory molecules, and others. Any compound improving the specific interaction of NK cells or T cells with DC would also act as an adjuvant. Adjuvants can be grouped into two categories. One type of adjuvant improves the recognition of an antigen by the immune system, e.g. by improving the antigen uptake into professional APC or by optimizing the interaction of T cells of NK cells with professional APC. This type of adjuvant does not induce inflammation or provide a "danger signal" and could thus be used to improve the effect of a tolerogen in an attempt to induce anergy or tolerance in the immune system against this tolerogen. The other type of adjuvant induces inflammation in the immune system, e.g. by providing a "danger signals" (see above). Examples of "danger signal"-type adjuvants are immunostimulating complexes (ISCOMs), virus-like particles (VLP), LPS, BCG, unmethylated CpG-motifs, double-stranded RNA, and others. Examples of proteinacious "danger signal"-type adjuvants are heat-shock proteins or High Mobility Group Protein B1.

In one embodiment of the invention the molecule i), the substance ii) and optionally the adjuvant iii) are one or more (poly)peptide(s), wherein the polypeptide is as defined above. The molecule i), the substance ii) and optionally the adjuvant iii) may be in one (poly)peptide (i.e. a fusion protein) and it may be two or more (poly)peptides.

In a further embodiment of the invention the molecule i), substance ii) and optionally the adjuvant iii) are bound to each other covalently and/or non-covalently. As detailed above, the components may be in one fusion protein. Alternatively, the components may be linked to each other by a suitable linker. In case of a fusion protein, the linker is composed of one or more amino acid residues. Alternatively, the components may be bound to each other non-covalently, such as by an ionic bond, hydrogen bonds and/or van der Waals' bonds. The components may encompass suitable domains providing for the covalent or non-covalent bonding. For covalent bonding this includes peptide linker or coupling groups, enabling coupling of the component to each other. For non-covalent bonding, examples of domains proving for bonding include the biotin-avidin system, an antibody or fragment thereof and its antigen, or an enzyme or part thereof and its substrate.

In a further aspect the present invention relates to one or more nucleic acids coding for the (poly)peptide(s) of the delivery system of the invention, if the molecule i), the substance ii) and optionally the adjuvant iii) are one or more (poly)peptide(s). Nucleic acid molecules of the present invention may be in the form of RNA, such as mRNA or cRNA, or in the form of DNA, including, for instance, cDNA and genomic DNA e.g. obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand. Nucleic acid molecule as used herein also refers to, among other, single- and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, nucleic acid molecule as used herein refers to triple-stranded regions comprising RNA or DNA or both RNA and DNA.

Furthermore, any of the nucleic acid molecules encoding the delivery system of the invention can be functionally linked, using standard techniques such as standard cloning techniques, to any desired regulatory sequences, such as a promoter or enhancer or a leader sequence, or a heterologous coding sequence to create a fusion protein.

In a further aspect the present invention relates a vector comprising the one or more nucleic acid(s) of the invention. A vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. The vector may be used to transduce, transform or infect a cell, thereby causing the cell to express nucleic acids and/or proteins other than those native to the cell. The vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known (see, e.g. Sambrook et al, Molecular Cloning. A Laboratory Manual, $2^{nd}$ edition, Cold Spring Harbor Laboratory, New York (1989)). In one embodiment, the vector is a viral vector. Viral vectors include, but are not limited to, retroviral and adenoviral vectors.

Suitable host cells or cell lines for transfection by this method include bacterial cells. For example, the various strains of E. coli are well-known as host cells in the field of biotechnology. Various strains of B. subtilis, Pseudomonas, Streptomyces, and other bacilli and the like may also be employed in this method. Many strains of yeast cells known to those skilled in the art are also available as host cells for expression of the peptides of the present invention. Other fungal cells or insect cells such as Spodoptera frugipedera (519) cells may also be employed as expression systems. Alternatively, mammalian cells, such as human 293 cells, Chinese hamster ovary cells (CHO), the monkey COS-1 cell line or murine 3T3 cells derived from Swiss, BALB/c or NIH mice may be used. Still other suitable host cells, as well as methods for transfection, culture, amplification, screening, production, and purification are known in the art.

A (poly)peptides of the invention may be produced by expressing the nucleic acid(s) of the invention in a suitable host cell. The host cells can be transfected, e.g. by conventional means such as electroporation with at least one expression vector containing a nucleic acid of the invention under the control of a transcriptional regulatory sequence. The transfected or transformed host cell is then cultured under conditions that allow expression of the protein. The expressed protein is recovered, isolated, and optionally purified from the cell (or from the culture medium, if expressed extracellularly) by appropriate means known to one of skill in the art. For example, the proteins are isolated in soluble form following cell lysis, or extracted using known techniques, e.g. in guanidine chloride. If desired, the (poly)peptide of the invention is produced as a fusion protein. Such fusion proteins are those described above. Alternatively, for example, it may be desirable to produce fusion proteins to enhance expression of the protein in a selected host cell or to improve purification. The molecules comprising the components of this invention may be further purified using any of a variety of conventional methods including, but not limited to: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention. Such purification provides the antigen in a form substantially free from other proteinacious and non-proteinacious materials of the microorganism.

In a further aspect the invention relates to a medicament comprising the delivery system of the invention or the one or more nucleic acid(s) of the invention.

Regarding the medicament of the invention, including all cases of vaccinations, immunogenic or tolerogenic, described herein, the substance ii), particularly the immunogen (including pathogen-derived antigen, allergen, tumor antigen, tolerogen, foreign-tissue antigen, autoimmune antigen, etc.) targeted to XCR1-bearing APC can be applied as a (poly)peptide or protein. Alternatively, the substance ii) can be applied as natural or modified (stabilized) DNA or RNA encoding the (poly)peptide or protein.

Alternatively, it can be applied as a nucleic acid-based, promoter-driven expression vector (e.g. plasmid or linearized RNA or DNA) capable of expressing the immunogenic protein/peptide, once internalized into the XCR1-bearing APC. Preferably, such a vector system would utilize the XCR1 promoter to drive the expression of the (poly)peptide or protein, so that the coded (poly)peptide/protein would be selectively expressed in XCR1-bearing mammal/human APC. Alternatively, it the (poly)peptide or protein can be engineered by recombinant technology into a virus, which after being selectively targeted to XCR1-bearing APC, would be internalized and would start to express the (poly)peptide/protein. Again, it would be preferable that the expression of the (poly)peptide or protein would be driven by the XCR1-promoter. Both in the case of a nucleic-acid based expression vector system or virus system, the (poly)peptide or protein would be expressed in the XCR1-bearing APC, processed, and presented on the cell surface of the APC. Depending on the context (inflammation/"danger signal" versus absence of a "danger signal") the expressed peptide would induce either an immune reaction or a tolerance. The (poly)peptide or protein could be targeted to XCR1-bearing cells alone or together with an adjuvant, or any pharmaceutical compound modifying the function of XCR1-bearing APC.

The medicament of the invention may be administered to a subject in need thereof, preferably mammals, and still more preferably humans. Potential modes of administration include intradermal (subcutaneous), intramuscular, parenteral, gastrointestinal, intravenous, intraarterial, intraarticular, intracisternal, intraocular, intraventricular, intrathecal, intratracheal, intraperitoneal, intrathymical, intrasplenical, to the mucosa, or topically or orally, and combinations thereof, but most preferably intramuscular or subcutaneous or intravenous injection. The volume of the dose for intramuscular administration is preferably up to about 5 mL, for example, between 0.3 mL and 3 mL, between 1 mL and 3 mL, about 0.5 to 1 mL, or about 2 mL. The amount of active ingredient in each dose should be enough to provide for treatment or prevention. In different embodiments, the unit dose of substance to be delivered should be up to about 5 µg substance/kg body weight, between about 0.2 to 3 µg, between about 0.3 to 1.5 µg, between about 0.4 to 0.8 µg, or about 0.6 µg. In alternative embodiments unit doses could be up to about 6 µg substance/kg body weight, between about 0.05 to 5 µg, or between about 0.1 to 4 µg. In different embodiments, the dose is administered 1 to 3 times, e.g. with an interval of 1 to 3 weeks. Representative amounts of protein per dose are from approximately 1 µg to approximately 10 µg, more preferably from approximately 5 µg to approximately 500 µg, still more preferably from approximately 10 µg to approximately 250 µg and most preferably from approximately 25 µg to approximately 100 µg.

The treatment involves administering an effective amount of substance ii) to a subject, preferably a mammal, more preferably a human. Accordingly, a further aspect of the invention relates to a method of preventing or treating a disease (as specified herein), wherein an effective amount of substance ii) is administered to the subject using the delivery system of the invention. The prevention and treatment may be further specified as described herein.

An "effective amount" of the medicament or substance ii) may be calculated as that amount capable of exhibiting an in vivo effect, e.g. preventing or ameliorating a sign or symptom of any of the diseases specified herein. Such amounts may be determined by one of skill in the art. Preferably, such a medicament is administered parenterally, preferably intramuscularly or subcutaneously. However, it may also be formulated to be administered by any other suitable route, including orally or topically. The selection of the route of delivery and dosage of such therapeutic compositions is within the skill of the art.

Treatment in the context of the present invention refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

The medicament may comprise in general at least one suitable pharmaceutically acceptable carrier or auxiliary substance. Examples of such substances are demineralised water, isotonic saline, Ringer's solution, buffers, organic or inorganic acids and bases as well as their salts, sodium chloride, sodium hydrogencarbonate, sodium citrate or dicalcium phosphate, glycols, such a propylene glycol, esters such as ethyl oleate and ethyl laurate, sugars such as glucose, sucrose and lactose, starches such as corn starch and potato starch, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils such as groundnut oil, cottonseed oil, corn oil, soybean oil, caster oil, synthetic fatty acid esters such as ethyl oleate, isopropyl myristate, polymeric adjuvans such as gelatin, dextran, cellulose and its derivatives, albumins, organic solvents, complexing agents such as citrates and urea, stabilizers, such as protease or nuclease inhibitors, preferably aprotinin, E-aminocaproic acid or pepstatin A, preservatives such as benzyl alcohol, oxidation inhibitors such as sodium sulphite, waxes and stabilizers such as EDTA. Colouring agents, releasing agents, coating agents, sweetening, flavouring and perfuming agents, preservatives and antioxidants can also be present in the composition. The physiological buffer solution preferably has a pH of approx. 6.0-8.0, especially a pH of approx. 6.8-7.8, in particular a pH of approx. 7.4, and/or an osmolarity of approx. 200-400 milliosmol/liter, preferably of approx. 290-310 milliosmol/liter. The pH of the medicament is in general adjusted using a suitable organic or inorganic buffer, such as, for example, preferably using a phosphate buffer, tris buffer (tris(hydroxyl-methyl)ami-nomethane), HEPES buffer ([4-(2-hydroxyethyl)piper-azino] ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions. Methods for formulating a medicaments as well as suitable pharmaceutically acceptable carrier or auxiliary substance are well known to the one of skill in the art. Pharmaceutically acceptable carriers and auxiliary substances are a. o. chosen according to the prevailing dosage form and compound.

The delivery system could be targeted to XCR1-bearing APC, depending on the requirement or condition. It can be anticipated that XCR1-bearing APC reside not only in the spleen, the lymph nodes, and the draining lymphatic tissues, but also in all other organs of the mammal/human body, such as the thymus, liver, lung, in the brain, and under mucosal surfaces (e.g. in the gut). Therefore targeting of a pharmaceutical compound can be achieved by injection/application into the respective tissues.

In a preferred embodiment of the invention the medicament is a vaccine and/or adjuvant. As detailed above, vaccines consist of cellular, viral, bacterial, fungal, parasitic, or toxin components, or other antigenic components, which are administered into the body of a mammal or a human. Alternatively, vaccines can be administered as DNA or RNA coding for cellular, viral, bacterial, fungal, parasitic, or toxin components; once in the body, the nucleic acid is translated by body cells into the coded protein, which then acts as an antigen. Vaccines are often administered together with "adjuvants", compounds capable of significantly improving the immune response against the administered antigen by a number of mechanisms including improved antigen-uptake, prolonged biological half-life of the antigen, deposit-like effect, activation of the innate immune response by providing a "danger signal", induction of cytokines, activation and/or maturation of DC, induction of ligands for T cell co-stimulatory molecules, and others. Any compound improving the specific interaction of NK cells or T cells with DC would also act as an adjuvant. In many cases the adjuvant contains components of pathogens, which provide to the immune system "danger signals" (see above).

A vaccine targeted to APC and specifically to cross-presenting APC, could be used to immunize healthy individuals to protect them from infection ("protective vaccine").

Alternatively, such a vaccine could be used for therapeutic purposes. The infected individual, which may not be able to mount a sufficient Th1 immune response to the pathogen, could be vaccinated with a vaccine designed to elicit a powerful and specific Th1 response, in particular cytotoxic response, and would thus become capable of containing or eradicating the infection ("therapeutic vaccine"). Examples would be malaria, tuberculosis, leishmania, prion diseases, orthomyxoviruses and in particular influenza, hepatitis A, hepatitis B, chronic hepatitis C, HIV and other lentiviruses, cytomegalovirus, herpes viruses, papillomaviruses, bunyaviruses, caliciviruses, filoviruses, flaviviruses and in particular hepatitis C virus, papillomaviruses, paramyxoviruses, a variety of respiratory viruses and other viruses, or any other infection specified in the description.

The vaccine could also be used to protect healthy individuals from developing tumors with known antigenic components (e.g. melanoma, prostate carcinoma) ("tumor protective vaccine"). Alternatively, such a vaccine eliciting a powerful Th1 immune response, in particular Th1 cytotoxic response, could be used to cure patients which already have developed tumors. Examples of such tumors would be human virus-induced tumors, in particular papillomavirus-induced tumors, HCV-induced tumors, hepatis B-virus induced tumors and others viruses which induce tumors upon chronic infection. Moreover, the superinduction of Th1 immunity, in particular cytotoxic immunity, would be desirable for spontaneously arising solid tumors (e.g. melanoma, prostate cancer, breast cancer, adenocarcinoma of the gut, lung cancer) and leukemias. In such a case the patient would be treated with known tumor antigens or his own (excised) tumor material targeted in such a fashion to APC, as to elicit a powerful cytotoxic Th1 immune response against tumor-specific antigens.

Some vaccines are used for desensitization of allergic individuals. Allergic individuals are prone to develop a Th2-overreaction to environmental antigens. As a result they develop various allergic responses such as rhinitis, conjunctivitis, food allergy, allergy to venoms, and allergic asthma. The currently available desensitization schemes and treatments aimed at tipping the immune balance to a more Th1-prone immune response to the respective allergen are not fully effective. Therefore, new approaches to induce a more Th1-oriented immunity to the respective allergen(s) are highly desirable. This could be achieved through targeting the respective allergen to APC, in particular DC, capable of eliciting an effective Th1 response to the allergen, and could include the use of adjuvants co-targeted to the Th1 immune system ("therapeutic desensitization"). Before tipping the balance to a Th1 immune response it may be helpful to first delete a an APC population by specifically targeting a toxin to this population. A desensitization vaccine could also be applied to individuals which have a predisposition to develop allergic reaction, but have not yet developed allergic symptoms ("preventive desensitization").

The same principle of desensitization could be applied to autoimmune diseases which are cause by immune reaction to self-antigens, in particular Th1-biased antibody or cellular immune reactions, e.g. rheumatoid arthritis, systemic lupus erythematosus, autoimmune thyrodiditis and other autoimmune diseases based on a Th1-overreaction to self-antigens. Such a desensitization vaccine would be applied in a formulation which would not provide "danger signals" to the immune system and APC. The desensitization vaccine could alternatively be targeted in such a fashion and formulation as to prevent maturation of DC presenting the respective self-immunogen or even induce an "immature" state of the targeted DC. One way to achieve this could include the transient deletion of an APC population by specifically targeting a toxin to this population. These entire regimens would be aimed at modifying the state of dendritic cells in such a fashion as to provide tolerogenic signals to antigen-specific T cells interacting with these DC. In such a way, one could expect to elicit an immune tolerance against the respective (self-)antigen.

In another preferred embodiment of the invention the medicament of the invention is for inducing a memory immune response against the peptide, particularly wherein the memory immune response is a Th1 response, especially a Th1 cytotoxic response.

In conditions in which an immunogenic vaccination is desired, the immunogen has to be targeted to XCR1-bearing mammal/human APC in the context of a "danger signal" (see above). The targeted immunogen could be applied in a vaccine formulation, in which the targeted immunogen and the danger-signal-type adjuvant are mixed in a formulation (e.g. emulsion) and then applied. Alternatively, and preferably, the danger-signal type adjuvant is directly coupled to the targeted immunogen and thus co-targeted to XCR1-bearing APC using a targeting agent, as described.

In another preferred embodiment of the invention relating to immunogenic vaccination the medicament of the invention is for preventing or treating a tumor and/or an infection.

The immunogenic vaccine may be used for prevention or treatment of tumors, particularly in mammals/humans. The targeted immunogen is a tumor antigen. This can be a known tumor antigen; examples for known tumor antigens are melanoma antigens, prostate antigens, and adenocarcinoma antigens (see also above). In that case the tumor antigen can be applied as a protein or peptide moiety capable of inducing an immune reaction to the tumor. In the case of an already established tumor without known tumor antigens, a patient-specific tissue-preparation from excised tumor material can be used as a tumor antigen preparation. The targeted immunogen can also be a virus, mycoplasma, or bacterium which induces a tumor upon chronic infection. Examples of such infectious agents are hepatitis C virus, hepatitis B virus, both inducing liver carcinomas, and HPV, which induces cervix carcinomas, and other. For an immunogenic vaccine, a simultaneous application of a "danger signal"-type adjuvant is necessary. This approach can be used in two different settings. For first, it can be used to vaccinate the mammal/human against a tumor or a tumor-inducing pathogen in a preventive fashion, with known tumor antigens, in individual prone to tumor development. In such a case, the developed Th1 immunity against tumor components or tumor-inducing will prevent the development of the tumor. In the second setting, the patient who already has developed a tumor is vaccinated in a therapeutic fashion in order to mount an effective immune response, in particular a Th1 (cytotoxic) immune response, against the tumor and/or the tumor-inducing pathogen with the aim to eradicate the tumor. This type of approach can be applied in a variety of tumor types, among them melanoma, prostate cancer, breast cancer, carcinoma of the gut, lung cancer, sarcomas, leukemias, lymphomas, gliomas, myelomas, sarcomas, sarcoidosis, microgliomas, meningiomas, astrocytomas, oligodendrogliomas, Hodgkin's disease.

The immunogenic vaccine may be used for prevention or treatment of an infection, particularly in mammals/humans. As targeted immunogens can serve life, attenuated, or dead pathogens, i.e. viruses, bacteria, parasites, fungi, mycoplasma, inactivated toxins, or immunogenic components thereof. The immunogen can also be applied as a protein or peptide moiety inducing immunity to the pathogen. For an immunogenic vaccine, a simultaneous application of a "danger signal"-type adjuvant is in general necessary, unless the pathogen or its component already provides the necessary "danger signal". Such a "danger signal" could be provided by a variety of components, examples are LPS, unmethylated CpG, High Mobility Group Protein B1, heat-shock proteins, and other, see above). This approach can be applied to a variety of pathogens. Examples are tuberculosis, helicobacter, malaria, leishmania, prion diseases, orthomyxoviruses and in particular influenza, coronaviruses and in particular the SARS virus, West Nile virus, hepatitis B virus, hepatitis A virus, human immunodeficiency virus (HIV) and other lentiviruses, cytomegalovirus, herpesviruses, papillomaviruses, bunyaviruses, caliciviruses, filoviruses, flaviviruses and in particular hepatitis C virus, paramyxoviruses, a variety of respiratory viruses and other viruses which need for containment and eradication an effective Th1 immune response, and in particular a Th1 cytotoxic response.

The immunogenic vaccine may be used for prevention or treatment (desensitization) of an allergic disease, particularly in mammals/humans. The targeted immunogen is an allergen. Examples for allergens are dust mite allergen, pollen allergens, grass allergens, venom allergens, food allergens, and other. The allergen can also be applied as an immunogenic component of the allergen, or a protein or peptide moiety capable of inducing an immune reaction to the allergen. For an immunogenic vaccine a simultaneous application of a "danger signal"-type adjuvant is necessary. The goal is to change the immune response of the individual to the allergen from a Th2 to a Th1 immune pattern in a variety of conditions. Examples are allergic asthma, other allergic lung diseases, food allergy, allergic sinusitis, allergic rhinitis (hay fever), polyposis, and other allergic conditions. This approach can be used in an already established allergic condition as a therapeutic vaccination (desensitization). Alternatively, individuals prone to allergic reactions can be vaccinated against known allergens in a preventive fashion, so that they no longer develop an untoward Th2 immune reaction pattern toward the allergen.

In another preferred embodiment of the invention the medicament of the invention is for inducing tolerance against the (poly)peptide.

There are a number of conditions in which the development of tolerance instead of immunity to a given immunogen is desired. This is made possible, since there is for the first time the possibility to specifically target an immunogen (i.e. tolerogen) into XCR1-bearing APC, which play a pre-eminent role in the establishment and upkeep of immune tolerance in the body of the mammal/human. The induction of tolerance is desirable in organ transplantation, in autoimmune diseases, and in allergic conditions. Under these conditions no "danger signal" should be present in the medicament.

Preferably, the medicament is for inhibiting transplant rejection, an allergy and/or an autoimmune disease.

The tolerogenic vaccination may be used in organ transplantation. The human recipient of the organ or tissue can be tolerized before transplantation to the foreign tissue antigens by targeting the immunogen to XCR1-bearing APC in the absence of a danger-signal adjuvant. The immunogen in such case can be cells of the donor, components of donor cells, peptides or proteins. Under these conditions the Th1 immune system of the host will be made tolerant to the foreign tissue antigens and will tolerate the graft. This approach can be applied in organ transplantation (e.g. liver-, heart-, lung-, skin-, kidney-transplantation), bone-marrow transplantation, or insulin cell transplantation, or any other foreign-tissue transplantation. Through application of the foreign tissue antigen into the thymus or bone marrow one would induce central tolerance. Through application of the immunogen into the periphery one would induce peripheral tolerance.

The tolerogenic vaccination may be used for the treatment and/or prevention of allergy. The allergic individual or the individual prone to allergic reactions can be made tolerant to an allergen by targeting the allergen to XCR1-bearing APC in the absence of a danger-signal adjuvant. This can be done in a preventive fashion in allergy-prone individuals or in already established allergy. The targeted immunogen is an allergen or part of an allergen. The goal is to make the immune system of the individual tolerant to a given allergen. This approach can be applied for allergic conditions, in which the allergic response is driven by the Th1 immune system, such as in heavy metal (nickel, chrome, other) sensitization. This approach can also be applied in individuals in which it is desired to tolerize both the Th2 and the Th1 immune system to the allergen or sensitizing agent, such as in allergic asthma, other allergic lung diseases, food allergy, allergic sinusitis, allergic rhinitis (hay fever), polyposis, and other allergic conditions.

The tolerogenic vaccination may be used for the treatment and/or prevention of autoimmune conditions. Many human autoimmune diseases are driven by a Th1 autoimmune process. It would be desirable to make the autoimmune individuals or individuals prone to autoimmune reactions tolerant to the autoimmune antigens. These autoimmune antigens are known (as in myasthenia gravis, autoimmune thyroiditis, multiple sclerosis, autoimmune diabetes mellitus), or may be determined in the foreseeable future. The individual would be made tolerant to the autoantigen by targeting the autoantigen to XCR1-bearing APC in the absence of adjuvant. This approach could be applied in myasthenia gravis, autoimmune thyroiditis, multiple sclerosis, rheumatoid arthritis, psoriasis, inflammatory bowel disease (e.g. Crohn's disease, ulcerative colitis), SLE, ankylosing spondylitis, reactive arthritis, psoriatic arthritis, and other Th1-driven autoimmune conditions.

The drawback of many adjuvants is the broad and unspecific effect they exert on a number of cell types in the body, when administered in a non-directed fashion. Therefore attempts were undertaken to make the effect of adjuvants more specific, e.g. by coupling the adjuvant to the immunogen. However, presently there are no methods available which would allow for targeting an adjuvant selectively to DC, and more specifically to cross-presenting DC, both to minimize untoward effects and to selectively target the most effective antigen-presenting DC population. Therefore, there is a need to develop such a targeting of adjuvants. As detailed above, it is now possible to specifically target DC using a XCR1 ligand. Additionally, it could be shown that XCL1 (ATAC) acts as an adjuvant in the induction of CD8+ T cell cytotoxicity.

Accordingly, another aspect of the invention relates to an adjuvant comprising XCL1 or a functionally active fragment thereof (as defined above), particularly for enhancing immune response in a subject by modulating the function of XCR1 positive antigen-presenting cells.

The ability of XCL1 to attract, activate and to improve the antigen-presenting capabilities of XCR1-bearing APC make XCL1 an ideal vaccine adjuvant without danger-signal properties. The addition of XCL1 to any vaccine or pharmaceutical formulation can be expected to attract XCR1-bearing APC to the site of application in the mammal/human body. In case of an applied immunogen, this would improve antigen uptake and presentation in XCR1-bearing APC, in particular cross-presentation, and improve the T- and B cell immune response. Depending on the context of application, this immune response could result in a higher degree of tolerance to the applied immunogen (non-inflammatory conditions, no "danger signal"), or result in an improved immunity to the applied antigen, when administered in inflammatory conditions ("danger signal"). Co-administration of XCL1 with a pharmaceutical compound can be expected to lead to an increased uptake of this compound into XCR1-bearing APC.

FIGURES

FIG. 1 shows the observed number of XCR1 copies after quantitative PCR of polyA-mRNA of diverse murine splenic cell populations, normalized to the expression in 10 000 cells. Only CD11c$^+$CD8$^+$ DC express significant amounts of XCR1 mRNA.

FIG. 2A-FIG. 2B show activation of XCR1-bearing DC by XCL1. CD8$^+$CD11c$^+$ (A) or CD8$^+$CD11c$^+$ (B) dendritic cells (DC) were immobilized on poly-L-lysine-coated glass coverslips and loaded with fura-2/AM (2 μM). Cells were imaged in a monochromator-assisted digital video imaging system and challenged with 100 nM ATAC at 60 s. Data represent intracellular Ca$_{2+}$ concentrations ([Ca$^{2+}$+]$_i$) in 27-33 single cells (thin lines) measured in 3 independent experiments. Thick lines: mean [Ca$_{2+}$]$_i$ signal averaged over all cells measured. XCL1 induces a [Ca$_{2+}$]$_i$ signal in CD8$^+$CD11c$^+$(A) but not in CD8$^+$CD11c$^+$(B) dendritic cells.

Figure 6:
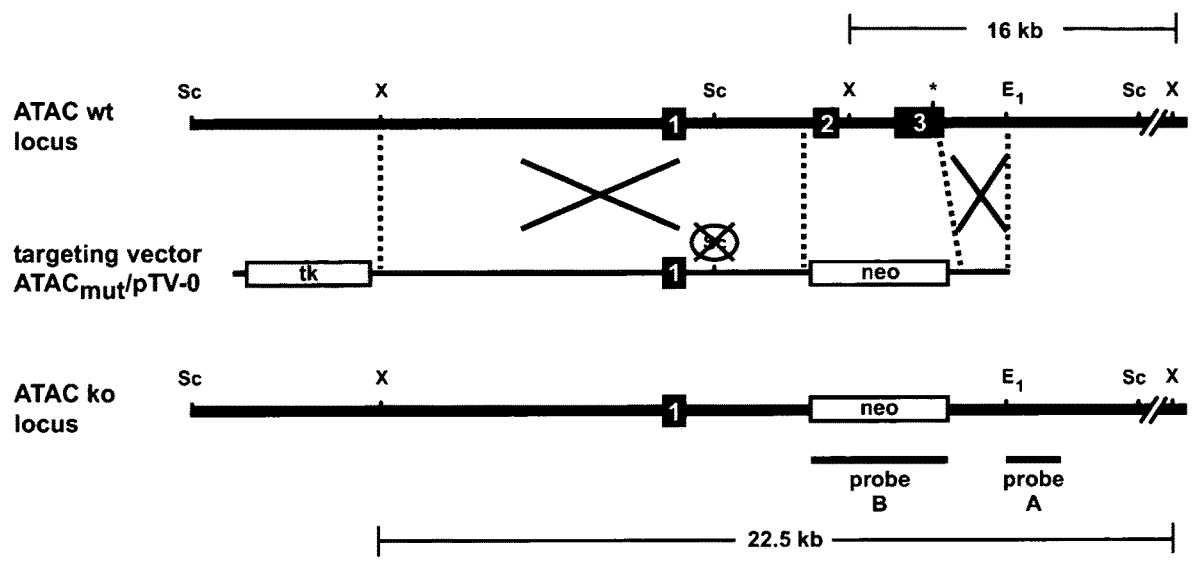
Figures 7A, 7B, 7C, 7D, 7E, 7F, 7G, 7H, 7I:
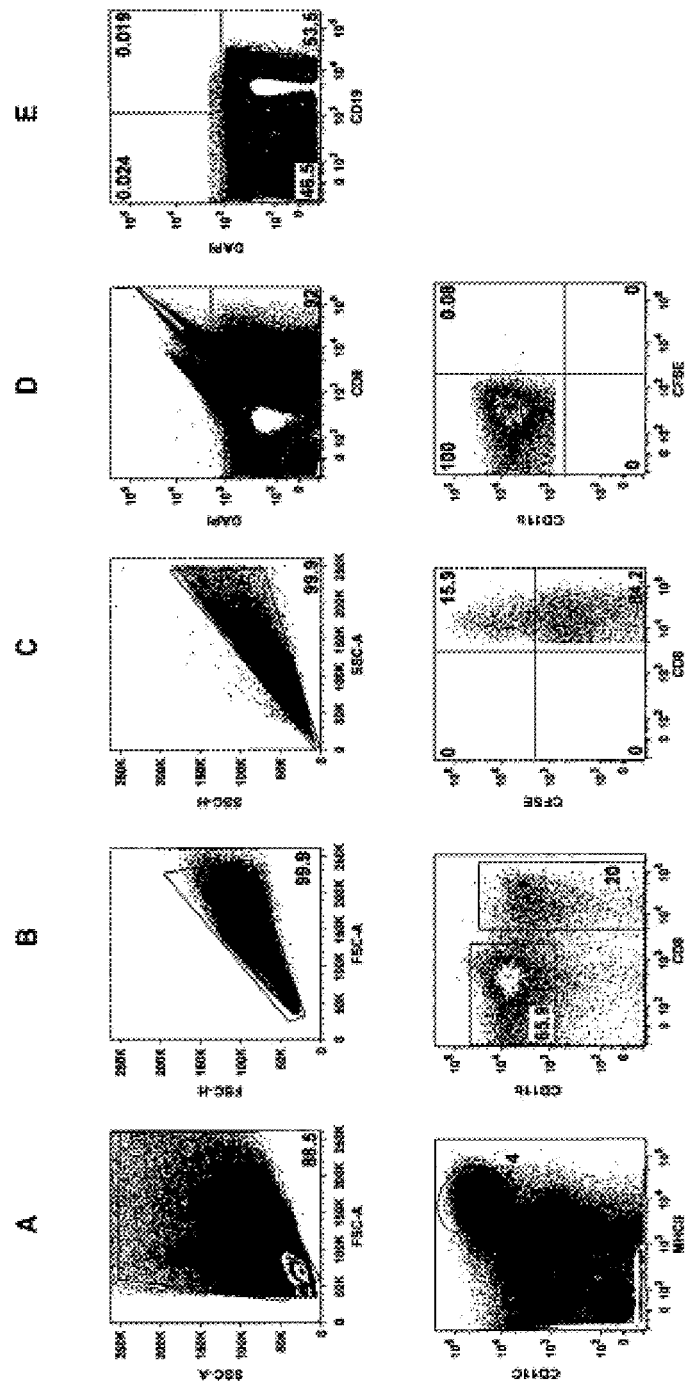

FIG. 6 shows maps of the endogenous ATAC locus containing three exons (numbered black boxes, top), the targeting vector $ATAC_{mut}$/pTV-0 (middle) and the expected structure of the targeted locus (bottom). Restriction sites: X, XbaI; Sc, SacI; $E_1$, EcoRI. Selection markers: neo, neomycin resistance; tk, thymidin kinase from herpes simplex virus. The sizes of the expected XbaI restriction fragments of the endogenous and targeted ATAC locus are indicated (16 kb and 22.5 kb, respectively).

FIG. 7A-FIG. 7I show the gating strategy for the analysis of splenic CD11c+CD8+ DC by flow cytometry. The stained cell surface markers are indicated on the axes. The CD11c+ MHC-11+ cells represented around 4% of splenic nucleated cells, after dead cells (DAPI+, 7D) and CD19+ cells (7E) were gated out. These CD11c+MHC-11+ cells were further subdivided into CD11b+ and CD8+ (dendritic) cells (7G). The fluorescence signal (CFSE) is shown for CD11c+CD8+ (7H) and CD11c+CD11b+ (7I) (dendritic) cells.

Figures 8A, 8B:
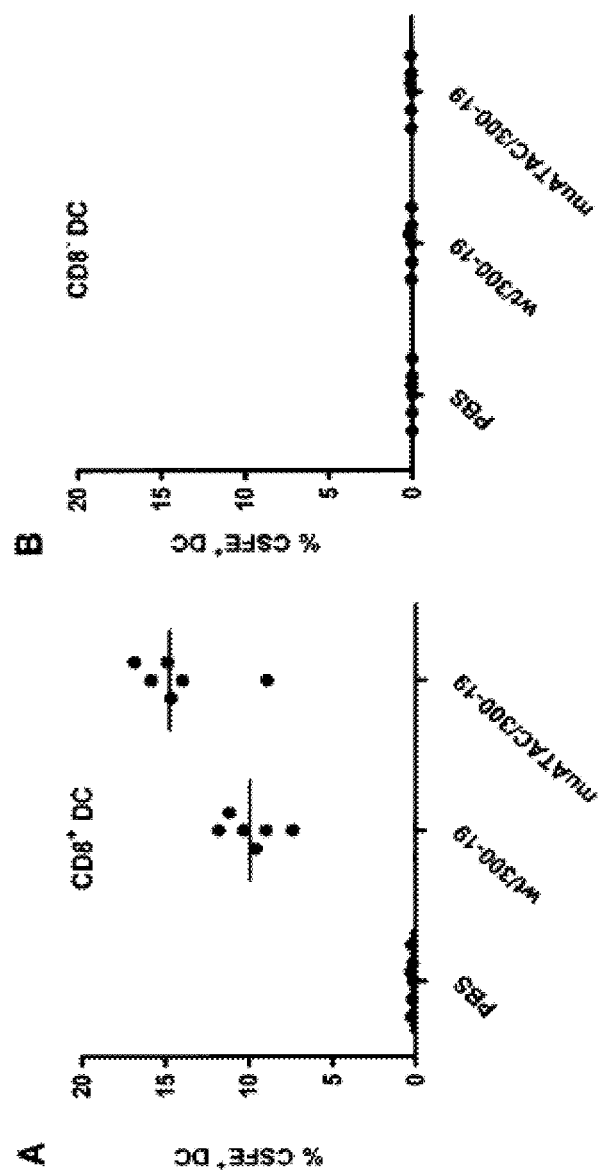

FIG. 8A-FIG. 8B show the percentage of splenic CSFE+ DC after injection of CSFE-labeled cell lines. Data obtained with CD8+ DC are shown in A, data obtained with CD8− DC are shown in B. XCL1 significantly improves cell (antigen) uptake into CD8+ DC.

Figure 9:
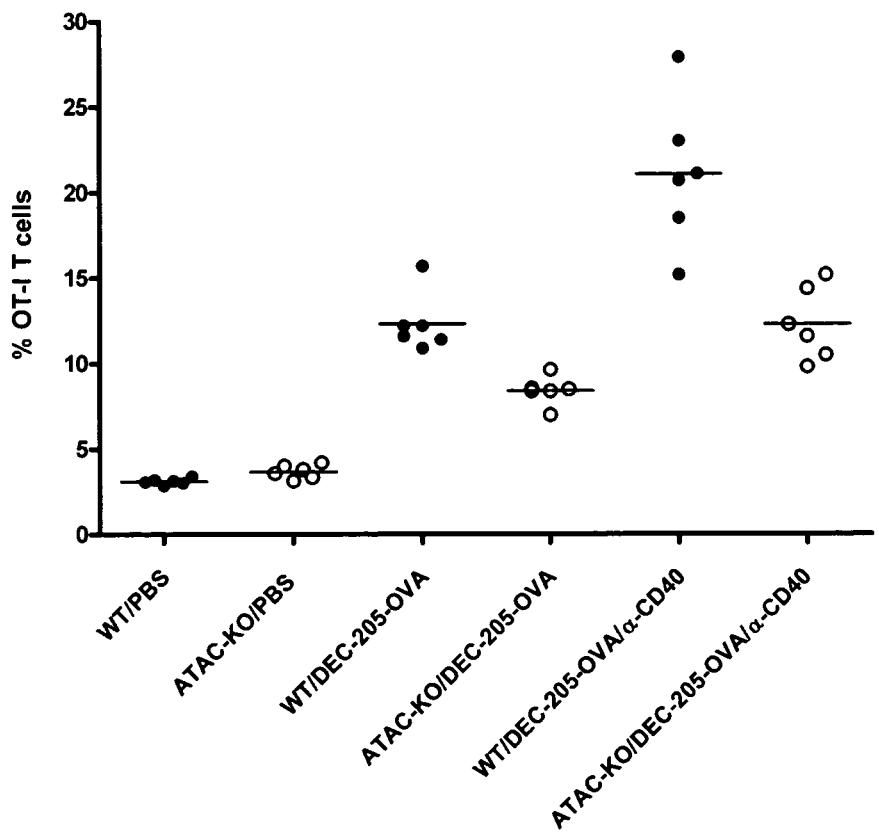

FIG. 9 shows the percentage of OT-I cells in spleens of recipient mice on day 3 after injection of PBS, DEC-205-OVA or DEC-205-OVA/α-CD40. A higher percentage is seen in wild type mice (black circles) compared to ATAC-KO-mice (white circles).

Figure 10:
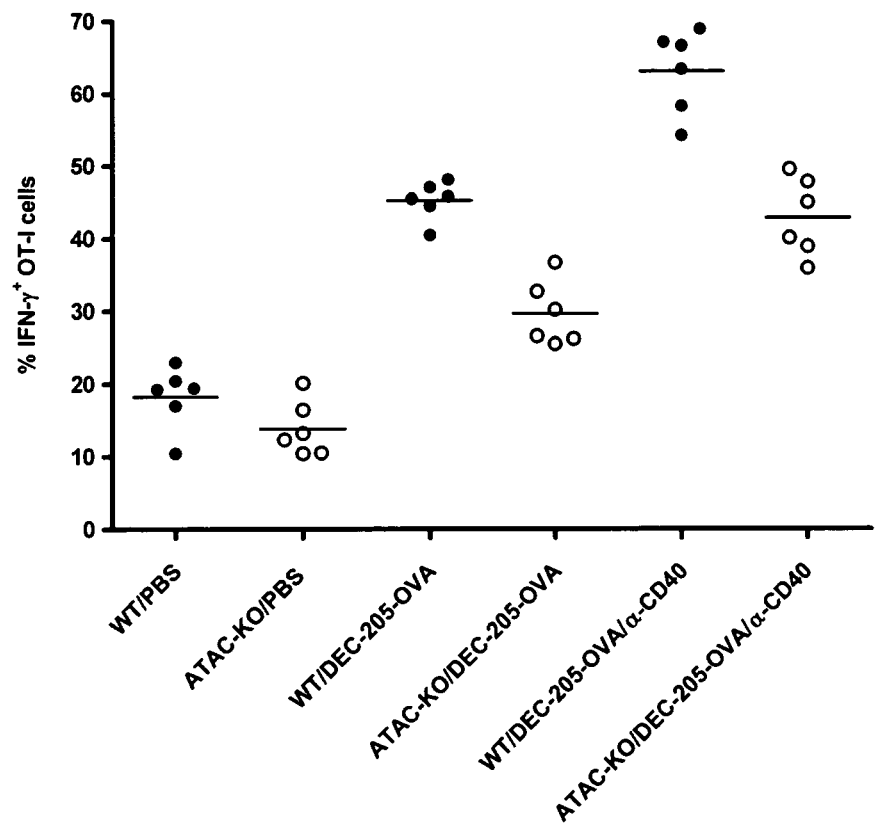

FIG. 10 shows the percentage of IFN-γ-expressing OT-I cells isolated from spleens of recipient mice on day 3 and restimulated in vitro. A higher percentage of IFN-γ-secreting OT-I cells is seen in wild type mice (black circles) compared to ATAC-KO-mice (white circles), indicating the adjuvant effect of XCL1 on the differentiation of T cells.

Figure 11:
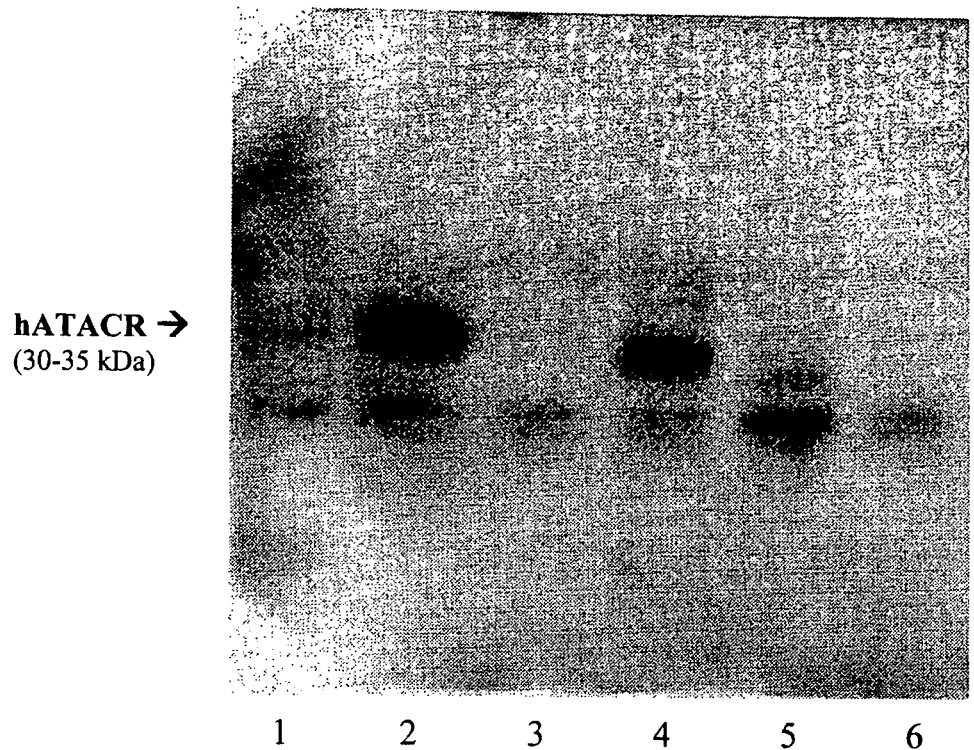
Figure 12:
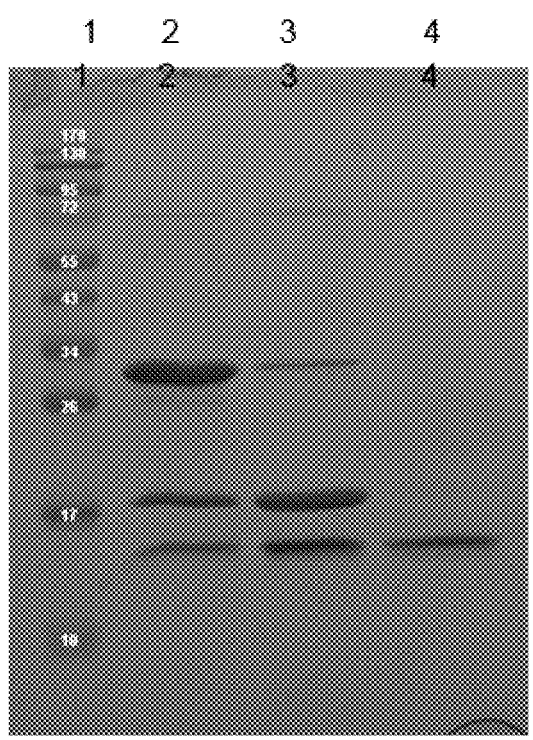

FIG. 11 shows a Western Blot of immunoprecipitates (i.p.) of human XCR1 protein with mAb 6F8.
lane 1: marker
lane 2: i.p. with mAb 6F8 from transfectant "5' c-myc/hATACR/P3X"
lane 3: i.p. with mAb 6F8 from P3X wild-type line
lane 4: i.p. with mAb 6F8 from transfectant "3' c-myc/hATACR/P3X"
lane 5: i.p. with mAb 6F8 from transfectant "hATACR/300-19"
lane 6: i.p. with mAb 6F8 from 300-19 wild-type line FIG. 12 shows a Coomassie stained SDS-PAGE loaded with different preparations of recombinant murine XCL1.
lane 1: marker
lane 2: metal-affininity purified XCL1-SUMO fusion protein
lane 3: XCL1-SUMO fusion protein after digestion with SUMO protease
lane 4: purified XCL1

Figure 13:
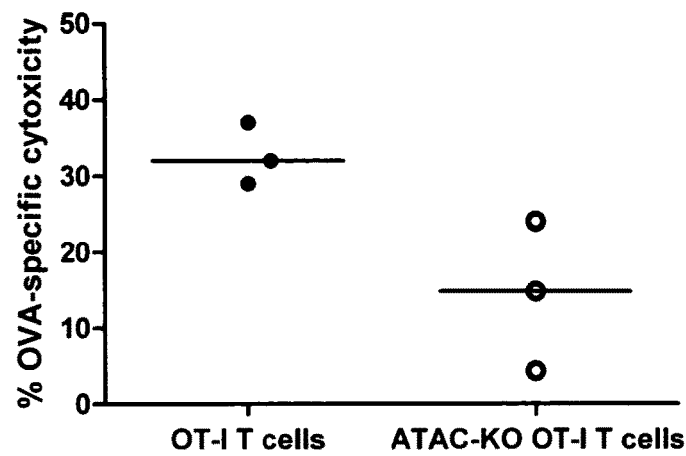

FIG. 13 shows the OVA-specific cytotoxicity of OT-I T cells and ATAC-KO OT-I T cells after adoptive transfer into C57BL/6 or ATAC-KO mice, respectively. OVA/300-19 cells were used for immunization on day 1 after transfer, and the in vivo cytotoxicity assay was performed on day 6.

Figure 14:
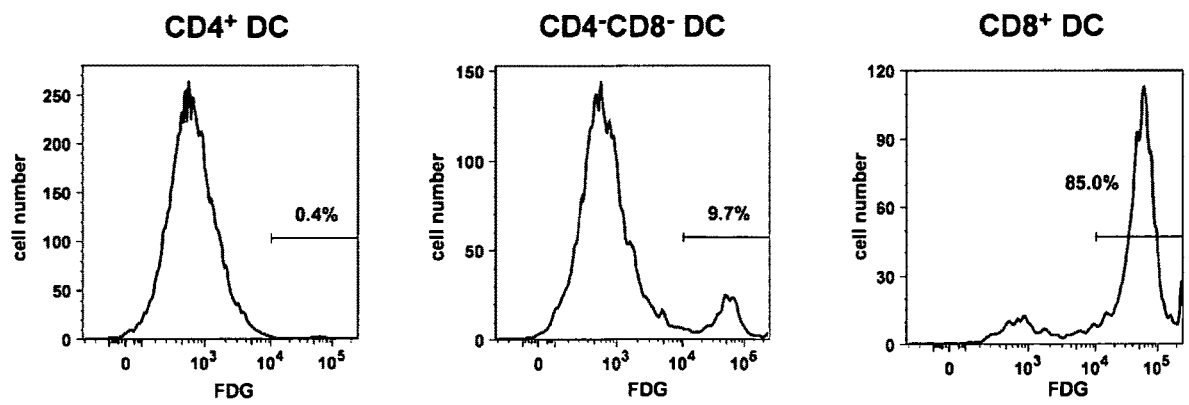

FIG. 14 shows expression of XCR1 in splenic DC.

EXAMPLES

Example 1: Exclusive Detection of XCR1 mRNA in CD8+ DC

Spleens from C57BL/6 mice were digested in RPMI1640 containing 2% (v/v) FBS (low endotoxin; PAA, Pasching, Austria), 500 µg/ml collagenase D, and 20 µg/ml DNase I (both from Roche Diagnostics GmbH, Penzberg, Germany) for 25 min in a shaking water bath at 37° C. The suspension was adjusted to 10 mM EDTA and incubated for 5 additional minutes. Cells were passed through a 70-vim-mesh (BD Biosciences, San Jose, Calif., USA) and rinsed with MACS-PBS (PBS, 2 mM EDTA, 0.5% (w/v) BSA low endotoxin). After sedimentation with 380×g at 4° C. the cells were suspended in MACS-PBS.

For the magnetic isolation of B cells, T cells, NK cells, granulocytes or macrophages, the cells of digested spleen were depleted of DC (dendritic cells) by negative selection with anti-CD11c-microbeads (Miltenyi Biotec, Bergisch Gladbach, Germany). B cells were purified by positive selection with anti-CD19-microbeads, total T cells with anti-CD90-microbeads, NK cells with anti-DX5-microbeads, granulocytes with anti-Ly6G-microbeads, macrophages with biotin-conjugated mAb F4/80 (ATCC, Manassas, Va., USA) and anti-biotin microbeads (Miltenyi Biotec, supra), all according to the manufacturer's instructions (Miltenyi Biotec, supra). For isolation of DC, cells of digested spleen were underlayed with 1.069 g/ml Nycodenz solution (Axis-Shield, Oslo, Norway) and centrifuged for 20 min with 800×g at 4° C. Low density cells were harvested from the interphase and washed once with MACS-PBS. Total DC were purified by magnetic cell sorting with anti-CD11c-microbeads according to the manufacturer's instructions (Miltenyi Biotec, supra). Briefly, cells were preincubated for 5 min at 4° C. with MACS-PBS containing 200 µg/ml anti-FcRII/III (mAb 2.4G2; ATCC, supra) and 500 µg/ml purified rat IgG (Nordic, Tilburg, The Netherlands) to prevent unspecific binding. CD11c-microbeads were added for additional 15 min, and washed twice with MACS-PBS. Cells were loaded onto a LS column (Miltenyi Biotec, supra) fitted in a MidiMACS Seperator magnet (Miltenyi Biotec, supra) and washed 3-times; CD11c-positive cells were retained on the column and eluted after removing the column from the magnetic field by adding 5 ml of MACS-PBS. CD11c+ splenic cells were stained in FACS-PBS (PBS, 2.5% (v/v) FBS, 0.1% (w/v) NaN3) containing 200 µg/ml anti-FcR11/III (mAb 2.4G2), 500 µg/ml purified rat IgG (both as blocking reagents), with anti-CD8 (mAb 53-6.72; ATCC, supra), anti-CD11b (mAb 5C6; ATCC, supra), anti-CD11c (mAb N418; ATCC, supra), and anti-MHC class II (mAb M5/114.15.2; ATCC, supra) for 20 min at 4° C. After washing, the cells were sorted on an Aria Cell Sorter (BD Bioscience) into CD11c+CD8− and CD11c+CD8+ DC subpopulations to a purity>95%.

Total RNA was prepared using the High Pure RNA Isolation Kit (Roche Diagnostics GmbH, supra) according to the protocol. In brief, cells ($10^5$-$10^7$) were collected by centrifugation and suspended in 200 µl PBS and mixed with 400 µl Lysis/Binding buffer. The lysate was applied onto the filter tube and centrifuged for 15 s with 8000×g. The filter was washed once with 500 µl Wash Buffer I and incubated for 15 min with DNase I to remove remaining DNA. After washing with 500 µl of Wash Buffer I and twice with Wash Buffer II, the RNA was eluted twice with 50 µl Elution Buffer. RNA concentration and purity of the combined eluate was determined on the Agilent 2100 bioanalyzer (Agilent Technologies, Waldbronn, Germany) and by photometrical reading.

Small scale mRNA from $10^5$-$10^7$ cells was isolated with the µMACS mRNA Isolation Kit (Miltenyi Biotec, supra). The cell sediment was lysed in 1 ml of Lysis/Binding Buffer and centrifuged with 13000×g for 3 min. After the addition of 50 µl Oligo-(dT)-microbeads, the lysate was loaded onto a µMACS column fitted into a µMACS separation magnet. The column was rinsed twice with 200 µl of Lysis/Binding Buffer and 4-times with Wash Buffer. Traces of remaining DNA were removed by digestion with 5 U DNase I (Promega, Madison, Wis., USA) for 1 min. Washing steps were repeated to remove digested DNA and DNase. Preheated Elution Buffer (120 µl, 70° C.) was used to elute the purified mRNA. Quality control was performed as described above.

Total RNA or mRNA were reverse-transcribed into cDNA with the Reverse Transcription System according to the manufacturer's instructions (Promega, Madison, Wis., USA). In short, 0.1-1 µg total RNA or 1-10 ng poly(A)$^+$ mRNA was denatured at 70° C. for 10 min and immediately chilled thereafter. Reverse-transcription was performed with Oligo(dT)15 primers and AMV reverse transcriptase for 15 min at RT, followed by an incubation at 42° C. Reaction was stopped by a 5 min heating step at 95° C. followed by incubation at 4° C. for 5 min. The cDNA was then analyzed by quantitative PCR for their content on XCR1 copies and β2-microglobulin was used as an internal standard. For amplification of murine XCR1, 400 nM forward primer (5'-TGCCTGTGTTGATCTCAGCAC-3'; SEQ ID NO: 11), 200 nM reverse primer (5'-CGGTGGATGGTCATGATGG-3'; SEQ ID NO: 12), and 150 nM hybridization probe (5'-FAM-CATCAGCCTCTACAGCAGCATCTTCTTCCT-TAMRA-3') were used. Murine the β2-microglobulin was amplified using 300 nM forward primer (5'-CGCTCGGT-GACCCTAGTCTTT-3'; SEQ ID NO: 13), 300 nM reverse primer (5'-TTCAGTATGTTCGGCTTCCCA-3'; SEQ ID NO: 14), and 150 nM hybridization probe (5'-FAM-CG-GCTTGTATGCTATCCAGAAAACCCCTCA-TAMRA-3'). In order to generate a standard for mRNA/cDNA copy quantification, the specific XCR1 gene fragments was amplified and cloned into pZErO vector using the Zero Background cloning kit (Invitrogen, Groningen, The Netherlands). For qPCR, primers were mixed with 10 µl ABsolute QPCR Mix including ROX (ABgene, Epsom, UK) and 1/10th of the cDNA in a 20 µl PCR-reaction. PCR was performed and quantified on the ABI Prism 7000 or 7700 Sequence Detection Systems (Applied Biosystems, Foster City, Calif., USA) with initial enzyme activation for 15 min at 95° C. followed by 50 cycles (95° C., 15 s; 60° C., 1 min). For quantification, several dilutions of the cloned gene fragment ranging from $10^0$ to $10^8$ copies were run in parallel to generate a standard curve. The results are shown in the following table 1.

TABLE 1

Quantification of number of mRNA copies

| Cell type | number of mRNA copy/10000 cells |
|---|---|
| splenocytes | 912 |
| T cells | 15 |
| B cells | 16 |
| NK cells | 0 |
| granulocytes | 5 |
| macrophages | 41 |
| CD11c$^+$CD8$^+$DC | 925 |
| CD11c$^+$CD8$^-$ DC | 148717 |

Example 2: Selective Activation of CD8$^+$DC by XCL1

Figure 1:
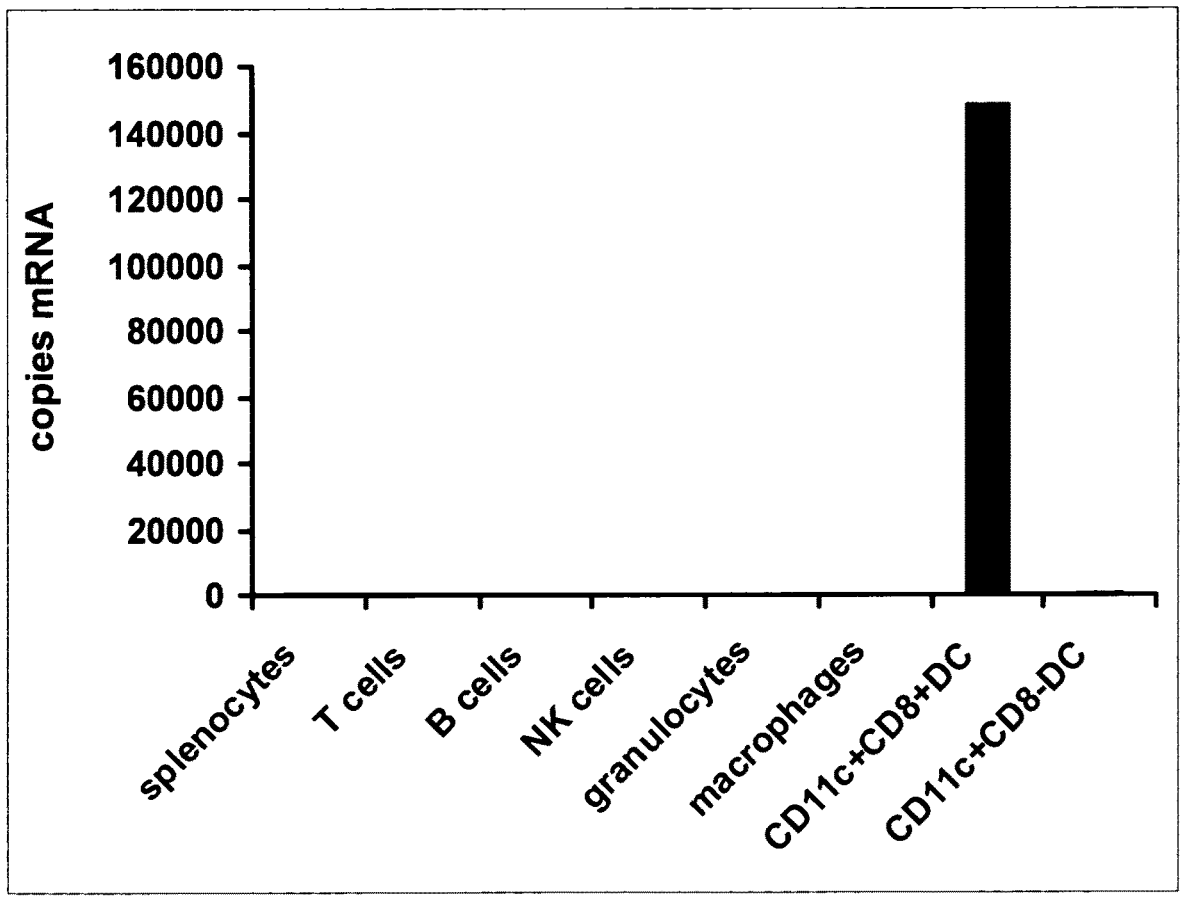
Figure 2A:
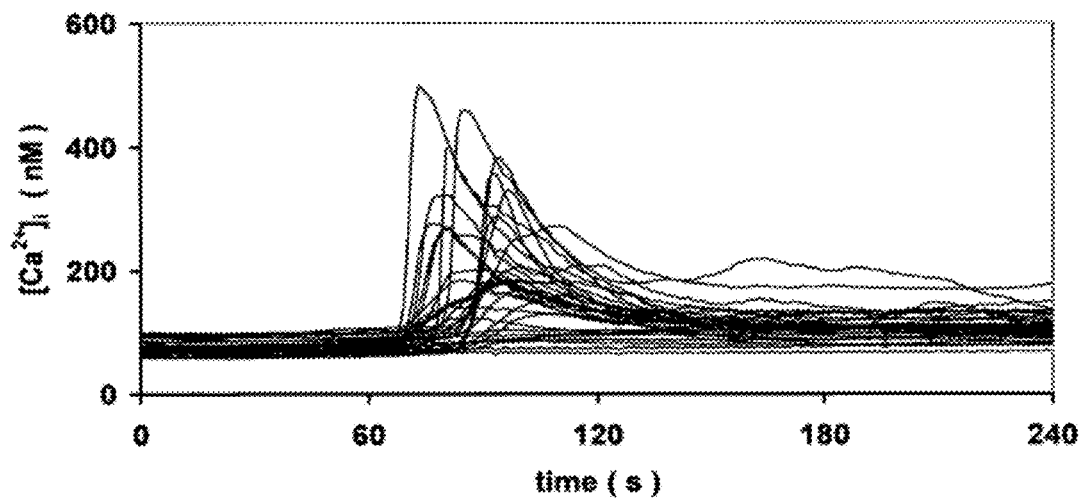
Figure 2B:
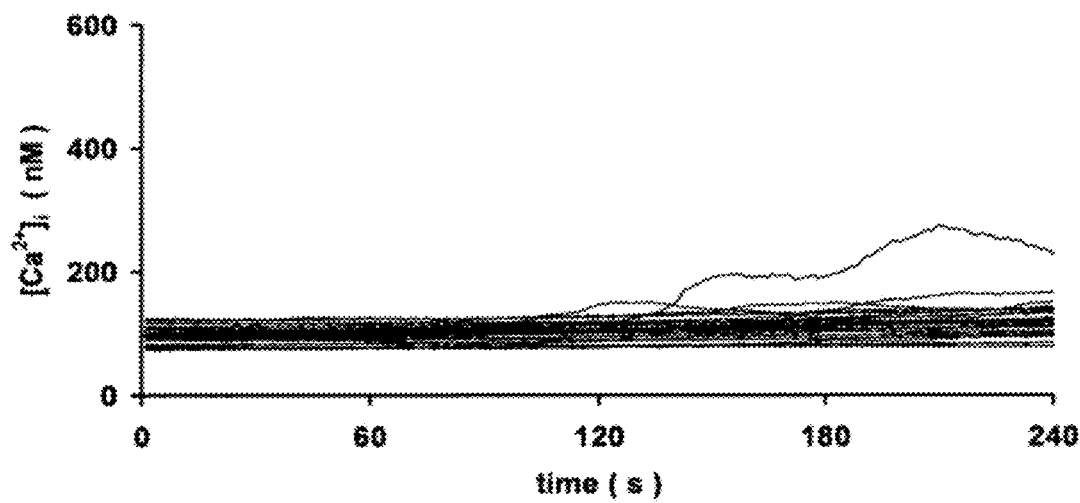

CD8$^+$ and CD8$^-$ DC, freshly sorted to a purity>95% by flow sorting as described in Example 1, were supplemented with 2 µM fura-2/AM (Molecular Probes, Brattleboro) and allowed to settle on poly-L-lysine-coated glass coverslips at 37° C. and 5% $CO_2$ for 30 min in a humidified atmosphere. Adherent cells were superfused with a HEPES-buffered solution containing (in mM) 128 NaCl, 6 KCl, 1 $MgCl_2$, 1 $CaCl_2$, 5.5 glucose, 10 HEPES, 0.2% (w/v) BSA, and mounted onto the stage of an inverted microscope (Axiovert 100, Zeiss, Jena, Germany). During application of XCL1 (100 nM of synthetic murine XCL1 (Dictagene, Lausanne, Switzerland)), fura-2 was sequentially excited with monochromatic light of 340 nm, 358 nm, 380 nm and 480 nm, and fluorescence emission was detected through a 512 nm long pass filter with a cooled CCD-camera (TILL-Photonics, Gräfelfing, Germany). Weakly interfering signals of FITC-labeled antibodies bound to CD8$^+$ DC were eliminated, and $[Ca^{2+}]_i$ was calculated after spectral unmixing (Lenz J. Cell Biol. 2002, 179:291-301). Data represent intracellular $Ca^{2+}$ concentrations ($[Ca^{2+}]_i$) in 45-56 single cells (black lines) measured in 3 independent experiments. Thick black lines: mean $[Ca^{2+}]_i$ signal averaged over all cells measured. The results demonstrate that XCL1 induces a strong $Ca^{2+}$-signal in CD8$^+$DC (FIG. 2, A), but not CD8$^-$DC (FIG. 2, B). The results thus demonstrate the capacity of XCL1 to specifically activate CD8$^+$DC and XCL1 thus acts as an adjuvant for XCR1-bearing APC.

Figures 3A, 3B:
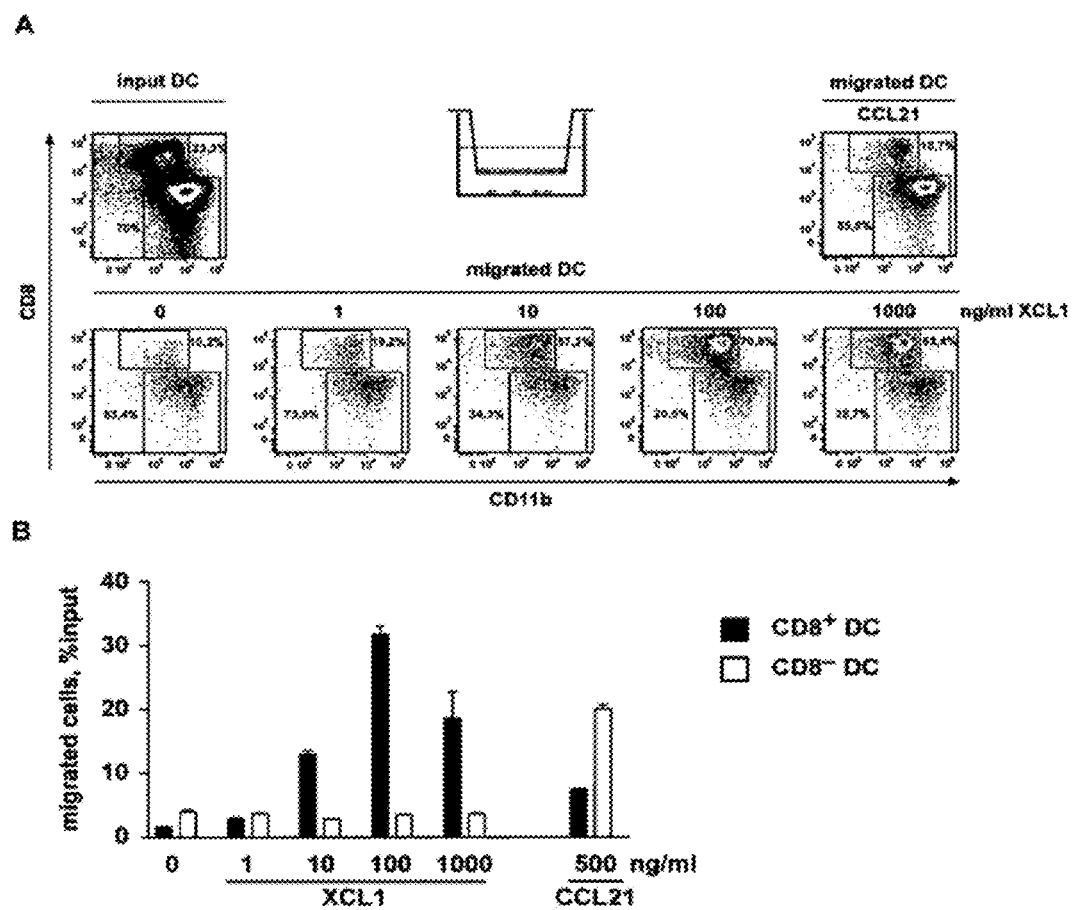
FIG. 3A-FIG. 3B show the percentage of migrated splenic CD8$^+$ DC and CD8$^-$DC in an in vitro transwell chemotaxis assay in the presence of 1-1000 ng/ml XCL1 and 500 ng/ml CCL21. Only CD8$^+$ DC migrate in response to XCL1.

Example 3: XCL1 Induces Chemotaxis of CD8$^+$DC, but not of CDd8$^-$DC, B Cells, T Cells, or NK Cells CD11c$^+$ cells were highly enriched from C57BL/6 splenocytes by magnetic separation using CD11c-microbeads according to the manufacturer's protocol (Miltenyi Biotec, Bergisch Gladbach, Germany). CD11c$^+$ cells (0.5-1×10$^6$) were suspended in 100 medium and transferred to a 6.5 mm Transwell Permeable Support containing a 5-µm pore polycarbonate membrane (Corning Costar Co., Acton, Mass., USA). The Transwell Permeable Support was inserted into 24 well plate (Corning Costar Co., supra) filled with 600 µl medium containing either serial dilutions of chemically synthesized XCL1/ATAC (Dictagene, Lausanne, Switzerland) or with 500 ng/ml CCL21 (chemokine (C—C motif) ligand 21; R&D Systems, Minneapolis, Minn., USA), the latter used as a positive control; all experiments were performed in duplicates. Cells were incubated for 120-150 minutes at 37° C. in a cell incubator. The lower side of the membrane was gently rinsed and the cells in the lower chamber were analyzed by flow cytometry for the expression of CD8 (53-6.72-FITC; ATCC, supra), CD11b (5C6-PE; ATCC, supra) and CD11c (N418-Cy5; ATCC, supra). Cell suspensions from each well were analyzed for a defined time (5 min) and the absolute number of live cells (DAPI-negative) was determined. The percentage of migrated cells was calculated by dividing the number of cells in the lower chamber by the number of input cells [number migrated cells/number input cells×100]. A representative experiment is shown in FIG. 3. In response to XCL1, CD8$^+$ DC display the characteristic bell curve of chemotactic migration with no migration at a concentration of 1 ng/ml, a maximum migration at 100 ng/ml and a declining response at 1000 ng/ml. CD8$^-$ DC did not respond to XCL1 but migrated in the presence of CCL21.

Figures 4A, 4B:
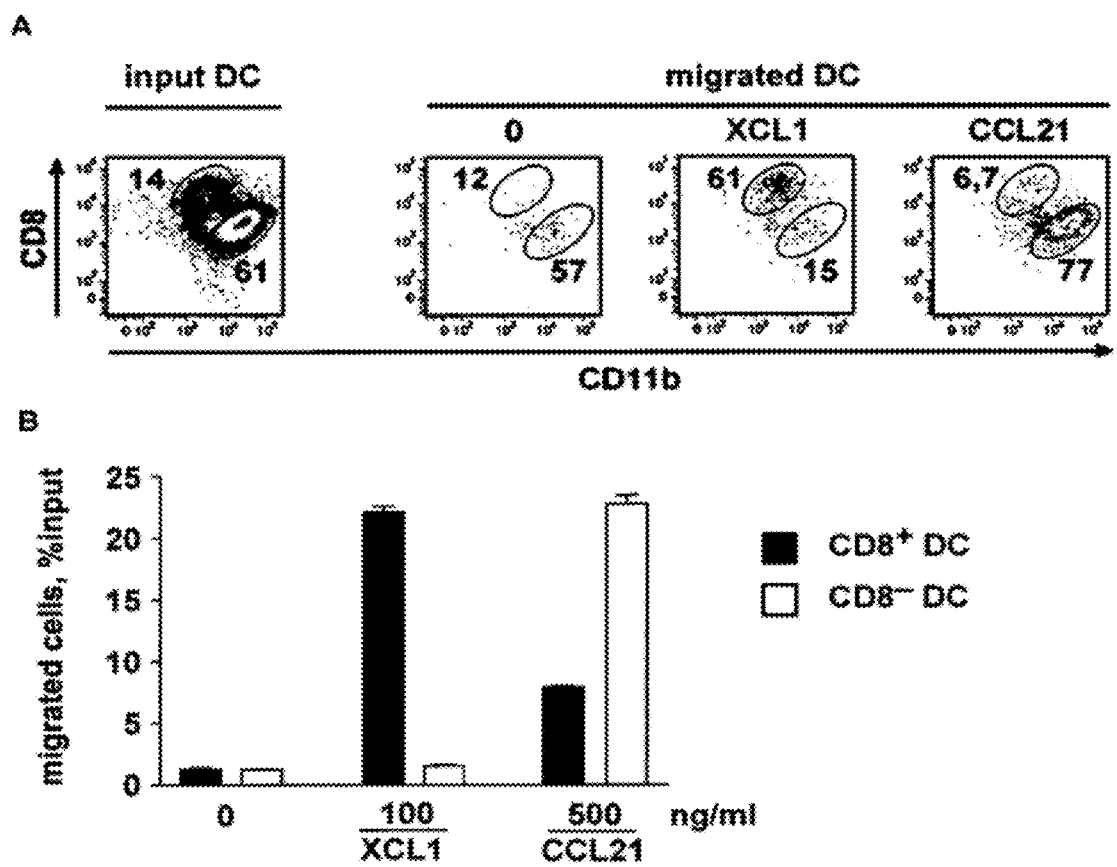
FIG. 4A-FIG. 4B show the percentage of migrated lymph node CD8$^+$ DC and CD8$^-$ DC in an in vitro transwell chemotaxis assay in the presence of 100 ng/ml XCL1 and 500 ng/ml CCL21. Only CD8+ DC migrate in response to XCL1.

DC from peripheral lymph nodes were isolated by collagenase digestion of the tissues, followed by positive magnetic sorting with CD11c-microbeads as described above. The chemotaxis assay was performed in Costar Transwell Chambers as above, using XCL1 at a concentration of 100 ng/ml and CCL21 in a concentration of 500 ng/ml. Cells by analyzed by flow cytometry, and the percentage of migrated cells was calculated as above. Again, only $CD8^+$ DC migrated in response to XCL1, while $CD8^-$ DC responded only to CCL21 (FIG. 4).

Figures 5A, 5B, 5C:
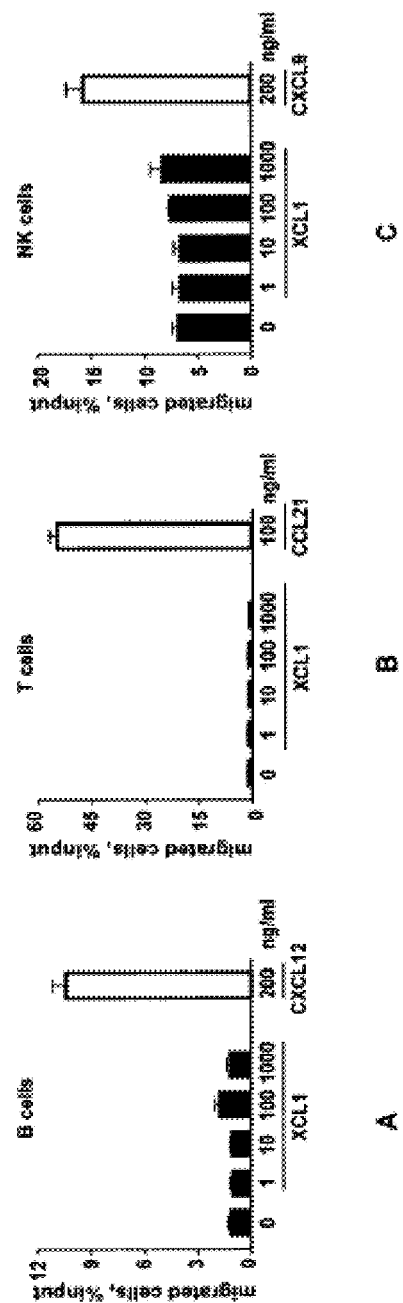
FIG. 5A-FIG. 5C show the migration behaviour of splenic B cells, T cells and NK cells in an in vitro transwell chemotaxis assay in the presence of 1-1000 ng/ml XCL1 or 200 ng/ml CXCL12, 100 ng/ml CCL21 or 200 ng/ml CXCL9, respectively. None of the cell populations migrate in response to XCL1.

To investigate the chemotactic response of other splenic cell populations, T cells were isolated by positive magnetic selection from C57BL/6 splenocytes with anti-CD90 conjugated beads, NK cells with anti-49b conjugated beads, and B cells with a combination of biotinylated anti-CD19 antibody (clone 1D3) and anti-Biotin conjugated beads, according to the manufacturer's instructions (see also Example 1). The chemotaxis assays were performed as above using serial dilutions of XCL1/ATAC. The positive control for B cells was CXCL12 (chemokine (C—X—C motif) ligand 12) at 200 ng/ml, CCL21 (chemokine (C—C motif) ligand 21) for T cells at 100 ng/ml, and CXCL9 ((chemokine (C—X—C motif) ligand 9) for NK cells at 200 ng/ml (all from R&D Systems, Minneapolis, Minn., USA). B cells, T cells, or NK cells failed to respond to XCL1/ATAC with chemotaxis, while the respective positive controls induced significant cell migration in these cell populations (FIG. 5). These experiments demonstrated that XCL1 induces chemotaxis in $CD8^+$DC, but not in $CD8^-$DC, T cells, B cells, or NK cells. These experiments thus demonstrated that XCL1 acts as a specific adjuvant for XCR1-bearing APC.

Example 4: XCL1-Facilitated Cell/Antigen Uptake into $CDd8^+$ Dendritic Cells

Mice deficient for XCL1 ("ATAC-KO") were generated by disruption of the murine ATAC gene in embryonic stem cells by homologous recombination using a targeting vector in which exons two and three of the ATAC gene were replaced by the inverted neomycin gene (FIG. 6). Correctly targeted embryonic stem cells, as identified by Southern blotting, were used for the generation of chimeric mice. After germ-line transmission of the mutant allele and breeding of heterozygous ATAC deficient mice inter se, homozygous ATAC-deficient mice were born at expected Mendelian frequency in the $F_2$-generation and backcrossed to the C57BL/6 background for 10 generations. The murine pre-B cell line 300-19 (Alt et al., 1981, Cell 27, 381-90) was transfected by electroporation with the $BCMGS_{neo}$ vector (Karasuyama et al., 1989, J Exp Med 169, 13-25) into which the complete coding region of murine XCL1 (GenBank Acc. No.: NM_008510) was cloned by standard methods. After subcloning in G418-containing selection medium, a cell line (referred to as muATAC/300-19) stably secreting murine XCL1/ATAC was obtained, as determined by intracellular flow cytometry (Dorner et al., 2002, Proc. Natl. Acad. Sci. USA 99, 6181-86). Wild-type 300-19 ("wt/300-19") cells and muATAC/300-19 cells were fluorescence-labeled by incubation with 10 µM 5,6-carboxyfluorescein succinimidyl ester (CFSE, Molecular Probes) for 10 min at 37° C., washed, and injected ($10 \times 10^6$ cells each) intravenously into female XCL1-deficient C57BL/6 ("ATAC-KO") mice; control mice were injected with PBS only. After 12 h, mice were sacrificed, the spleens removed and the splenocytes isolated according to standard methods. Splenocytes were stained for CD3, CD4, CD8, CD11b, CD11c, CD19, MHC II, and NK1.1 by standard methods and the CSFE signal was correlated to cell surface markers by analysis on the LSR II (BD Biosciences) flow cytometer (result is shown in FIG. 7) using FlowJo (Tree Star Inc., Ashland, Oreg., USA) for evaluation of the data. The results demonstrated that already 300-19 wild-type cells were taken up by $CD8^+$DC in the spleen (FIG. 8A). However, the XCL1-transfected 300-19 cells ("muATAC/300-19") were taken up to a clearly higher degree (increase of around 50%) (FIG. 8A). These results demonstrated that XCL1 facilitates antigen uptake by $CD11c^+CD8^+$DC. No cell uptake was observed by splenic $CD11c^+CD8^-$ DC (FIG. 8B).

Example 5: Expression of ATAC by $CD4^+$ T Cells During Induction of Tolerance or Immunity In Vivo Splenic cells containing $5-7 \times 10^6$ $KJ1-26^+$ transgenic DO11.10 $CD4^+$ T cells (Murphy et al., 1990, Science 250, 1720-3) were adoptively transferred into syngeneic BALB/c mice. These transgenic DO11.10 $CD4^+$ T cells are specific for chicken ovalbumin (OVA) peptide 323-339 (ISQAVHAAHAEINEAGR). Recipient mice were immunized with 100 µg OVA, or 100 µg OVA+ the adjuvant LPS (10 µg) into footpads. Alternatively, recipient mice were immunized with 2 mg OVA injected intravenously. OVA-specific $KJ1-26^+$ $CD4^+$ T cells were recovered from the recipients after 14 h, 24 h, or 48 h by flow cytometry cell sorting (purity>97%), either from the draining popliteal lymph nodes (in the case of footpad OVA injection), or from all peripheral lymph nodes (in the case of intravenous OVA injection). Total RNA was isolated from the recovered transgenic T cells and subjected to gene expression analysis using a custom TaqMan Low Density Array (Applied Biosystems). The data obtained are listed in Table 2.

The Ct-values (a parameter obtained when using quantitative PCR) increased in all experimental setups at 14, 24, and 48 h approximately by the value of 5, when compared to the 0 h time point control. This increase represents an approximately 30 fold increase in XCL1 mRNA expression upon in vivo activation of the transgenic T cells in all experimental conditions. These data indicate that XCL1 is expressed and utilized by the immune system, both at immunogenic as well as tolerogenic conditions. These data thus indicate that XCL1 can be used for delivery of a substance both to achieve immunity/memory (in the presence of a "danger signal") or to achieve tolerance (in the absence of a "danger signal").

TABLE 2

| | OVA s.c. | | OVA + LPS s.c. | | OVA i.v. | |
|---|---|---|---|---|---|---|
| time | Avg Ct 18S RNA | Ct XCL1 | Avg Ct 18S RNA | Ct XCL1 | Avg Ct 18S RNA | Ct XCL1 |
| 0 h | 7.55 | 33.94 | 7.55 | 33.94 | 7.55 | 33.94 |
| 14 h | 8.59 | 29.02 | 10.04 | 33.91 | 8.25 | 27.64 |
| 24 h | 7.20 | 28.99 | 9.53 | n.d. | 7.82 | 28.63 |
| 48 h | 5.96 | 28.64 | 6.03 | 32.04 | 6.20 | 30.85 |

Example 6: XCL1-Mediated, Improved Antigen Recognition by $CD8^+$ T Cells Interacting with $CD8^+$DC In Vivo ATAC-KO mice (see Example 4) were backcrossed 10× to the C57BL/6 background and then backcrossed to OT-I transgenic mice ("OT-I ATAC-KO"). OT-I transgenic mice express a transgenic T-cell receptor specific for the SIN- FEKL peptide (SEQ ID NO: 15) an 8 amino acid epitope of ovalbumin) derived from chicken ovalbumin (OVA) (Hogquist et al., 1994, Cell 76, 17-27). Total splenocytes containing $2 \times 10^{60}$T-I T cells were adoptively transferred into syngeneic C57BL/6 recipient mice by intravenous (i.v.) injection. In parallel, total splenocytes containing $2 \times 10^{60}$T-I ATAC-KO T cells were adoptively transferred into syngeneic C57BL/6 ATAC-KO recipient mice. In all cases, female donor and recipient mice were used. Twenty four hours after cell transfer, recipient mice were challenged with 100 ng OVA conjugated to an anti-DEC205 antibody ("DEC-205-OVA") to achieve a preferential delivery of antigen to $CD8^+DC$, as described previously (Bonifaz et al., 2002, J. Exp. Med. 196, 1627-38).

DEC-205-OVA was generated by incubating 1 mg anti-DEC-205 mAb NLDC-145 (obtained from Georg Kraal, Amsterdam) with 2 mg SMCC-activated OVA according to the manufacturer's protocol (Pierce Chemical Co.). Protein G precipitation of the reagent was performed to remove unconjugated OVA, and the amount of conjugated OVA per mg antibody was carefully determined by analyzing Coomassie-stained non-reducing SDS-gels. DEC-205-OVA was applied i.v. in a volume of 200 µl; control mice received PBS. Some mice were injected with DEC-205-OVA alone, which, in the absence of a "danger signal", has tolerogenic effects (Bonifaz et al., 2002, J. Exp. Med. 196, 1627-38). Other mice were injected with DEC-205-OVA in combination with 6 µg of anti-CD40 antibody FGK (obtained from Ton Rolink, Basel), in which the anti-CD40 mAb which provides "danger signals" to DC ((Bonifaz et al., 2002, J. Exp. Med. 196, 1627-38). Three days after DEC-205-OVA injection, mice were sacrificed and the splenocytes were stained for CD3, CD8, CD90.1, and MHC II expression by standard methods, and analyzed on a LSR II flow cytometer using FlowJo software in order to determine the presence of OT-I $CD8^+$ T cells. In addition, splenocytes from the sacrificed mice were incubated in vitro with 50 ng/ml of peptide SIINFEKL in the presence of 5 µg/ml Brefeldin A for 5 h. After this period, OT-I T cells and OT-I ATAC-KO T cells were analyzed for secretion of IFN-γ by intracellular flow cytometry according to standard methods. The results demonstrated that in the absence of XCL1, the interaction of $CD8^+$T-I T cells with $CD8^+DC$, either under tolerogenic (no anti-CD40 mAb) or immunogenic (addition of anti-CD40 mAb) conditions, leads to reduced activation and expansion of T cells (FIG. 9). At the same time, the absence of XCL1 leads, either under tolerogenic or immunogenic conditions, to reduced differentiation of $CD8^+$ T cells into IFN-γ secreting effector T cells (FIG. 10). Both results demonstrate the activating and adjuvant effects of XCL1 on $CD8^+DC$ interacting with $CD8^+$ T cells.

Example 7: Generation of Monoclonal Antibodies Against the Human XCR1 (hXCR1)

Female BALB/c mice were immunized with a peptide representing the first 31 N-terminal amino acids of hXCR1 (MESSGNPEST TFFYYDLQSQ PCENQAWVFA T; SEQ ID NO: 18). The N-terminus of the peptide was coupled to keyhole limpet hemocyanin using glutaraldehyde (31-N-hXCR1-KLH; synthesis by P. Henklein, Charité, Berlin). Initial immunization was performed with 31-N-hXCR1-KLH (30 µg applied intraperitoneally and 30 µg subcutaneuosly) in complete Freund's adjuvant. Mice were boosted twice after 3-4 week intervals with 50 µg 31-N-hXCR1—KLH in incomplete Freund's adjuvant applied intraperitoneally. Six weeks after the second boost, mice were injected with the 31-N-hXCR1 peptide bound to bovine serum albumin (31-N-hXCR1-BSA) intravenously (50 µg) in saline. Three days later the mice were sacrificed and spleen cells were fused with the myeloma line P3X63Ag8.653 according to standard protocols for monoclonal antibody generation. Screening of the hybridoma supernatants was performed using the uncoupled 31-N-hXCR1 peptide adsorbed to 96-well plates in a standard ELISA assay. One hybridoma (6F8) gave a strong and consistent signal in the ELISA assay; the hybridoma was therefore subcloned and the 6F6 antibody used for further characterization of hXCR1. To this end, several hXCR1 transfectants were generated by cloning the entire coding region of hXCR1/hATACR (GenBank Acc. No.: L36149) into the vector $BCMGS_{neo}$ (supra) in such a fashion that it was either at the 3' or 5' end tagged with a c-myc epitope EQKLISEEDL (SEQ ID NO: 19). Subsequently, the murine myeloma line P3X63Ag8.653 was transfected by electroporation with either version of the vector and the two transfected cell lines "5' c-myc/hATACR/P3X" and "3' c-myc/hATACR/P3X" were established after subcloning in G418-containing selection medium. Included in the studies was also the murine cell line transfected with hXCR1 obtained from Dr. Bernhard Moser, Bern, Switzerland ("hATACR/300-19"). Supernatants of the mAb 6F8 were used to immunoprecipitate the hXCR1 protein from various cell lines (FIG. 11). To this end, lysates from the transfectants "5' c-myc/hATACR/P3X", "3' c-myc/hATACR/P3X", and "hATACR/300-19", and the respective wild-type lines were generated from $5-10 \times 10^6$ cells each according to standard methods (lysis buffer: 50 mM Tris/HCl (pH 8), 150 mM NaCl, 1 mM EDTA, +1% (v/v) Nonident P-40, 1 mM PMSF, 10 µM leupeptin A, 1 µM pepstatin, 10 µg/ml aprotinin). These lysates, after preclearing, were incubated with mAb 6F8 supernatant (5-10 ml), and immunoprecipitated with protein G beads according to standard methods. The immunoprecipitate was denatured in SDS buffer, separated on a reducing 12% SDS-gel, and electroblotted on a Immobilon P membrane (Millipore) according to standard methods. The blot was stained with a polyclonal rabbit-anti-hXCR1 serum (generated against a peptide representing the N-terminus of hXCR1, MESSGNPEST TFFYYDLQSQ PCENQAWVFA T, SEQ ID NO: 18, using a standard protocol) diluted 1:2500 in blocking buffer and developed using biotin-coupled goat-anti-rabbit-IgG (1:5000 in blocking buffer), avidin-alkaline phosphatase and the Western Light/CDP-Star detection system (Tropix). The detection of the light signal was with XOMatAR-film (Kodak). The rabbit anti-hXCR1 serum had been generated by immunizing rabbits 3× with 250 µg of the 31-N-hXCR1 peptide in complete Freund's adjuvant over a period 11 weeks.

Example 8: Generation of Recombinant Murine XCL1 in its Biologically Active Form Native murine XCL1 is generated in vivo by proteolytic removal of a signal peptide, resulting in a protein with N-terminal valine (Dorner et al., 1997, J. Biol. Chem. 272, 8817-23). To generate a corresponding recombinant murine XCL1 starting with N-terminal valine, amino acids 22-114 of full-length murine ATAC were fused to the C-terminus of a histidine-tagged SUMO-protein, using standard DNA recombinant technology and the expression vector pET SUMO (Invitrogen, Groningen, The Netherlands). The fusion protein was expressed in E. coli using standard protocols and purified by immobilized metal affinity chromatography (Ni-NTA Superflow, Qiagen, Hilden, Germany)

according to the manufacturer's protocol. Site-specific cleavage of the fusion protein was achieved by incubation with SUMO protease (Invitrogen) for 3 h at 37° C. A second immobilized metal affinity chromatography step was performed to remove the histidine-tagged SUMO fusion part. Using this protocol, a biologically active form of recombinant murine XCL1 protein was generated with high yield and purity (FIG. 12).

Example 9: Enhanced Cytoxicity by WT OT-I in Comparison to ATAC-KO OT-I

Transgenic CD8$^+$ T cells specific for OVA peptide were purified from splenocytes of OT-I or ATAC-KO OT-1 mice by magnetic depletion of other splenic cell populations using antibodies against CD4, CD11b, CD11c, NK1.1, and B220. OT-I or OT-I ATAC-KO T cells ($3 \times 10^5$) were adoptively transferred into syngeneic C57BL/6 or ATAC-KO mice, respectively. Both groups of mice were immunized 24 h later with $3 \times 10^6$ 300-19 cells transfected with OVA ("OVA/300-19"). OVA/300-19 cells were generated by electroporation of wild-type 300-19 cells with the BCMGS$_{neo}$ vector (Karasuyama et al., 1989, J Exp Med 169, 13-25) into which a truncated coding region of OVA (corresponding to amino acids 138-386; GenBank Acc. No.: NM_205152) was cloned by standard methods. At day 6 after immunization with OVA/300-19 cells, an in vivo cytotoxicity assay was performed as previously described (Romano et al., 2004, J. Immunol. 172, 6913-6921). Shortly, splenocytes of C57BL/6 mice were isolated and incubated for 1 h at 37° C., either in medium alone or in the presence of 10 μM of the specific OVA peptide SIINFEKL. After washing, peptide-pulsed cells were labeled with 10 μM 5,6-carboxyfluorescein diacetate succimidyl ester (CSFE, Molecular Probes, Oregon, USA), while unpulsed cells were labeled with 1 μM CSFE. Equal amounts of CSFE-low and CSFE-high/SIINFEKL splenocytes ($10 \times 10^6$ cells each) were injected into the OVA/300-19 immunized mice and the relative abundance of surviving CSFE-low and CSFE-high/SIINFEKL splenocytes was determined by flow cytometry 18 h later. OVA-specific cytotoxicity was calculated as described (Hernandez et al., 2007, J. Immunol. 178, 2844-2852). Injection of OVA/300-19 cells induced 32±4% OVA-specific cytotoxicity in the presence of OT-I T cells, but only 14±10% cytotoxicity in the presence of ATAC-KO OT-I T cells (FIG. 13). Control immunization of mice with wild-type 300-19 cells did not induce cytotoxicity by transferred OT-I T cells. This experiment demonstrates that ATAC acts as an adjuvant in the induction of CD8$^+$ T cell cytotoxicity.

Example 10: XCR1 Expression In Vivo is Limited to a Supopulation of DC

Organ tissues from B6.129P2-Xcr1$^{tm1Dgen}$/J mice (The Jackson Laboratory, Maine, USA), in which the ATAC gene has been replaced by a lacZ-reporter gene ("knock-in"), were analyzed for in situ B-galactosidase activity. To this end, pieces of organs were immersed in 0.1% glutaraldehyde and 4% paraformaldehyde in PBS for 4 h at 4° C., incubated in 10% sucrose/PBS at 4° C. overnight, and snap frozen. Cryosections of the tissues were re-fixed in 0.1% glutaraldehyde and 4% paraformaldehyde in PBS for 10 min at RT, washed 3× with cold PBS (pH 7.4) for 5 min, incubated with X-Gal staining solution (Sanes et al., 1986, EMBO J. 5, 3133-3142) overnight at 37° C., washed 3× in PBS, and counterstained by Neutral Red.

Expression of lacZ (and thus the XCR1 gene) was observed in the spleen, thymus, lymph nodes, lung, liver, testis, ovary, placenta, Payer's patches, small intestine, and large intestine.) In the spleen, the signals obtained corresponded to the distribution pattern of CD8$^+$ DC. In the other organs the (usually low) abundance, the morphology, and the tissue distribution of the signals were fully compatible with the concept of an XCR1 expression limited to a subpopulation of DC.

Example 11: Expression of XCR1 in Murine Splenocytes Analyzed by Flow Cytometry

Splenocytes from B6.129P2-Xcr1$^{tm1Dgen}$/J mice mice were isolated and stained for CD3, CD4, CD8, CD19, CD11c, MHC II and NK.1.1 by standard methods. Expression of the lacZ reporter gene, assayed with fluorescein di-β-D-galacto pyranoside (FDG, Invitrogen) according to the manufacturer's protocol, was detected in 7%-10% of CD4$^-$CD8$^-$ DC and in 75%-90% of CD8$^+$ DC, but not in CD4$^+$ DC (FIG. 14). All other splenic populations were negative. These results demonstrate that XCR1 is, within the immune system, only expressed in a subpopulation of DC, which in the spleen mostly carries the CD8 cell surface marker.

The invention claimed is:

1. A method for inducing, in a subject, a memory immune response against a substance, comprising administering to the subject a delivery system, or nucleic acids encoding said delivery system, suitable for delivering the substance into a chemokine (C motif) receptor 1 (XCR1) positive professional antigen-presenting cell, the delivery system comprising i) a chemokine (C motif) ligand 1 (XCL1);

ii) the substance to be delivered, wherein the substance is a peptide of a viral, bacterial, or fungal pathogenic protein or a tumor antigen, the substance being bound to the XCL1; and iii) a danger signal adjuvant, wherein said administering of the delivery system to the subject induces a memory immune response to the substance in the subject.

2. The method of claim 1, wherein the method prevents or treats a tumor and/or an infection.

3. The method of claim 1, wherein the memory immune response is a Th1 response.

4. The method of claim 3, wherein the Th1 response is a Th1 cytotoxic response.

5. The method of claim 1, wherein the delivery system is composed of one (poly)peptide.

6. The method of claim 1, wherein the "danger signal" adjuvant is not bound to the other components of the delivery system.

* * * * *